US 12,290,114 B2

United States Patent
Andon et al.

(10) Patent No.: US 12,290,114 B2
(45) Date of Patent: May 6, 2025

(54) ADAPTIVE SUPPORT APPAREL SYSTEMS AND METHODS

(71) Applicant: NIKE, Inc., Beaverton, OR (US)

(72) Inventors: Christopher Andon, Portland, OR (US); Michael T. Horne, Beaverton, OR (US); Nicola J. Reynolds, Beaverton, OR (US); Summer L. Schneider, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 18/527,785

(22) Filed: Dec. 4, 2023

(65) Prior Publication Data

US 2024/0172812 A1 May 30, 2024

Related U.S. Application Data

(63) Continuation of application No. 16/887,118, filed on May 29, 2020, now Pat. No. 11,832,657.
(Continued)

(51) Int. Cl.
*A41C 3/00* (2006.01)
*A41D 1/00* (2018.01)
(Continued)

(52) U.S. Cl.
CPC .............. *A41C 3/0028* (2013.01); *A41D 1/002* (2013.01); *A41D 31/18* (2019.02); *A61B 5/024* (2013.01);
(Continued)

(58) Field of Classification Search
CPC ....... A41C 3/0028; A41D 31/18; A41D 1/002
(Continued)

(56) References Cited

U.S. PATENT DOCUMENTS

| 6,032,299 A | 3/2000 | Welsh |
| 8,083,693 B1 | 12/2011 | Mckeon et al. |

(Continued)

FOREIGN PATENT DOCUMENTS

| CN | 201767077 | 3/2011 |
| CN | 104582519 A | 4/2015 |

(Continued)

OTHER PUBLICATIONS

"U.S. Appl. No. 16/887,068, Non Final Office Action mailed Mar. 31, 2023", 10 pgs.
(Continued)

*Primary Examiner* — Gloria M Hale
(74) *Attorney, Agent, or Firm* — Schwegman, Lundberg & Woessner, P.A.

(57) ABSTRACT

Systems and apparatus related to adaptive support garments including adaptive support structures, lacing systems, and an adaptive engine are discussed. In an example, an adaptive support garment includes a support structure, a plurality of lace guides, a lace cable, and an adaptive engine. The support structure is configured to wrap around a portion of anatomy of a wearer and apply a compression on the portion of anatomy. The plurality of lace guides are disposed on the support structure. The lace cable extends through the lace guides to form a lacing pattern over a lacing region of the support structure. The adaptive engine is coupled to the support structure and engages with the lace cable. The adaptive engine is also configured to increase or decrease tension on the lace cable to increase or decrease compression of the support structure on the portion of anatomy, respectively.

20 Claims, 40 Drawing Sheets

Related U.S. Application Data

(60) Provisional application No. 62/855,712, filed on May 31, 2019.

(51) Int. Cl.
| | |
|---|---|
| *A41D 31/18* | (2019.01) |
| *A61B 5/00* | (2006.01) |
| *A61B 5/024* | (2006.01) |
| *A61B 5/103* | (2006.01) |
| *A61B 5/11* | (2006.01) |
| *G16H 50/30* | (2018.01) |

(52) U.S. Cl.
CPC .......... *A61B 5/1038* (2013.01); *A61B 5/1118* (2013.01); *A61B 5/6804* (2013.01); *G16H 50/30* (2018.01); *A61B 2562/0219* (2013.01); *A61B 2562/0261* (2013.01); *A61B 2562/0271* (2013.01)

(58) Field of Classification Search
USPC .......................................................... 450/86
See application file for complete search history.

(56) References Cited

U.S. PATENT DOCUMENTS

| | | | |
|---|---|---|---|
| 9,526,300 | B2 | 12/2016 | Krengel |
| 9,723,878 | B1 | 8/2017 | Goff |
| 10,085,517 | B2 | 10/2018 | Beers et al. |
| 10,166,164 | B2 | 1/2019 | Johnson et al. |
| 11,825,886 | B2* | 11/2023 | Munro ............... B65H 75/4486 |
| 11,832,657 | B2 | 12/2023 | Andon et al. |
| 2005/0251074 | A1 | 11/2005 | Latham |
| 2008/0113143 | A1 | 5/2008 | Taylor |
| 2009/0064396 | A1 | 3/2009 | Ghajar |
| 2009/0082707 | A1 | 3/2009 | Rumsey |
| 2009/0204042 | A1 | 8/2009 | Park |
| 2010/0154255 | A1 | 6/2010 | Robinson et al. |
| 2011/0072566 | A1 | 3/2011 | Kovacevich et al. |
| 2013/0109276 | A1 | 5/2013 | Sporn |
| 2013/0203319 | A1* | 8/2013 | Torres .................. A41C 3/0028 450/59 |
| 2014/0052036 | A1 | 2/2014 | Park |
| 2014/0259301 | A1 | 9/2014 | Berns et al. |
| 2017/0128306 | A1 | 5/2017 | Chase et al. |
| 2017/0265594 | A1 | 9/2017 | Walker et al. |
| 2017/0273365 | A1 | 9/2017 | Muhlenfeld |
| 2017/0312161 | A1 | 11/2017 | Johnson et al. |
| 2017/0312165 | A1 | 11/2017 | Johnson et al. |
| 2018/0206586 | A1 | 7/2018 | Akay et al. |
| 2018/0255883 | A1 | 9/2018 | Brandt et al. |
| 2019/0059461 | A1 | 2/2019 | Walker |
| 2019/0082773 | A1 | 3/2019 | Rushbrook et al. |
| 2019/0216394 | A1 | 7/2019 | Goldman |
| 2019/0246745 | A1 | 8/2019 | Bock et al. |
| 2020/0163416 | A1* | 5/2020 | Kwon ...................... A61B 5/11 |
| 2020/0375268 | A1 | 12/2020 | Munro et al. |
| 2020/0375269 | A1 | 12/2020 | Andon et al. |
| 2020/0375506 | A1 | 12/2020 | Bishop et al. |
| 2023/0301371 | A1 | 9/2023 | Bishop et al. |

FOREIGN PATENT DOCUMENTS

| | | |
|---|---|---|
| CN | 204667401 | 9/2015 |
| CN | 105495712 | 4/2016 |
| CN | 105615103 | 6/2016 |
| CN | 105831827 A | 8/2016 |
| CN | 207461481 | 6/2018 |
| CN | 108370645 | 8/2018 |
| CN | 207754671 | 8/2018 |
| CN | 109007995 A | 12/2018 |
| CN | 109068764 A | 12/2018 |
| CN | 114269188 A | 4/2022 |
| CN | 114423307 A | 4/2022 |
| CN | 114502024 A | 5/2022 |
| CN | 118489971 | 8/2024 |
| EP | 2596714 | 5/2013 |
| EP | 2687114 A2 | 1/2014 |
| JP | 2006037321 | 2/2006 |
| JP | 2017160557 | 9/2017 |
| JP | 2022535765 A | 8/2022 |
| JP | 2022537102 A | 8/2022 |
| JP | 2022541983 | 9/2022 |
| KR | 20190009640 A | 1/2019 |
| KR | 20220005602 A | 1/2022 |
| KR | 20220017437 A | 2/2022 |
| KR | 20220017950 A | 2/2022 |
| TW | I858069 | 10/2024 |
| WO | WO-2014138297 A1 | 9/2014 |
| WO | WO-2015160790 A1 | 10/2015 |
| WO | WO-2015181661 A1 | 12/2015 |
| WO | WO-2017087862 A1 | 5/2017 |
| WO | WO-2017172777 A1 | 10/2017 |
| WO | 2018049532 | 3/2018 |
| WO | WO-2019046516 A1 | 3/2019 |
| WO | WO-2020243391 A1 | 12/2020 |
| WO | WO-2020243395 A1 | 12/2020 |
| WO | WO-2020243401 A1 | 12/2020 |

OTHER PUBLICATIONS

"U.S. Appl. No. 16/887,068, Notice of Allowance mailed Jul. 26, 2023", 6 pgs.

"U.S. Appl. No. 16/887,068, Response filed Jun. 29, 2023 to Non Final Office Action mailed Mar. 31, 2023", 8 pgs.

"U.S. Appl. No. 16/887,093, Appeal Brief filed Sep. 12, 2022", 22 pgs.

"U.S. Appl. No. 16/887,093, Examiner Interview Summary mailed Oct. 27, 2023", 2 pgs.

"U.S. Appl. No. 16/887,093, Final Office Action mailed Mar. 11, 2022", 24 pgs.

"U.S. Appl. No. 16/887,093, Final Office Action mailed Aug. 23, 2023", 37 pgs.

"U.S. Appl. No. 16/887,093, Non Final Office Action mailed Oct. 18, 2021", 19 pgs.

"U.S. Appl. No. 16/887,093, Non Final Office Action mailed Oct. 18, 2022", 27 pgs.

"U.S. Appl. No. 16/887,093, Response filed Feb. 17, 2022 to Non Final Office Action mailed Oct. 18, 2021", 10 pgs.

"U.S. Appl. No. 16/887,093, Response filed Apr. 17, 2023 to Non Final Office Action mailed Oct. 18, 2022", 10 pgs.

"U.S. Appl. No. 16/887,093, Response filed Nov. 22, 2023 to Final Office Action mailed Aug. 23, 2023", 11 pgs.

"U.S. Appl. No. 16/887,118, Non Final Office Action mailed Mar. 31, 2023", 10 pgs.

"U.S. Appl. No. 16/887,118, Notice of Allowance mailed Jul. 26, 2023", 5 pgs.

"U.S. Appl. No. 16/887,118, Response filed Jun. 29, 2023 to Non Final Office Action mailed Mar. 31, 2023", 8 pgs.

"Chinese Application Serial No. 202080052919.9, Office Action mailed Oct. 28, 2023", With English translation, 11 pgs.

"Chinese Application Serial No. 202080055625.1, Office Action mailed Sep. 22, 2023", With English translation, 17 pgs.

"European Application Serial No. 20812964.3, Extended European Search Report mailed Jul. 3, 2023", 9 pgs.

"European Application Serial No. 20812964.3, Response filed Jun. 30, 2022 to Communication Pursuant to Rules 161 and 162 EPC", 10 pgs.

"European Application Serial No. 20813297.7, Response to Communication pursuant to Rules 161 and 162 EPC filed Jul. 3, 2022", 11 pgs.

"European Application Serial No. 20813297.7, Extended European Search Report mailed Jun. 26, 2023", 9 pgs.

"European Application Serial No. 20815208.2, Extended European Search Report mailed Jan. 16, 2023", 8 pgs.

"European Application Serial No. 20815208.2, Response filed Jun. 30, 2022 to Communication Pursuant to Rules 161 and 162 EPC", 10 pgs.

(56) References Cited

OTHER PUBLICATIONS

"European Application Serial No. 20815208.2, Response filed Jul. 26, 2023 to Extended European Search Report mailed Jan. 16, 2023", 143 pgs.
"International Application Serial No. PCT/US2020/035065, International Preliminary Report on Patentability mailed Dec. 9, 2021", 7 pgs.
"International Application Serial No. PCT/US2020/035065, International Search Report mailed Sep. 17, 2020", 3 pgs.
"International Application Serial No. PCT/US2020/035065, Written Opinion mailed Sep. 17, 2020", 5 pgs.
"International Application Serial No. PCT/US2020/035073, International Preliminary Report on Patentability mailed Dec. 9, 2021", 7 pgs.
"International Application Serial No. PCT/US2020/035073, International Search Report mailed Sep. 16, 2020", 3 pgs.
"International Application Serial No. PCT/US2020/035073, Written Opinion mailed Sep. 16, 2020", 5 pgs.
"International Application Serial No. PCT/US2020/035082, International Preliminary Report on Patentability mailed Dec. 9, 2021", 7 pgs.
"International Application Serial No. PCT/US2020/035082, International Search Report mailed Sep. 18, 2020", 3 pgs.
"International Application Serial No. PCT/US2020/035082, Written Opinion mailed Sep. 18, 2020", 5 pgs.
"Japanese Application Serial No. 2021-570966, Voluntary Amendment Filed Feb. 3, 2022", W/ Current English Claims, 7 pgs.
"Japanese Application Serial No. 2021-570982, Voluntary Amendment Filed Feb. 3, 2022", w/English Claims, 7 pgs.
"Japanese Application Serial No. 2021-571019, Voluntary Amendment Filed Feb. 7, 2022", W/ English Claims, 7 pgs.
"Korean Application Serial No. 10-2021-7043309, Voluntary Amendment filed Jan. 3, 2022", w/ English claims, 18 pgs.
"Taiwanese Application Serial No. 109118181, Office Action mailed Aug. 30, 2023", w/ English Translation, 25 pgs.
Steele, J R, et al., "The Bionic Bra: Using electromaterials to sense and modify breast support to enhance active living", Journal of Rehabilitation and Assistive Technologies Engineering, (Jan. 2018), 9 pgs.
"Chinese Application Serial No. 202080052919.9, Office Action mailed Mar. 8, 2024", W English Translation, 13 pgs.
"U.S. Appl. No. 16/887,093, Non Final Office Action mailed Mar. 25, 2024", 35 pgs.
"Chinese Application Serial No. 202080055625.1, Response filed Jan. 19, 2024 to Office Action mailed Sep. 22, 2023", w English claims, 70 pgs.
"Chinese Application Serial No. 202080055625.1, Response filed Apr. 3, 2024 to Office Action mailed Sep. 22, 2023", With English Machine Translation and English claims, 168 pgs.
"Chinese Application Serial No. 202080055444.9, Decision of Rejection mailed Apr. 30, 2024", With English Machine Translation, 24 pgs.
"Chinese Application Serial No. 202410337046.6, Notification to Make Rectification (210302) mailed May 20, 2024", With English Machine Translation, 3 pgs.
"Chinese Application Serial No. 202080055444.9, Office Action mailed Nov. 4, 2023", With English translation, 22 pgs.
"Taiwanese Application Serial No. 109118181, Response filed Dec. 1, 2023 to Office Action mailed Aug. 30, 2023", w English Claims, 89 pgs.
"European Application Serial No. 20813297.7, Response filed Jan. 22, 2024 to Extended European Search Report mailed Jun. 26, 2023", 8 pgs.
"Japanese Application Serial No. 2021-570966, Notification of Reasons for Refusal mailed Feb. 6, 2024", w English Translation, 20 pgs.
"Japanese Application Serial No. 2021-571019, Notification of Reasons for Refusal mailed Feb. 6, 2024", With English Machine Translation, 9 pgs.
"Japanese Application Serial No. 2021-570982, Notification of Reasons for Refusal mailed Feb. 6, 2024", w English Translation, 14 pgs.
"Chinese Application Serial No. 202080055625.1, Office Action mailed Feb. 3, 2024", w English Translation, 17 pgs.
"Chinese Application Serial No. 202080052919.9, Response filed Feb. 28, 2024 to Office Action mailed Oct. 28, 2023", With English Machine Translation, 164 pgs.
"European Application Serial No. 20812964.3, Response filed Jan. 18, 2024 to Extended European Search Report mailed Jul. 3, 2023", 23 pgs.
"Chinese Application Serial No. 202080055444.9, Response filed Mar. 4, 2024 to Office Action mailed Nov. 4, 2023", With English Machine Translation, 8 pgs.
"European Application Serial No. 20813297.7, Communication Pursuant to Article 94(3) EPC mailed Mar. 5, 2024", 5 pgs.
"European Application Serial No. 20812964.3, Communication Pursuant to Article 94(3) EPC mailed Mar. 5, 2024", 5 pgs.
"Chinese Application Serial No. 202080055625.1, Decision of Rejection mailed May 24, 2024", With English Machine Translation, 24 pgs.
"U.S. Appl. No. 16/887,093, Response filed Jun. 25, 2024 to Non Final Office Action mailed Mar. 25, 2024", 11 pgs.
"Chinese Application Serial No. 202080052919.9, Response filed Jul. 8, 2024 to Office Action mailed Mar. 8, 2024", w current English claims, 5 pgs.
"Chinese Application Serial No. 202410337046.6, Response filed Jul. 22, 2024 to Notification to Make Rectification (210302) mailed May 20, 2024", With English Machine Translation, 215 pgs.
"Chinese Application Serial No. 202080055444.9, Response filed Jul. 30, 2024 to Decision of Rejection mailed Apr. 30, 2024", w English claims, 12 pgs.
"Japanese Application Serial No. 2021-571019, Response filed Jul. 31, 2024 to Notification of Reasons for Refusal mailed Feb. 6, 2024", W English Claims, 18 pgs.
"Chinese Application Serial No. 202080052919.9, Office Action mailed Jul. 18, 2024", W English Translation, 14 pgs.
"Japanese Application Serial No. 2021-570982, Response filed Aug. 5, 2024 to Notification of Reasons for Refusal mailed Feb. 6, 2024", W English Claims, 12 pgs.
"Japanese Application Serial No. 2021-570966, Response filed Aug. 6, 2024 to Notification of Reasons for Refusal mailed Feb. 6, 2024", w current English claims, 16 pgs.
"European Application Serial No. 20813297.7, Response Filed Jul. 4, 2024 to Communication Pursuant to Article 94(3) EPC mailed Mar. 5, 2024", 146 pgs.
"U.S. Appl. No. 16/887,093, Final Office Action mailed Aug. 22, 2024", 41 pgs.
"Chinese Application Serial No. 202080055625.1, Request for Reexamination filed Aug. 26, 2024", w English Claims, 66 pgs.
"European Application Serial No. 20812964.3, Response filed Jul. 1, 2024 to Communication Pursuant to Article 94(3) EPC mailed Mar. 5, 2024", 145 pgs.
"Chinese Application Serial No. 202080052919.9, Response filed Sep. 18, 2024 to Office Action mailed Jul. 18, 2024", With English claims, 65 pgs.
"Japanese Application Serial No. 2021-570966, Examiners Decision of Final Refusal mailed Oct. 1, 2024", With English Machine Translation, 24 pgs.
"Japanese Application Serial No. 2021-571019, Examiners Decision of Final Refusal mailed Oct. 1, 2024", With English Machine Translation, 8 pgs.
"Japanese Application Serial No. 2021-570982, Examiners Decision of Final Refusal mailed Oct. 1, 2024", With English Machine Translation, 10 pgs.
"Chinese Application Serial No. 202080052919.9, Office Action mailed Oct. 1, 2024", With English Machine Translation, 11 pgs.
"Korean Application Serial No. 10-2021-7043309, Notice of Preliminary Rejection mailed Oct. 18, 2024", W English Translation, 6 pgs.
"Korean Application Serial No. 10-2021-7043307, Notice of Preliminary Rejection mailed Oct. 25, 2024", W English Translation, 18 pgs.

(56) References Cited

OTHER PUBLICATIONS

"Korean Application Serial No. 10-2021-7043308, Notice of Preliminary Rejection mailed Oct. 18, 2024", W English Translation, 25 pgs.

* cited by examiner

ADAPTIVE SUPPORT APPAREL SYSTEMS AND METHODS

PRIORITY APPLICATIONS

This application is a continuation of U.S. patent application Ser. No. 16/887,118, filed May 29, 2020, issued as U.S. Pat. No. 11,832,657, which application claims the benefit of priority to U.S. Provisional Patent Application Ser. No. 62/855,712, filed May 31, 2019, the contents of both which are incorporated by reference herein in their entireties. This application is also related to U.S. patent application Ser. No. 16/887,093, filed May 29, 2020 and issued as U.S. Pat. No. 11,825,886 as well as U.S. patent Ser. No. 16/887,093, filed May 29, 2020, and U.S. patent Ser. No. 18/143,043, filed May 3, 2023.

The following specification describes various examples of adaptive support apparel as well as various aspects of lacing systems utilized within the adaptive support apparel. For example, various adaptive mechanisms both manual and automatic including a motorized lacing system, motorized and non-motorized lacing engines, lacing/strap components related to the lacing engines, and automated lacing apparel platforms are disclosed.

BACKGROUND

Apparel, such as bras, tops, bottoms, tights, leggings, underwear, etc. can be constructed to provide support to a wearer during various activities Such apparel may include minimal adjustments for size, body type, activity preferences, among other things and may have limited adjustment or adaptability.

OVERVIEW

The present inventors have recognized, among other things, a need for improved fit and function of support apparel, such as bras, tights, and various other garments, undergarments, or baselayers (also referred to herein as support garments). One example piece of apparel is an adaptive bra that can custom fit to individual body contours and automatically or manually adjust to different dynamic conditions (e.g., changes in activity level). For example, an adaptive bra can adjust from maximum comfort to maximum breast support as a wearer transitions from resting to strenuous exercise. An adaptive bra can also utilize automated adjustment mechanisms coupled to movement sensors to dynamically adjust to inhibit unwanted movement of the breasts during activities, such as running as an example. Adaptive apparel, such as adaptive tights discussed below, can also provide dynamic support with the potential to enhance performance or reduce potential for injury. Adjustable compression sleeves can assist with recovery or support anatomy during certain activities. Numerous examples of the various support apparel introduced here are discussed throughout the following disclosure.

The discussed adaptive support apparel can include support mechanisms, such as lacing, straps, lace guides, and automated/semi-automated/manual tightening engines (also discussed as lacing engines or adaptive engines). The lacing can include intricate patterns of thin cord strung through various portions of the adaptive apparel item to enable select regions of the apparel to be tightened or loosened in accordance with the desired outcome. The lacing can include yarns, brio cables, or similar structures integrated during the manufacturing (e.g., knitting) process. For example, dedicated yarns or brio cables can be knit into key areas of an adaptive garment and routed external to the garment to interface with other lacing structures and/or adaptive engines to facilitate adjustments. The application uses the term "lacing" broadly to cover a wide variety of materials and structures used to create adaptive support structures within an adaptive support garment. The lacing can function as an adaptive support structure that operates to change the relative position of various portions of the adaptive support apparel. The thin cord or yarn can be either elastic or inelastic depending on the particular region and desired outcome. Elastic cord can provide a tightening effect over a broader region, while inelastic lacing can transmit a pulling force to a more specific region. Strap material (e.g. webbing or knit material with some width dimension) can be utilized selectively to better distribute pulling forces and potentially increase comfort. In certain examples, lacing may couple in one or more places to straps via fixed connections or lace guide type connections. Lace guides can include pivots, eyelets, tube structures, and textile-based tunnels, among other structures to guide lacing through the adaptive apparel to create the desire support structure.

The term "support garment" as used herein is meant to encompass any number of support garments such as bras, sport bras, tank tops, camisoles with built-in support, swimming suit tops, body suits, baselayers, and other styles or types of support garments used to support body tissue (e.g., breast tissue). Support garments can also include underwear, tights, leggings, baselayers (e.g., tight-fitting tops or bottoms), sleeves, and athletic supporters, among other things. Further, the term "breast contacting surface" as used herein is meant to encompass any type of structure that is in contact with or intended to be positioned adjacent to the wearer's breasts when the support garment is worn. In example aspects, and for a typical wearer, a support garment comprises a first breast contacting surface configured to contact or be positioned adjacent to, for instance, a wearer's right breast and a second breast contacting surface configured to contact or be positioned adjacent to, for instance, a wearer's left breast. In example aspects, the support garment comprises separate distinct cups (molded or unmolded) with each cup comprising a breast contacting surface and with each cup configured to cover or encapsulate a separate breast, or the support garment may comprise a unitary or continuous band of material that makes contact with both of the wearer's breasts. Any and all aspects, and any variation thereof, are contemplated as being within aspects herein. While the majority of the examples involve adaptive bras, the principals can be applied to various other support garments including compression tights, compression sleeves, and even athletic supporters (commonly referred to as a jockstrap).

The present inventors have also recognized, among other things, a need for dynamically modifying the support provided by certain types of support apparel based on a change in activity level. The need for modifying the support stems from both a long-term comfort and needed improvements in functionality during activities. Accordingly, a system has been developed including activity sensors, such as inertial measurement units (IMUs), global positioning sensors (GPS) or heart rate monitors among others, communicating with a control circuit that sends commands to an adaptive support apparel including an adaptive engine to facilitate automatic changes in support based on changes in detected activity levels. These systems can provide a wearer all-day comfort without compromising performance orientated support. Prior to integration of a complete system, a wearer would either need to change support apparel for different activities or struggle with multiple manual adjustments.

The activity sensors discussed herein can include any sensor that provides an indication of a level of physical activity of a user, as well as any sensor that provides an indication of forces (dynamic or static) imparted on an adaptive support garment during use. Sensors can be embedded into an adaptive support garment to provide data related to forces imparted on portions of a support structure, such as straps, laces, cables, or regions of fabric. Specific sensors, such as strain gauges or stretch capacitive sensors are discussed below.

The following examples of adaptive support apparel will further outline how the various structures can be utilized to deliver dynamically adaptable support apparel. The disclosed concepts can be used in additional apparel items not specifically discussed to perform similar support functions.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

The headings provided herein are merely for convenience and do not necessarily affect the scope or meaning of the terms used.

DETAILED DESCRIPTION

As noted above, various examples of adaptive support apparel have been developed with a range of manual and automated mechanisms to enable the adaptivity. Examples discussed in detail include adaptive bras, adaptive tights, and compression sleeves, among others.

Adaptive Support Apparel Systems

An adaptive support apparel system dynamically alters the fit and support of an adaptive support garment (e.g., bra or tights) in response to activity data obtained from an activity sensor worn by the user. The adaptive support system can include components integrated into various wearables, such as footwear, watches or support apparel. In certain examples, the adaptive support system can be controlled through a smartphone, smart watch, or similar wearable computing device that communicates wirelessly with other components of the system. In other examples, the adaptive support system is controlled with circuitry built into the components integrated into the adaptive support apparel and/or footwear. The following figures illustrate an example system and discusses at least some variations envisioned by the inventors.

Figure 1A:
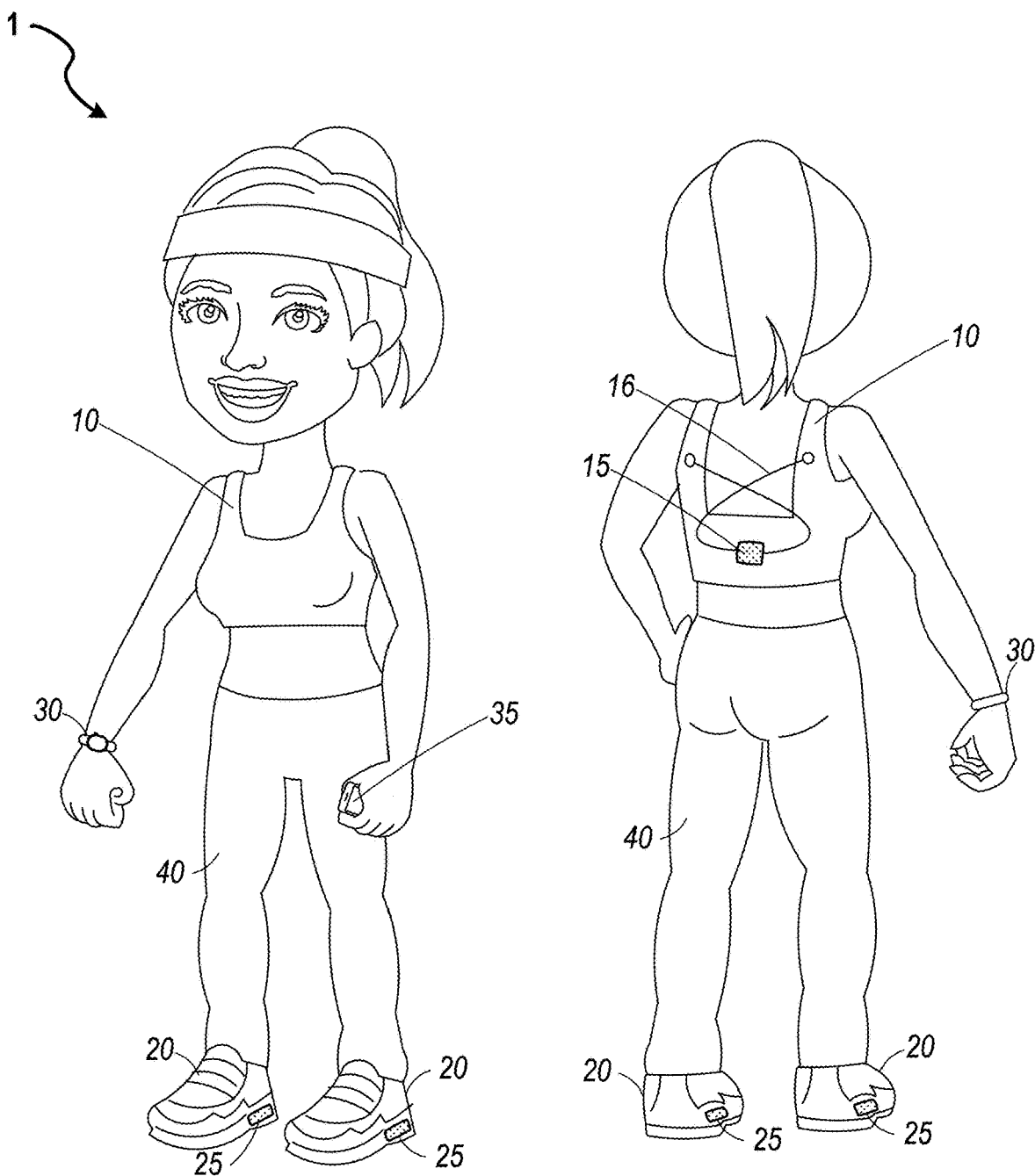
FIG. 1A-1B are illustrations of a system including an adaptive support garment and associated electronics, according to some example embodiments.
Figure 1B:
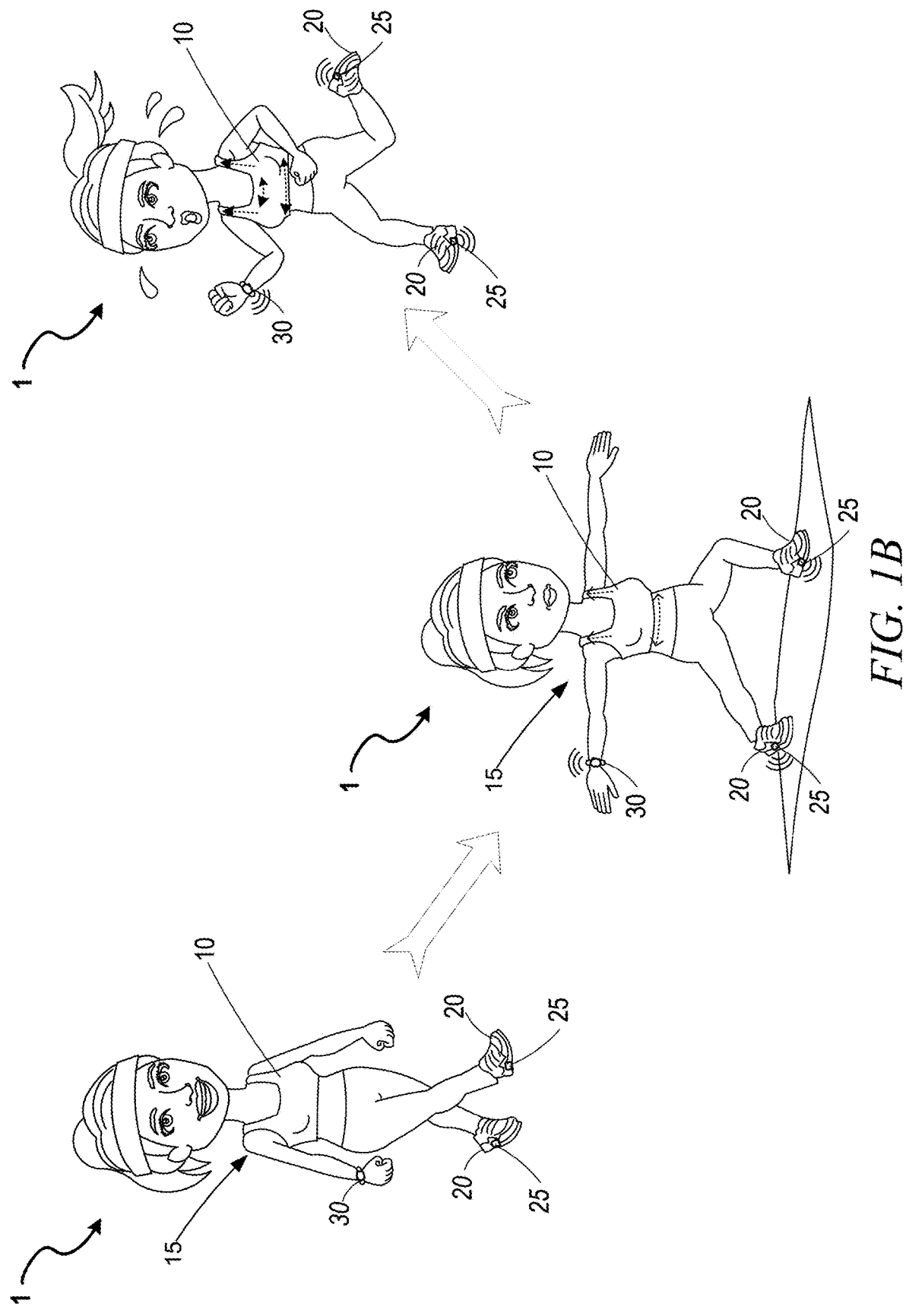

FIG. 1A-1B are illustrations of a system including an adaptive support garment and associated electronics, according to some example embodiments. In this example, the adaptive support apparel system 1 includes components such as, an adaptive support garment 10, a footwear assembly 20, and a smart watch 30. Optionally, the adaptive support apparel system 1 can also communicate with a smartphone 35 for control or adjustment of parameters. In this example, the footwear assembly 20 includes an activity sensor 25, and the adaptive support garment 10 includes an adaptive engine 15. In this example, the adaptive engine 15 couples to a lacing system 16 (also referred to as an adaptive support structure 16) that controls an adaptive support structure within the adaptive support garment 10. Optionally, the system 1 can also integrate a second adaptive support garment 40, illustrated here as adaptive tights.

In this example, the footwear assembly 20 includes an activity sensor 25 that can include sensors such as an accelerometer, a gyroscope, a magnetometer, a heart rate sensor, or a global positioning sensor (GPS) to detect a change in activity level. In one example, the footwear assembly 20 includes an inertial measurement unit (IMU), which combines at least accelerometers and gyroscopes to provide a specific force, orientation, or angular rate of change for a monitored body. Data from the IMU can be used to detect movements, such as foot strike or cadence among other things. In this example, the data from the activity sensor 25 is communicated to the smart watch 30 or smartphone 35 for processing to determine whether a change in adaptive support is needed based on the activity data from the activity sensor. In another example, the activity data base be sent directly to the adaptive engine 15 for processing and determination of adaptive support level needed.

Foot strike data is just a portion of a broader array of step metrics that can be determined from sensors, such as activity sensor 25 (e.g., IMU and Force sensor combination). Step metrics can include individual steps or step count. A step can be defined for this metric based on parameters such as, minimum vertical force threshold, minimum average vertical force per step, minimum step time and maximum step time. Step metrics can also include contact time, which is calculated per foot per step using a force single (e.g., time when vertical force>50N). Another step metric is swing time, which is calculated per foot per step using force single (e.g., time when vertical force<50N until that foot creates a force>50N). Step metrics also include cadence, which can be defined as the inverse of the sum of the contact and swing time for each foot using force signal. Step length is another step metric calculated using a force signal (e.g., sum of contact and swing time multiplied by average speed). Another step metric is impact, which can be calculated in at least two ways. Impact can be a peak rate of rise of the vertical ground reaction force, or an active peak of the vertical ground reaction force. Impulse is another step metric that is calculated per foot per step using a force signal (e.g., integral of the ground reaction force magnitude). Contact is another step metric derived from motion data. For example, using IMU data sampled at 200 Hz to determine foot angle relative to horizontal at the time of foot contact. Contact can include rearfoot, midfoot, and forefoot angles. Any of the step metrics discussed here can be used as activity data or in addition to other activity data to assist in determining an activity level or directly to determine a target support level for an adaptive support garment.

In this example, one or both of the smart watch 30 and smartphone 35, separately or in conjunction with one another or by accessing remote computing resources, includes a control circuit that processes the activity data and sends commands to the adaptive engine 15 to change support characteristics as needed. The adaptive engine 15 receives commands and activates a motorized system to adjust an adaptive support structure through interactions with an integrated lacing system coupled to the adaptive engine 15. Details of an example adaptive engine are provided below in reference to FIGS. 9A-9D.

FIG. 1B illustrates a user of an adaptive support apparel system transitioning between different activities that might require, or benefit from, various levels of support. In this example, the activity sensor 25, illustrated within the footwear assembly 20, operates to detect different activity levels ranging from a relaxed walk to moderate exertion doing yoga to more extreme impact and exertion involved in running. In this example, the activity sensor 25 transmits data to a control circuit in the smart watch 30, which is running an application that determines a current activity level based on the activity data interpreted from the sensor (s). In some examples, the smart watch 30 can also include activity sensors that also send activity data to the control circuit operating on the smart watch 30 to provide additional activity level information to inform a decision to increase or decrease the support provided by the adaptive support garment 10, such as an adaptive bra as in this example. For example, the smart watch 30 can include an integrated heart rate monitor that can be used as additional information related to activity level.

In the comfort zone, the adaptive apparel support system 1 detects low levels of physical activity that have been determined to correspond to a relaxed level of support required from an adaptive support garment. Accordingly, the control circuit commands the adaptive engine 15 to activate and adjust the adaptive support garment 10 to a comfort setting. The control application (e.g., application operating the control circuit) can include a user interface that provides a user access to different settings for the adaptive support garment. In an example, the settings can include associating different support levels with different pre-defined activity levels, such as resting=comfort support level (e.g., low level of support) and higher impact=performance support level (e.g., a high level of support). Other mappings can be created, and a user interface can be presented to allow a user to generate custom mappings, Table 1 illustrates an example mapping table for Activity Level-Support Level mapping.

TABLE 1

| Activity Level | Support Level |
|---|---|
| Resting (no exertion, no impact) | Comfort-Minimum Support |
| Walking (moderate exertion, low impact) | Recreation-Moderate Support |
| Yoga (moderate exertion & impact) | Sport-Enhanced Support |
| Running (high exertion & impact) | Performance-Superior Support |

As illustrated, a user can transition from Comfort to Lower Impact by increasing exertion and/or impact detected by the activity sensors. Dynamically, upon detecting a transition the control circuit in the smart watch 30 commands the adaptive engine 15 to increase the support level provided by the adaptive support garment 10. If the user reverts to a Comfort level of activity (e.g., resting or walking), then the control circuit can command the adaptive engine 15 to relax the support level back to a comfort level of support. Alternatively, if the user increases activity by going for a run, the system can dynamically respond with the adaptive engine 15 increasing the support level to a higher impact (performance) level of support.

In certain examples, a user can select from multiple different activity related parameters (e.g., heart rate, cadence, impact, etc . . . ) and associate different levels of each parameter with different support levels. For example, a user can create a running activity classification that uses heart rate and cadence as triggers. The running activity can then be mapped to a high support level. The support level can also be configured by associating different support structure adjustments to a particular support level, such as a lace tension for a lacing system-based support structure. A calibration and monitoring technique is also discussed below in reference to FIG. 1D, which is another mechanism to personalize the adaptive support garment.

Figure 1C:
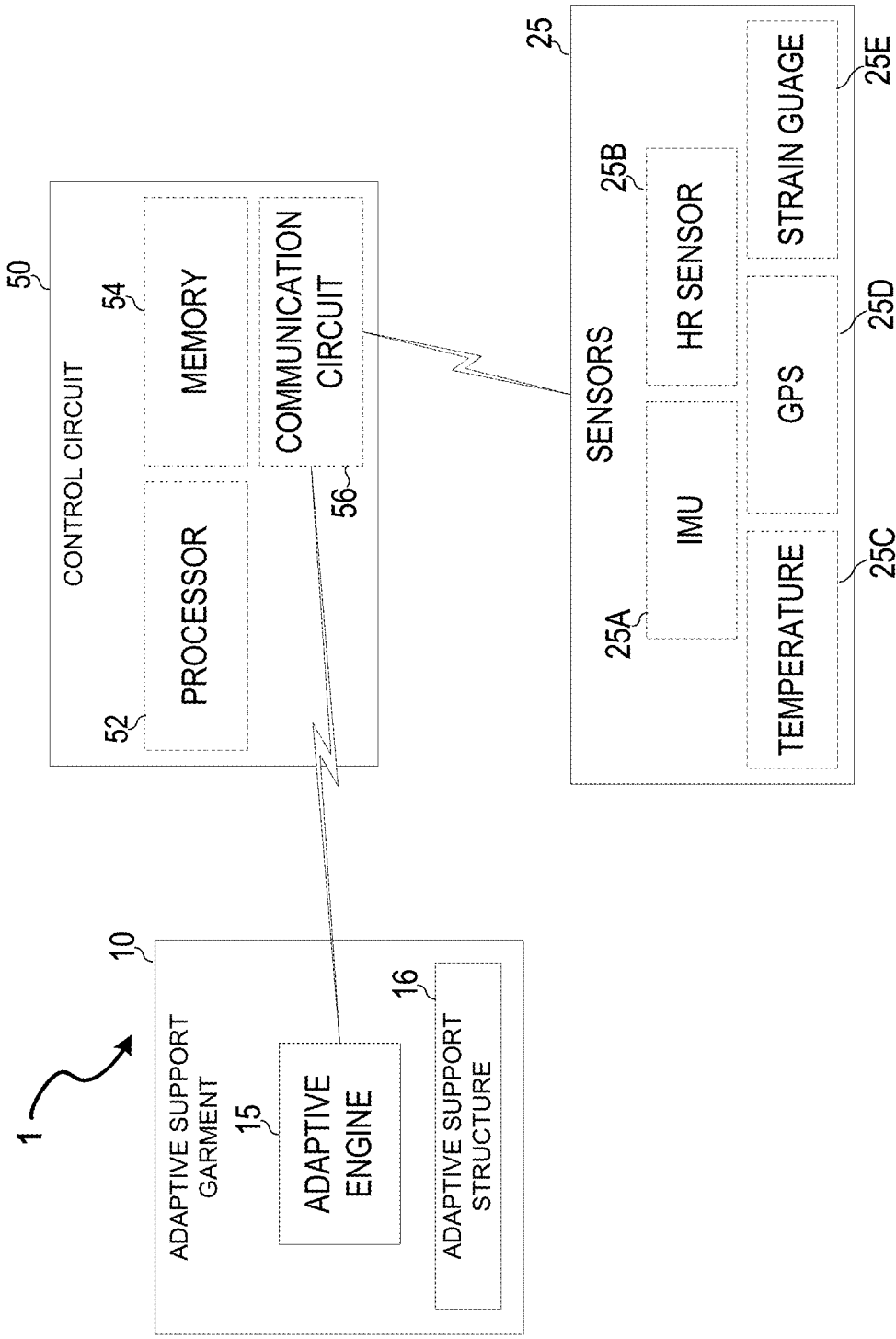
FIG. 1C is a block diagram illustrating components included in an adaptive support system, according to some example embodiments.

FIG. 1C is a block diagram illustrating components of the adaptive support system, according to some example embodiments. Note, throughout the application the adaptive support system is also referred to as the adaptive support apparel system. In this example, the adaptive support system 1 includes components such as a control circuit 50, activity sensors 25, and an adaptive engine 15, with the adaptive engine 15 integrated within an adaptive support garment 10. The adaptive support garment 10 can include an adaptive support structure 16. The adaptive support structure 16 includes one or more lace cables (or similar structure) routed around one or more lace guides to adjust at least a first portion of the adaptive support garment 10 in relationship to at least a second portion of the adaptive support garment 10. The lace cables and lace guides are also discussed herein as a lacing system.

The control circuit includes a processor 52, a computer-readable memory device 54, and a communication circuit 56. As discussed above, in some examples the control circuit 50 can be integrated within a smart watch 30 or smartphone 35 (FIG. 1A). In those examples, the control circuit 50 is embodied within a software application running on an operating system (e.g., iOS or Android) for the smart watch 30 or smartphone 35 hardware. Accordingly, the processor 52 and memory device 54 would be part of the smartphone 35 or smart watch 30. In the illustrated example, the control circuit 50 is a standalone device or integrated into a footwear assembly or the adaptive engine 15.

The processor 52 accesses instructions stored in the memory device 54 to process activity data received over the communication circuit 56. The activity data can also be stored on the memory device 54 at least during processing operations. The processor 52 also processes instructions that enable the processor 52 to generate and transmit, over the communication circuit 56, commands to the adaptive engine 15. The commands communicated to the adaptive engine 15 control activation of the adaptive engine 15 to change support characteristics of an adaptive support garment.

Figure 1D:
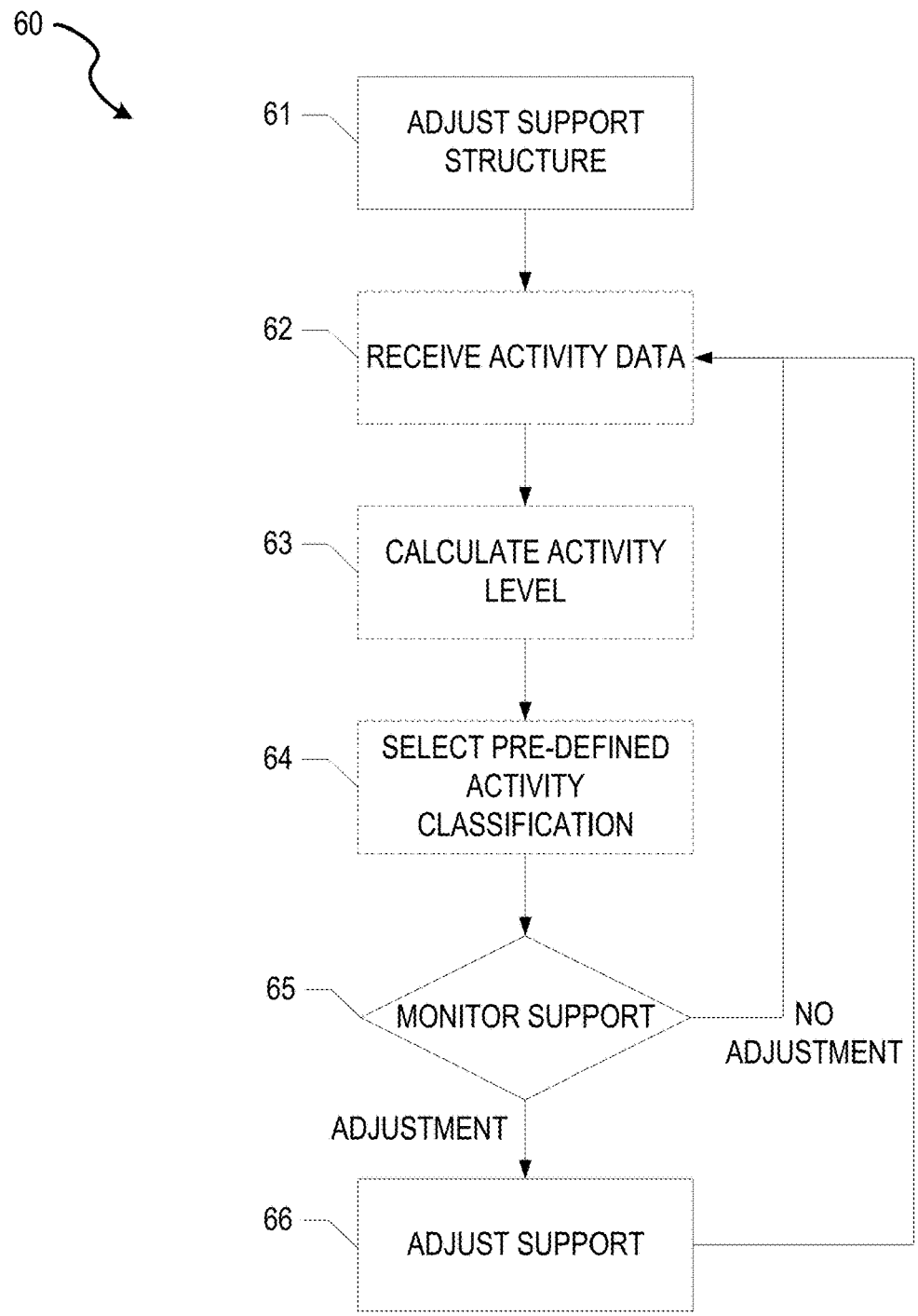
FIGS. 1D-1E are flowcharts illustrating techniques for dynamic adjustment of an adaptive support garments, according to some example embodiments.

The control circuit 50 receives activity data from activity sensor(s) 25. In this example, activity sensors 25 can include any combination of an IMU 25A, a Heart Rate (HR) Sensor 25B, a temperature sensor 25C, a GPS 25C, or a strain gauge 25D, among other sensors capable of producing data indicative of a user's activity level. The activity sensor 25 can include any combination of the listed sensors, and transmits the produced activity data to the control circuit 50 over a wireless communication link, such as Bluetooth® LE (Low Energy). The technique discussed below in reference to FIG. 1D provides additional details and context regarding the operations provided by the control circuit 50 and activity sensors 25. Additionally, as alluded to above, the components of system 1 discussed above can be distributed in any combination across devices including a smart watch, a smartphone, a footwear assembly, or an adaptive support garment (e.g., integrated into an adaptive engine).

FIG. 1D is a flowchart illustrating a technique 60 for dynamic adjustment of an adaptive support garment 10, according to some example embodiments. In this example, the technique 60 includes operations such as: adjusting a support structure at 61, monitoring support at 65 and automatically adjusting support at 66. Optionally, the technique 60 can also include operations such as: receiving activity data at 62, calculating an activity level at 63, and selecting a pre-defined activity classification at 64. The technique 60 covers operations performed by a combination of the control circuit 50, sensor(s) 25, and adaptive engine 15.

In this example, the technique 60 starts at 61 with an initial adjustment of a support structure 16 within an adaptive support garment 10. The initial adjustment can include both manual and automatic type adjustment, with automatic adjustment occurring in coordination with an adaptive engine 15. For example, the control circuit 50 can provide a user interface that allows a user to select an initial support level, such as relaxed. The control circuit 50 can then command the adaptive engine 15 to adjust the support structure 16 within the adaptive support garment 10 to a relaxed setting.

At 62 the technique 60 can optionally continue with the control circuit 50 receiving activity data from sensor(s) 25. The activity data can include physiological data, such as heart rate, as well as data descriptive of physical movements of portions of the anatomy of a user. At 63 the technique 60 can optionally continue with the control circuit 50 calculating an activity level based on the activity data received at 62. The technique 60 can optionally use the calculated activity level to select a pre-defined activity classification at 64. In another example, at 64 the technique 60 can optionally include providing a user interface to allow a user to select a pre-defined activity classification to activate a desired support level.

At 65 the technique continues with the control circuit 50 monitoring for changes in the support level. Changes in the support level can be triggered by indications in the activity data, by the calculated activity level, or by selection of a pre-defined activity classification that maps to a different support level than the current support level. If no change in support level of indicated, the technique 60 continues by looping back to operation 62.

If adjustment of the support level is indicated, technique 60 continues to operation 66 with the control circuit 50 commanding an adjustment in the support structure 16 of the adaptive support garment 10. In this example, the control circuit 50 sends adjustment commands to the adaptive engine 15. The adjustment commands are generated based on the selected pre-defined activity classification, the calculated activity level, and/or the activity data. After adjustment of support, the technique 60 loops back to operation 62 to continue monitoring for support level changes.

Figure 1E:
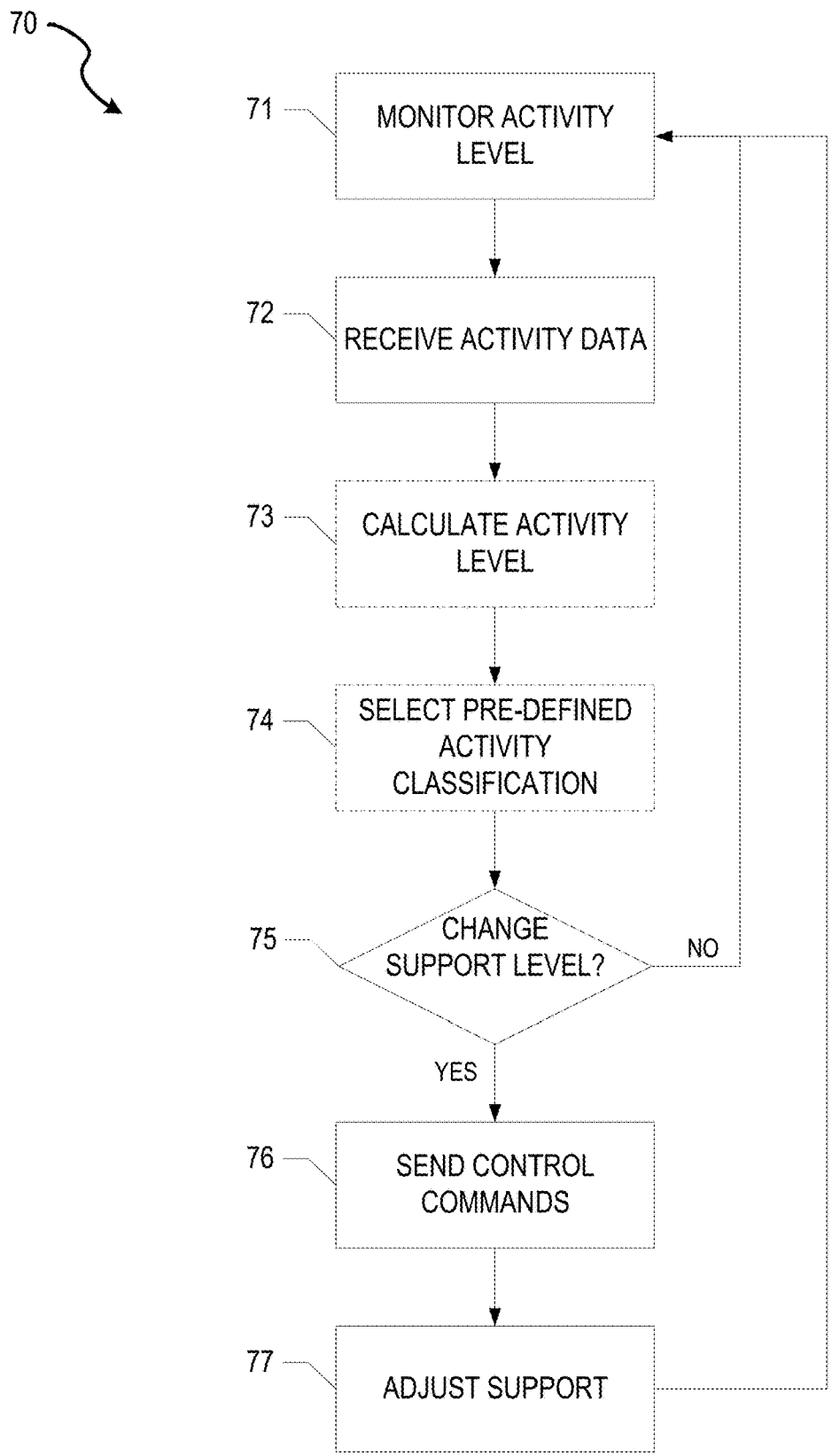

FIG. 1E is a flowchart illustrating a technique for dynamic adjustment of an adaptive support garment 10, according to some example embodiments. The technique 70 can include operations such as: monitoring activity levels at 71, receiving activity data at 72, determining a support level change at 75, sending control commands at 76, and adjusting support at 77. The technique also optionally includes calculating an activity level at 73 and selecting a pre-defined activity classification at 74. The technique 70 is discussed below operating on the system 1 discussed in reference to FIG. 1C, but the technique could be performed on any general-purpose computing device (e.g., a smartphone) in conjunction with the needed activity sensors and adaptive engine coupled to an adaptive support garment 10.

In this example, the technique 70 starts at 71 with the activity sensors 25 monitoring activity level. At 72 the technique 70 continues with the control circuit 50 receiving activity data over the communication circuit 56 from the activity sensors 25. In certain examples, the activity sensors 25 reside within a footwear assembly, such as footwear assembly 20, and communicate activity data to a control circuit 50 within an adaptive engine 15 over a Bluetooth LE wireless connection. In another example, the activity sensors 25 reside within a smart watch 30 and communicate through communication pathways within the operating system to an application also running on the smart watch that performs the functions of the control circuit 50.

At 73, the technique optionally continues with the control circuit 50 calculating an activity level based on the activity data received from the activity sensors 25. The technique optionally continues at 74 with the control circuit 50 selecting a pre-defined activity classification based on the calculated activity level. At 75, the technique continues with the control circuit 50 determining whether the support level of the adaptive support garment needs to be changed based on current calculated activity level. In some examples, the change in support level is determined based, at least in part, on the selected pre-defined activity classification. In other examples, the change in support level is determined at least in part on the calculated activity level. In yet other examples, the change in support level is determined based various combinations of the activity data received from the activity sensors 25, the calculated activity level, and/or the selected pre-defined activity classification.

If the control circuit 50 determines that the support level needs to be changed, then the technique 70 continues at 76 with the control circuit 50 sending commands to the adaptive engine 15 to change the support level of the adaptive support garment 10. The commands sent to the adaptive engine 15 can include commands to increase support or decrease support depending on whether the change requires additional support or less support. In certain examples, the adaptive support garment 10 can include multiple adaptive engines that control multiple support structures. In these examples, the control circuit 50 sends commands to control activation of all of the adaptive engines to achieve the desired support level. If the control circuit 50 determines that the support level does not need to be change, the technique 60 loops back to monitoring the activity level at 71.

At 77 the technique 70 completes a processing loop with the adaptive engine 15 adjusting the adaptive support garment 10 by manipulating a support structure 16 coupled to the adaptive engine 15 as appropriate to achieve the commanded support level. After adjustment of the support level, the technique 60 returns to monitoring the activity level at 71.

Figure 1F:
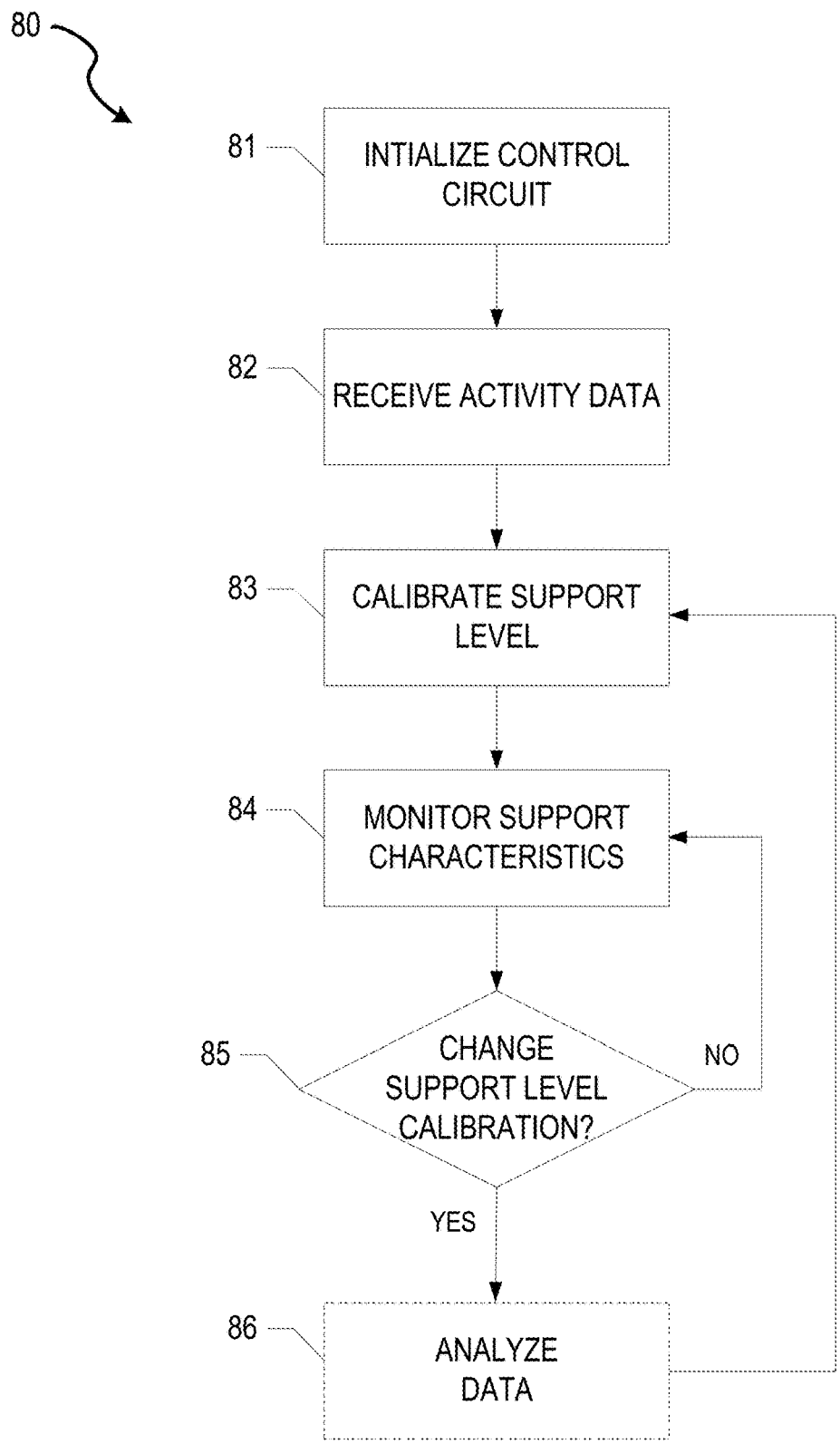
FIG. 1F is a flowchart illustrating a support level calibration and monitoring technique, according to some example embodiments.

FIG. 1F is a flowchart illustrating a support level calibration and monitoring technique 80, according to some example embodiments. The technique 80 outlines how an adaptive support garment 10 can be initially calibrated for a particular user and how the garment can adjust support levels over time based on monitoring activity levels and related parameters monitored on the adaptive support garment 10. In this example, the technique 80 includes operations such as: initializing a control circuit at 81, receiving activity data at 82, calibrating a support level at 83, monitoring support characteristics at 84, determine whether a change in support level calibration is needed at 85, and analyzing support characteristics data at 86. The technique 80 includes operations to initially calibrate an adaptive support garment for initial use by a user (operations 81-84) and operations to update support level calibration during use (operations 84-86). The second set of operations can include use of machine-learning or artificial intelligence algorithms to learn user preferences and update support level calibration on an adaptive support garment. The support level calibration adjusts pre-defined support levels to address unique physiology of individual users. For example, a user of an adaptive bra with C-size breast cups will utilize different adjustments of a support structure to attain certain support levels as compared to a user of an adaptive bra with DD-size breast cups. The calibration process can also adjust for use preferences, as some users may naturally appreciate more aggressive support as compared to another user with similar physical characteristics.

In this example, the technique 80 begins at 81 with a initializing a control circuit, such as control circuit 50, operating an adaptive support garment, such as support garment 10. Initializing the control circuit includes turning on the adaptive support garment and preparing the control circuit to operate the adaptive support garment. At 82, the technique 80 continues with the control circuit 50 receiving activity data, such as from sensor(s) 25. During initial calibration, a user is instructed to perform certain specific exercise or repetitive motions to assist with the calibrations. Data from performance of these specific movements are received by the control circuit at 82. At 83, the technique 80 continues with the control circuit 50 using the activity data generated performing the known physical movements to calibrate an initial support level for the user of the adaptive support garment. The known physical movements are select to invoke certain soft tissues supported by the adaptive support garment to be affected. Data collected characterizing this soft tissue movement is included in the activity data used to perform the calibration. For example, an adaptive bra can include sensors disposed within breast contacting surfaces and/or shoulder straps that can characterize movement of breast tissue during the known movements.

Once the initial calibration is completed at 83, the technique 80 can shift into monitoring/learning mode starting at 84. Operations 84 through 86 can stand alone as an ongoing monitoring/learning mode of operation of the adaptive support system 1. At 84, the technique 80 continues with the control circuit 50 monitoring support characteristics, which can include activity data as discussed above. At 85, the technique 80 continues with the control circuit determining whether the support level calibration needs to be updated based on the monitored support characteristics. If the support level calibration does not need to change, the technique 80 loops back to 84 to continue monitoring support characteristics. If the support level calibration does need to be changed, the technique 80 optionally continues to 86 to analyze the support characteristic data to facilitate updating the support level calibration. The technique 80 then continues by looping back to 83, and updating the calibrated support level based on the analysis.

Adaptive Bras

Depending on an activity experienced by a wearer of a bra (or other support garment), the desired fit of the bra may change. For example, during a sedate (relaxed) activity the wearer may prefer a bra that has less compression and tension than during an active activity. However, the wearer may not have an opportunity to exchange a first bra having a first fit for a second bra having a different fit at the time of changing an activity level. Further, the wearer may benefit from a bra that can adapt dynamically as the wearer transitions from activity to activity. Also, during different active activities the wearer may benefit from different types of additional support. Currently, a user of a bra may select a bra for one activity level regardless of the other states of activity to be experienced during the wearing period. This choice results in the selected bra not being a preferred selection for some activities.

Therefore, an adaptive bra that is adjustable while being worn to modify a fit characteristic based on user wants or needs provides benefits of varying levels of support increasing comfort levels across all activities. For example, a first fit of the bra may support a sedate activity that provides a comfortable fit that allows movement of breast tissue while provided gentle support. The bra may then be adjusted automatically in response to increased activity or by the wearer (e.g., manually) to a second fit that increases forces applied to the breast tissue in an effort to stabilize and secure the breast tissue during higher impact activities. For example, a wearer may have the bra in the first fit during travel to an athletic activity and the wearer may adjust the bra to the second fit when beginning the athletic activity. Following the athletic activity, the wearer may again change the fit of the bra back to the first fit. Breast tissue and surrounding soft tissues experience dramatic changes in movement between various activities, which can be measured as changes in magnitude of acceleration. Such measurements can be one input to a dynamic adaptive bra, such as those discussed herein. Note, breast tissue is used as an example above, but the adaptive support concepts are applicable to any body tissues that can benefit from increased support during certain activities.

An adaptive bra can include adjustability across the breast tissue at the breast contacting surfaces, between the breast contacting surfaces at a bridge, at the shoulder straps, at the wings, and/or along the back, among other places. Adjustability can include strap tightening-loosening, strap widening, gore (bridge) tightening, band tightening, encapsulation, and breast shaping, among others.

Figure 2A:
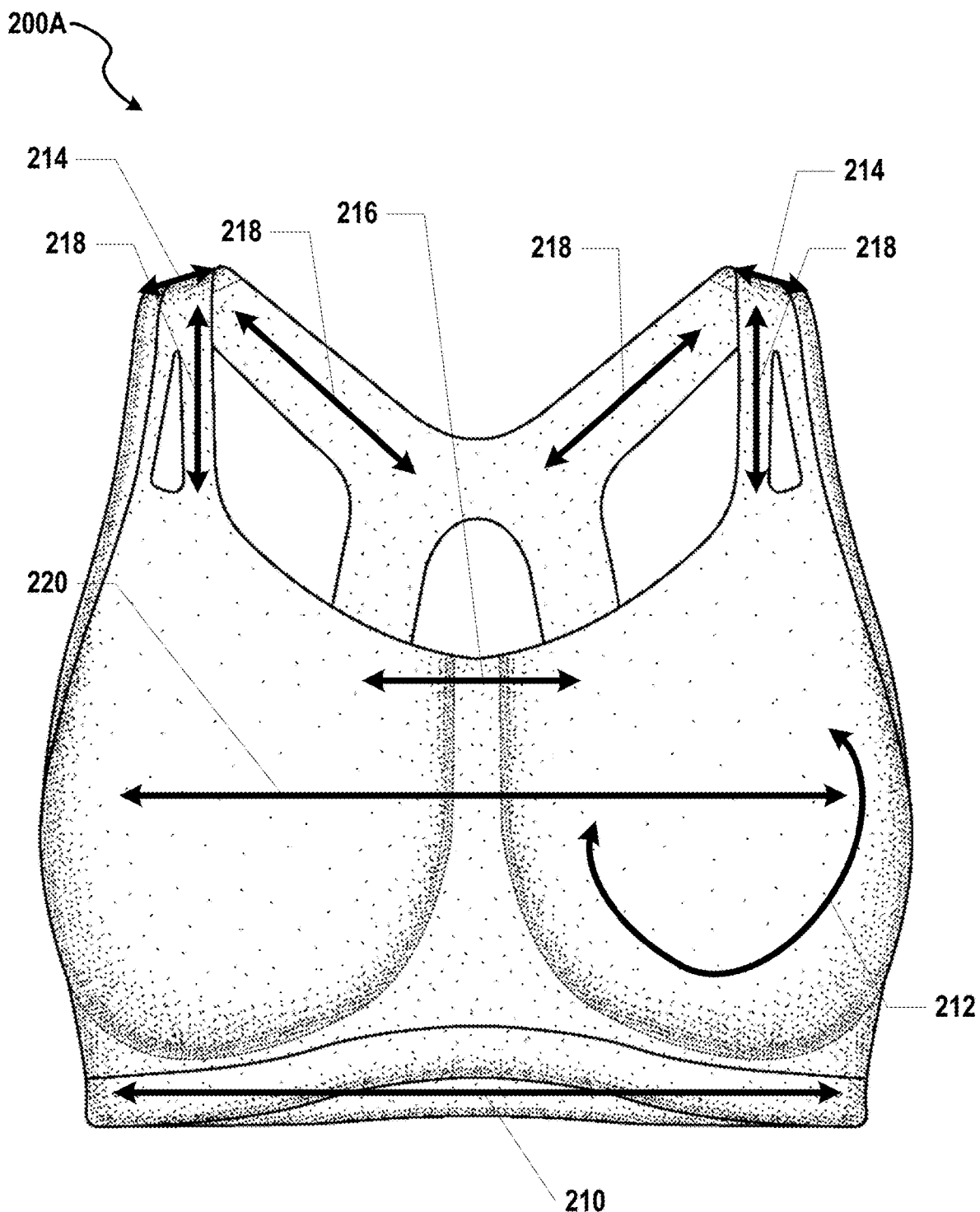
FIG. 2A is an illustration of adjustability zones for an adaptive bra, according to some example embodiments.

FIG. 2A is an illustration of adjustability zones for an adaptive bra, according to some example embodiments. Bra 200A, in this example, can include multiple adaptive zones. The adaptive zones can include under-band 210, breast contacting surface size 212, strap width 214, gore 216, strap length 218, and compression (wings) 220. In some examples, an additional adaptive zone can target breast shape (not specifically illustrated in FIG. 2A). The under-band 210 adjustment can include tightening or loosening to change under breast support and/or breast lift. In a traditional sports bra, up to 60% of the load of the wearer's breasts are carried by the under-band 210 around the rib region. The breast contacting surface size 212 adjustment can provide three-dimensional changes in the breast contacting surface size of the adaptive bra 200A, such as through dynamic padding systems or structured air pillows. Dynamic padding systems include those discussed in U.S. Patent Publication 2018/0140928, titled "Article of apparel with dynamic padding system", which is hereby incorporated by reference in its entirety. Adaptations in the breast contacting surface size 212 may also involve adjustments in shape. The strap width 214 adjustment can distribute loading on the bra straps over a wider area under certain conditions. In an example, the strap width 214 adjustment can be accomplished using auxetic material. Auxetics are structures or materials that have a negative Poisson's ratio. Auxetic material, when stretched, becomes thicker perpendicular to the applied force. The thickening occurs due to the internal structure resulting in the particular deformation when the sample is uniaxially loaded. Auxetics can be single molecules, crystals, or a particular structure of macroscopic matter. Auxetic materials and structures are expected to have mechanical properties such as high energy absorption and fracture resistance.

The gore 216 adjustment can adjust positioning of the breast contacting surfaces relative to each other providing for encapsulation or separation of the breasts. Strap length 218 adjustment zones are illustrated in multiple example locations, and provide for the ability to adjust lift and/or size-type fit adjustments. In a traditional sports bra, up to 40% of the load of the wearer's breasts are carried by the straps over the shoulders and into the back. The compression 220 adjustment allows for adjustment across the breast contacting material separate from the under-band 210. In some examples, compression adjustment is performed using posterior adjustment mechanisms (or adaptive support structures). Breast compression can be utilized to stabilize breast tissue during high impact activities, such as running. As illustrated above, a wearer of an adaptive bra benefits from adaptive support during a range of activities with varying degrees of impact, such as walking to yoga to running. Each distinct activity presents a different support challenge. For example, during yoga a wearer benefits from moderate support while allowing for extreme flexibility. In comparison, running requires maximum support while flexibility may not be critical.

Figure 2B:
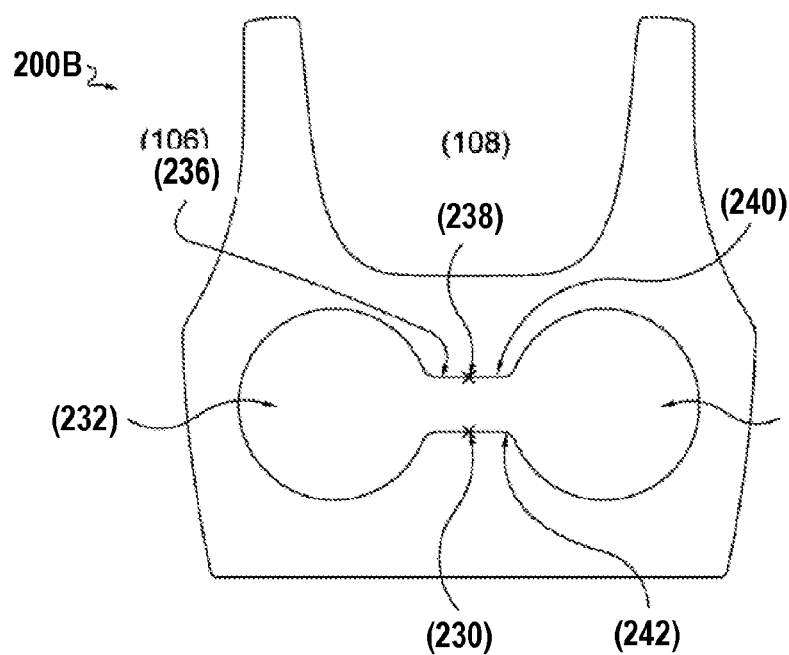
FIG. 2B is a diagram illustrating an adaptive bra, according to some example embodiments.

FIG. 2B is a diagram illustrating a suppression bra, according to some example embodiments. In this example, suppression bra 200B is an adaptive support garment (adaptive bra) that is adjustable by the wearer to adjust a degree of movement suppression of the breast tissue. In this example the adjustable suppression bra 200B includes a first breast contacting surface portion 232, a second breast contacting surface portion 234, and a bridge 236 extending between and joining the first breast contacting surface port and the second breast contacting surface portion. The first breast contacting surface portion 232, the second breast contacting surface portion 234, and the bridge 236 may be formed from a common material or a common collection of materials. For example, they may be formed from a relatively low stretch (e.g., relatively high modulus of elasticity) material to other portions of the bra. The modulus of elasticity is measured based on tensile stress relative to tensile strain along an axis of pull. When discussed herein, the axis of pull on a first material is parallel to an axis of pull in a second material when discussing a relative modulus of elasticity. For example, if a first portion has a lower modulus of elasticity than a second portion of the bra 200B, the pull axis for both the first portion and the second portion are parallel in the article as formed (e.g., both are vertical when the bra 200B is in an as-worn configuration by a traditional wearer).

In the suppression bra 200B, the bridge 236 has a superior portion 240 and an inferior portion 242. The suppression bra also includes an adjuster 246 (illustrated in FIG. 2C) extending between the bridge superior portion 238 and the bridge inferior portion 230. The adjuster 246 is adjustable between a first length and a shorter second length. The adjuster may be a trim piece (e.g., hardware having a buckle, rung, clasp, hook, or the like) that is joined with bra material, straps, or other elements (e.g., cord). Additionally, in some examples, the adjuster may be (or be coupled to) an adaptive engine that provides automatic or wearer activated adjustment.

Figure 2C:
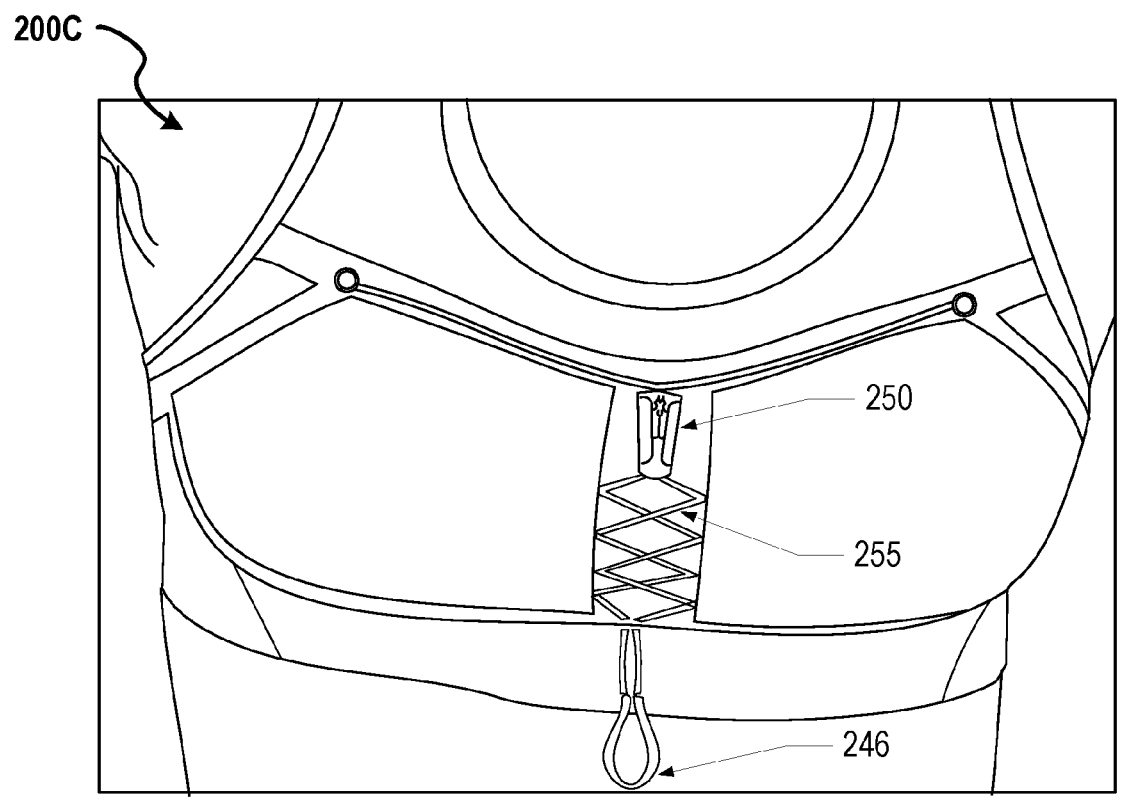
FIG. 2C is an illustration of an adaptive bra, according to some example embodiments.

The suppression bra 200B may suppress movement of breast tissue through an adjustment of the adjuster 246 (see FIG. 2C). For example, as the adjuster 246 decreases a distance between the superior portion 238 and the inferior portion 230, a bunching texture is created from the condensed materials. This shortening of the distance pulls the breast contacting surfaces in closer proximity that limits a volume of space the breast tissue can fill. This reduction in volume generates a compressive force on the breast tissue that translates to a movement suppression result when the wearer engages in physical activity.

Aspects herein describe material strata. A strata is a layer of material that may have different characteristics (e.g., physical, chemical, appearance) of other material strata. For example, a multi-layered knit material may have all layers contemporaneously knit, but one of the layers may have a different characteristic from the other layers (e.g., material or yarn selection, coloration, stitch technique, knit structure type, knit stitch sequence, etc.). Similarly, a laminate may be formed from two or more materials bonded together in a permanent manner, but each of the original materials forms a different strata within the laminate. Therefore, aspects hereof discuss a material strata, which refers to a layer, separable or not, from other layers. In an adjustable bra, a non-stretch material may be encased or layered between a first stretchable material body facing and a second stretchable material exterior facing. The term "non-stretch" is relative to the term "stretch." For example, the "non-stretch" material is less stretchy (e.g., has a higher modulus of elasticity) than the stretch material. The "non-stretch" material may elongate with sufficient force, but it will require more force or elongate less than the stretch material, in an exemplary aspect.

FIG. 2C is an illustration of an adaptive suppression bra, according to some example embodiments. The suppression bra 200C illustrated in FIG. 2C includes an adaptive engine 250, compression lacing 255, and a user activation cord (e.g. adjuster 246). The adjuster 246 can activate the adaptive engine 250, which can shorten the compression lacing 255 to activate the movement suppression of the suppression bra 200C. In some examples, the adaptive engine 250 can include an external release button that the wearer can activate to release tension on the compression lacing 255 and reduce the movement suppression.

Figure 3A:
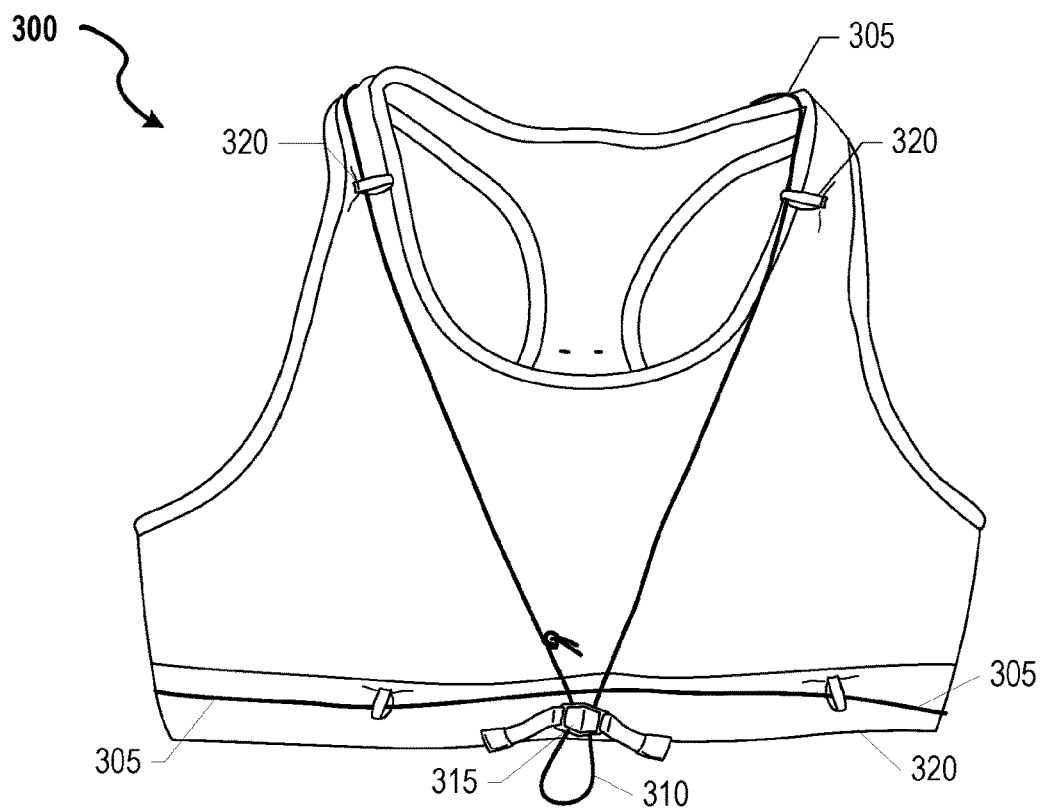
FIGS. 3A-3B are illustrations of an adaptive bra with a continuous support structure, according to some example embodiments.
Figure 3B:
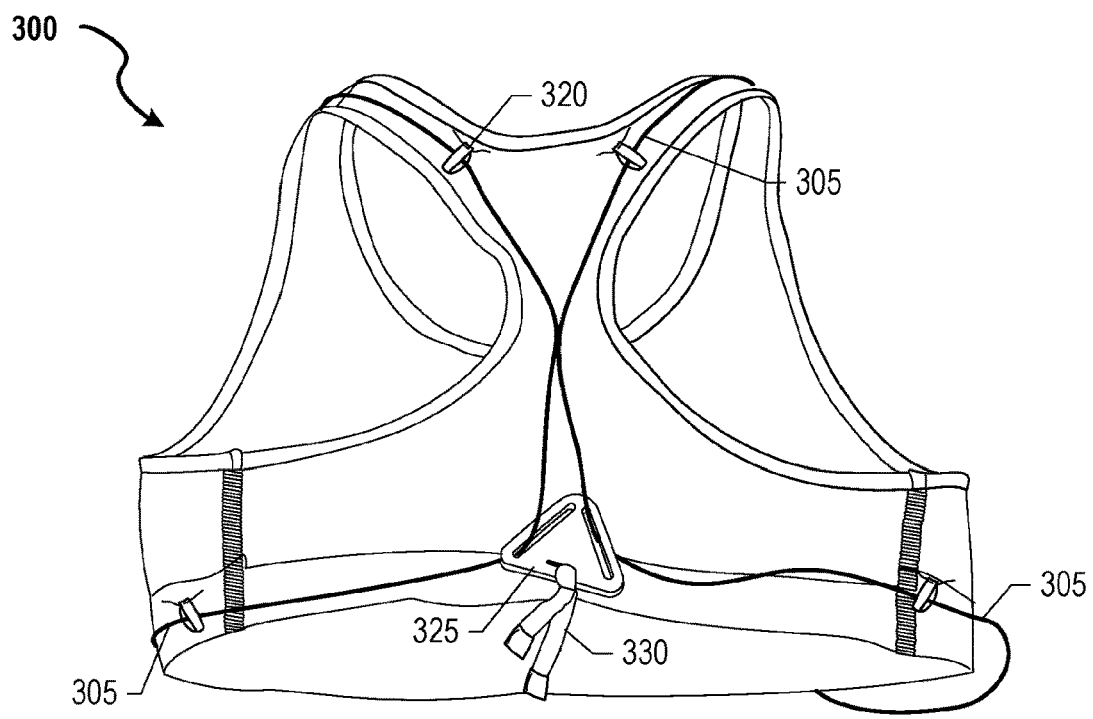

FIGS. 3A-3B are posterior illustrations of an adaptive bra 300 with a continuous support structure, according to some example embodiments. The adaptive bra 300 illustrates an example support structure (e.g., lacing 305) to provide adaptive support to the wearer. The adaptive bra 300 includes components such as lacing 305, manual pull 310, adjuster 315, guides 320, lace hub 325 and anchor tab 330. The adaptive bra 300 utilizes a continuous lacing 305 support structure that runs around an under-band, up between the breast contacting material, and over each shoulder strap. The lacing 305 is guided through the desired locations on the adaptive bra 300 by guides 320. The guides 320 can be fabric channels, tubing, or material tunnels that could extend along more significant portions of the lace path to improve support and comfort. In certain examples, the guides 320 are formed from knit components, such as knit component 350 discussed below in reference to FIG. 3C. The adaptive bra 300 includes a manual adjuster 315 that allows a wearer to activate adaptive support via the manual pull 310. As discussed further below, all of the support architectures illustrated in the various adaptive support garments can have automated adaptive engines integrated to enable fully or semi-automatic adjustability.

The adaptive bra 300 includes a lace hub 325 located along the under-band on the posterior side of the garment. The lace hub 325 routes the continuous lacing 305 coming down from the shoulders laterally around the under-band. The lace hub 325 is illustrated as a simple triangular slotted structure, but could also utilize small pulleys or fixed circular lace guides as example alternative structures. In some examples, the lace hub 325 could be replaced with a lacing engine to provide automatic or semi-automatic adjustments and lace routing. An example adaptive engine is discussed below in reference to FIGS. 9A-9E.

The lacing architecture illustrated on adaptive bra 300 can facilitate breast tissue isolation, under-band compression, and lift through shoulder strap compression forces.

Figure 3C:
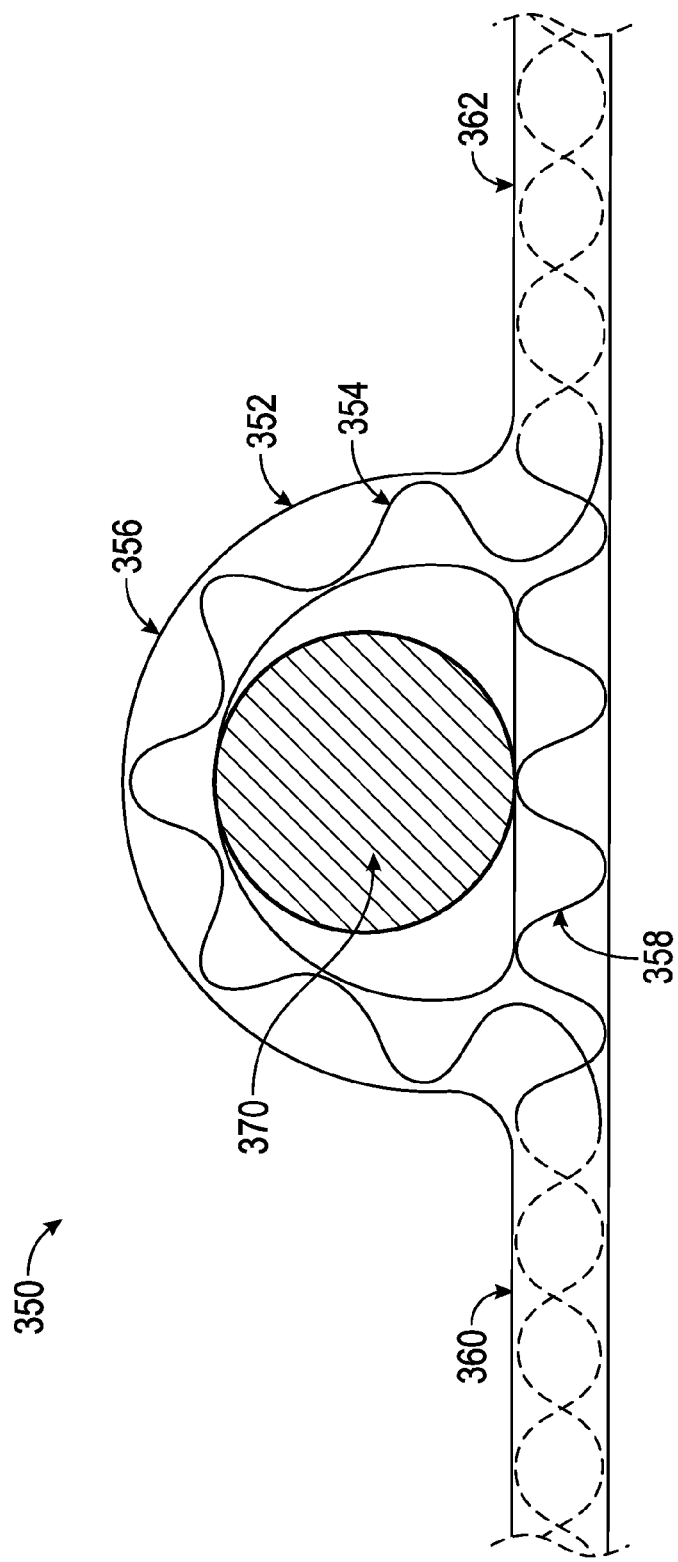
FIG. 3C is a line drawing illustration of a knit lace tunnel, according to some example embodiments.

FIG. 3C is a line drawing illustration depicting an example of a knit tube 352, where the knit tube 352 is formed by a multi-layer knit structure, such as a tubular knit structure. The tubular knit structure may be formed by any suitable tubular knitting technique, e.g., via weft-knitting techniques such as circular knitting or flat-knitting, or via a warp-knitting technique, etc. As one example, a tubular knitting process on a flat-knitting maching may comprise a first knit layer formed on a first bed of the knitting machine that remains separable from (e.g., having a central area not locked to) a second knit layer formed on a second needle bed for a plurality of courses. For example, referring the close-up view of one knit tube 352, a first layer 354 of the tube 352, which may define the exterior surface 356 of the knitted component 350, may be formed on a first needle bed of a knitting machine (e.g., with a single-jersey or similar knit structure). A second layer 358 of the knit tube 352, which may define an inner surface of the knitted component 350, may be formed on a second needle bed of the knitting machine (e.g., with a single-jersey or similar knit structure). The edges 360, 362 of the knit tube 352 (which extend along the tube's length) may be locations where a course at the end of the tubular knit structure (in the knitting direction) utilizes both needle beds, thus locking the first layer 354 and the second layer 358 together. In the resulting knitted component 350, a channel/tunnel may be formed between the first layer 354 and the second layer 358 of the knit tube 352, and that same channel may be used for receipt of the tensile strand (e.g., lace cable) 370.

The adaptive apparel discussed herein can utilize knit tubes, such as knit tube 352 to route lacing cables forming adaptive support structures through each garment. For example, any of the adaptive bras discussed above can include shoulder straps and under-band portions, among other portions, that include knit tubes to contain lace cables as part of an integrated adaptive support structure. All of the adaptive bra and tights examples discussed above could be constructed with at least a portion of the lacing systems contained within knit tube or channel structures similar to knit component 350 discussed here. Routing lace cables through knit components 350 provides aesthetic improvement by hiding the lacing system and also distributes forces from the lacing system to improve comfort and support for the wearer.

Figure 4A:
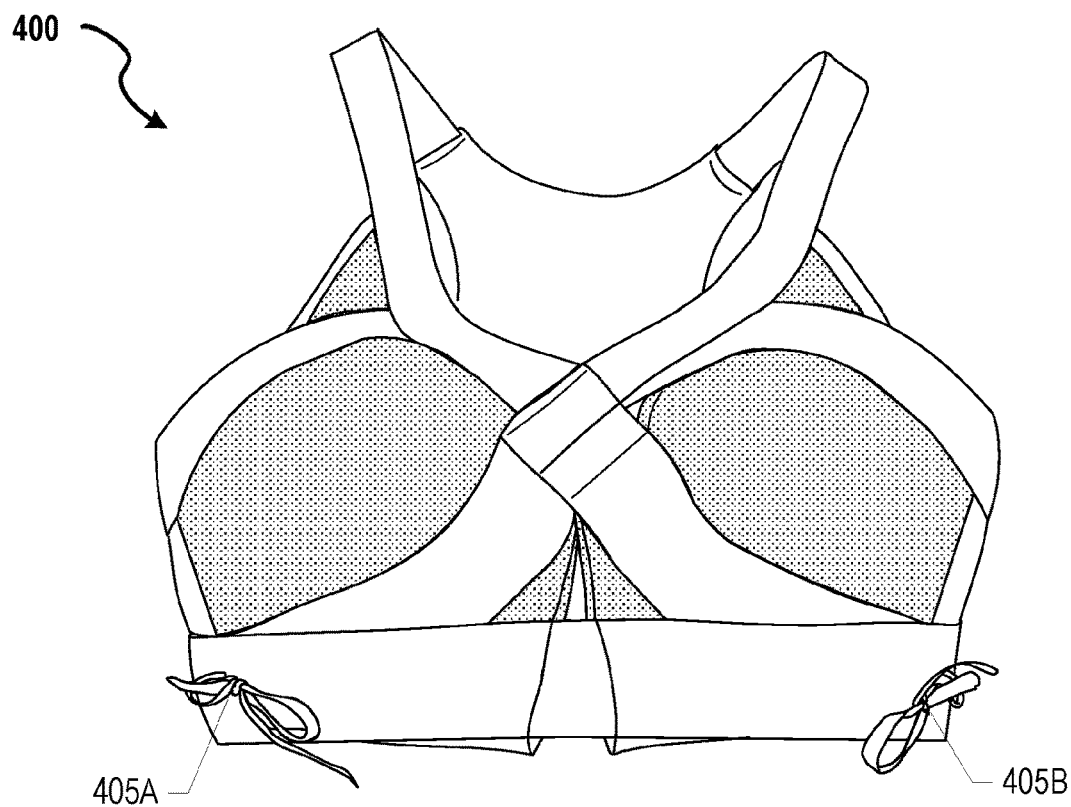
FIGS. 4A-4D are illustrations of an adaptive bra with crisscross posterior support lacing, according to some example embodiments.
Figure 4B:
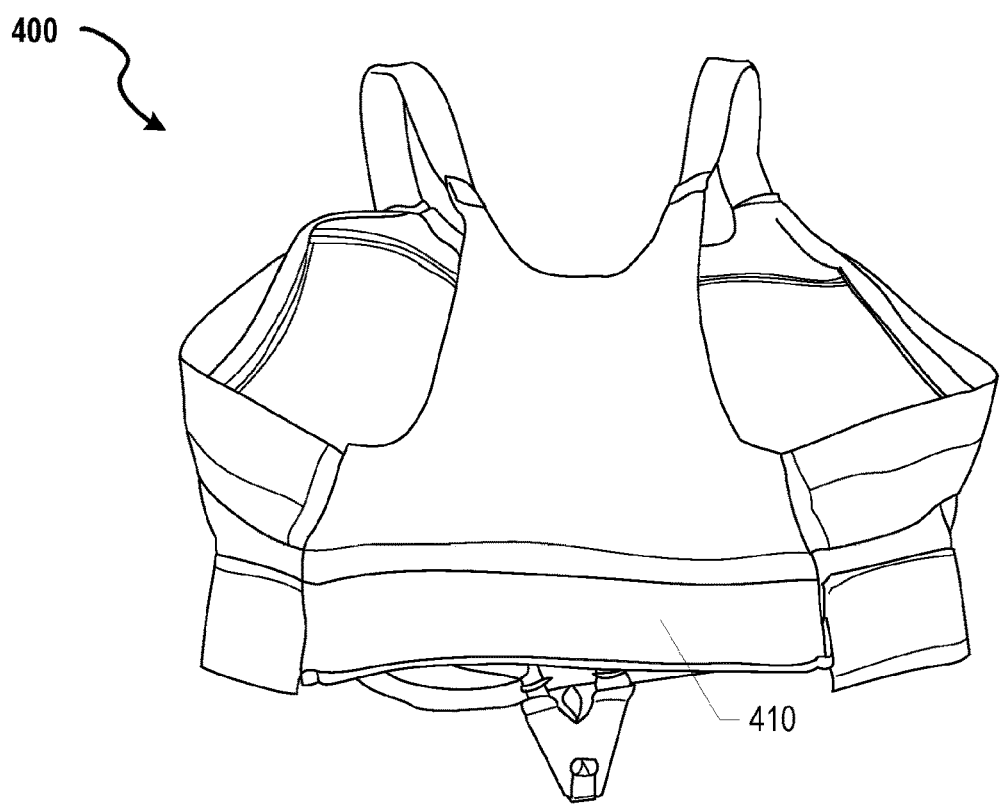
Figure 4C:
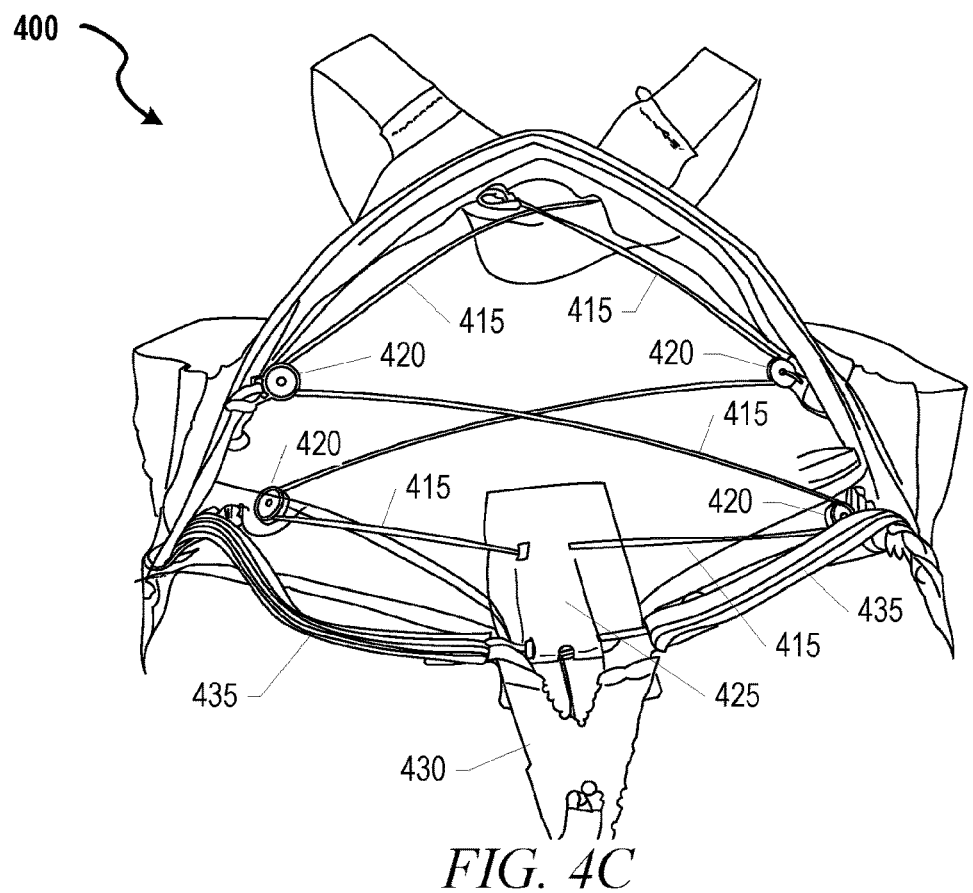
Figure 4D:
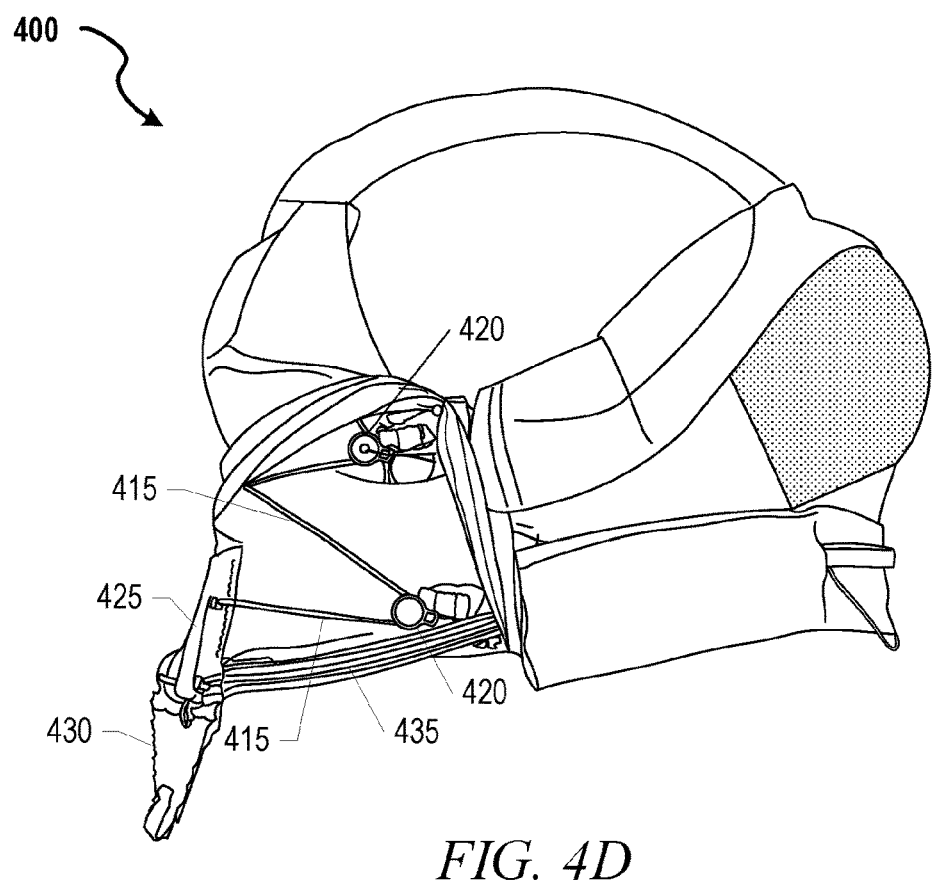

FIGS. 4A-4D are illustrations of an adaptive bra 400 with crisscross posterior support lacing, according to some example embodiments. The adaptive bra 400 provides illustration of another adaptive support structure including a right adjuster 405A and a left adjuster 405B, which could be replaced with an adaptive adjustment engine. The adaptive bra 400 also includes a posterior lacing cover 410 shown in FIG. 4B. FIGS. 4C and 4D illustrate the posterior adaptive support structure with the posterior lacing cover 410 pulled back. The posterior adaptive support structure includes lacing 415, lace pulleys 420, adjustment engine 425, adjuster 430, and under-band 435. In this example, the lacing 415 creates a crisscross pattern across the posterior portion of the adaptive bra 400 running from the adjustment engine 425 located along the under-band up to anchor points on the shoulder straps. The lacing 415 transverses through a series of lace pulleys 420 on either side of the adaptive bra 400. The lace pulleys 420 are anchored in locations to provide under-band and gore type adjustments. The posterior adaptive support structure also anchors on the shoulder straps to provide simultaneous lift support through the shoulder straps.

The adjustment mechanisms illustrated on the adaptive bra 400 include the right and left adjusters 405A, 405B, as well as the adaptive engine 425 along the posterior underband. The right/left adjusters 405A, 405B provide direct under-band adjustments, while the adaptive engine 425 tensions the posterior support structure via lacing 415. In this example, the adaptive engine 425 is manually activated via adjuster 430. In other examples, the adaptive engine 425 can be replaced with an automatic or semi-automatic adjustment engine to provide wearer or sensor activated automatic adjustments. In certain examples, an adjustment engine can be adapted to adjust both the lacing 415 and the under-band, which can eliminate the need for manual right/left adjusters 405A/405B. In some examples, multiple adaptive engines are used to provide separate automated adjustments of lacing 415 and right/left adjusters 405A/405B respectively.

Figure 5A:
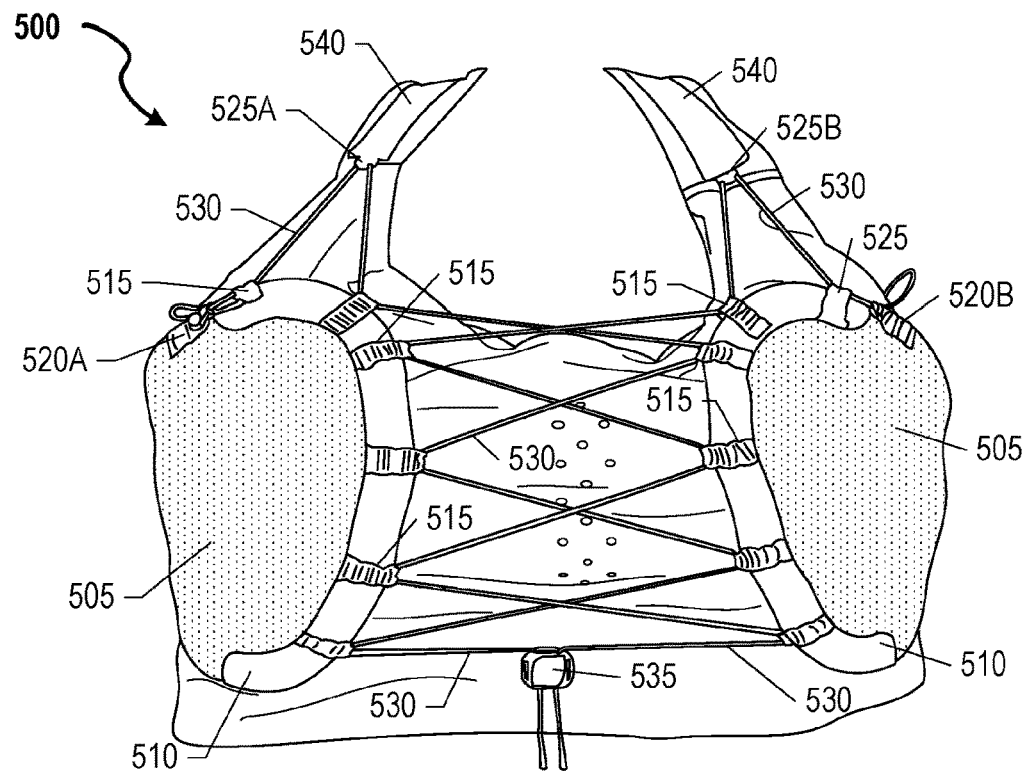
FIGS. 5A-5C are illustrations of an adaptive bra with crisscross gore support lacing and adaptive posterior straps, according to some example embodiments.
Figure 5B:
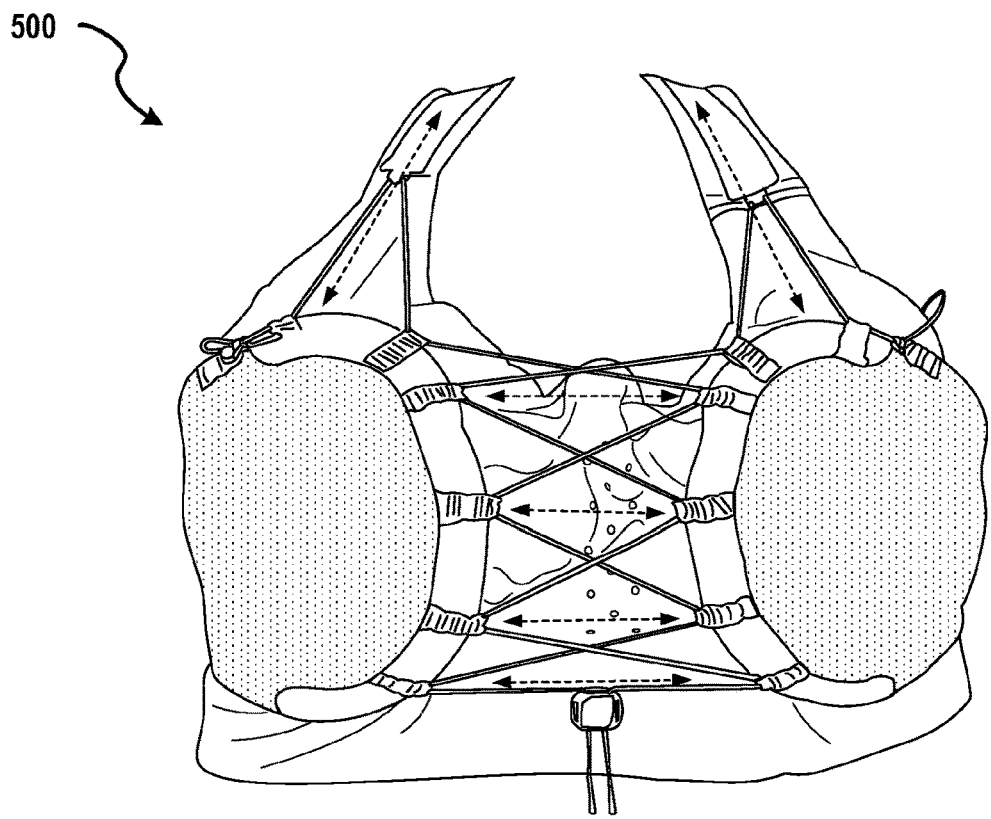
Figure 5C:
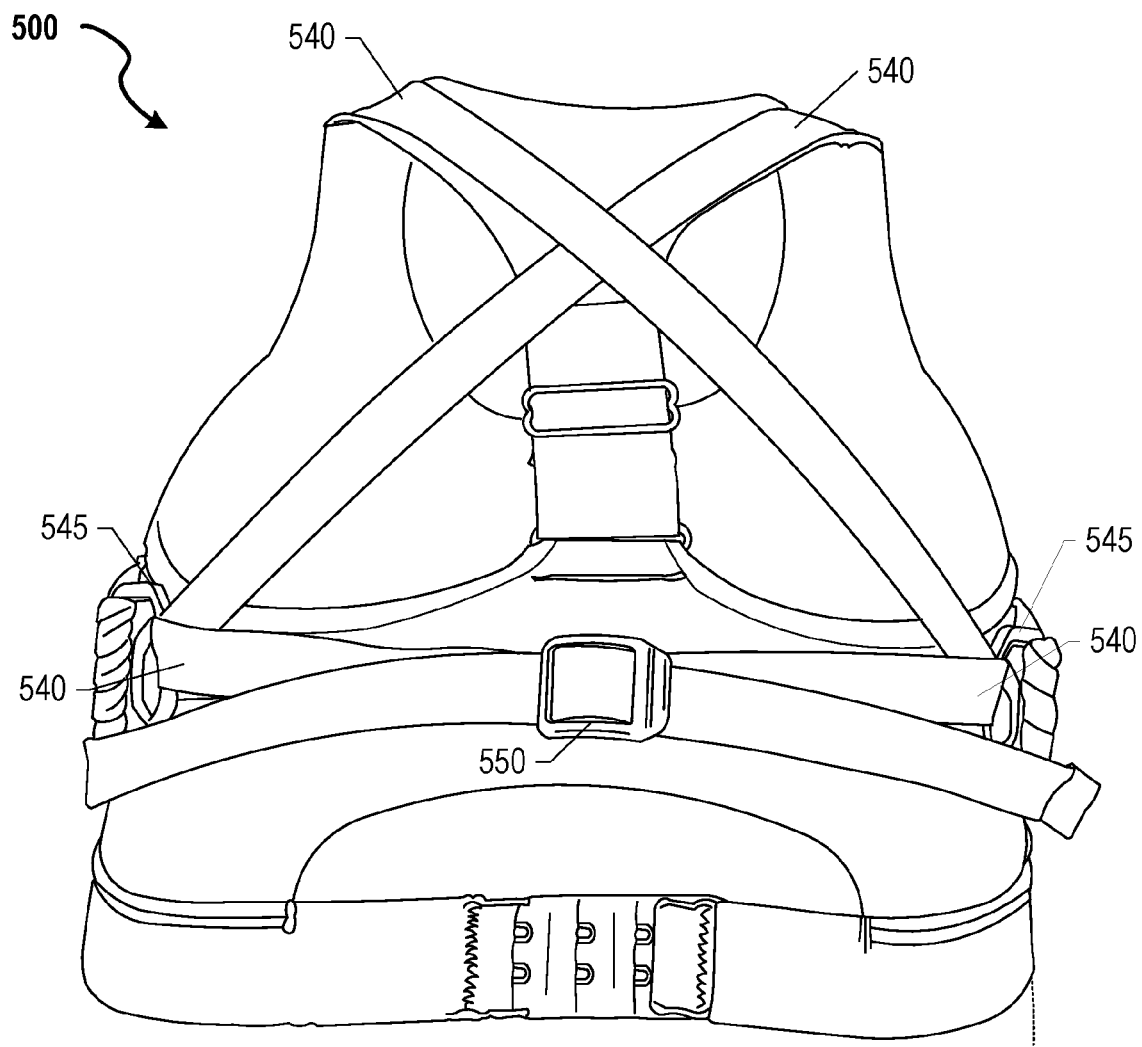

FIGS. 5A-5C are illustrations of an adaptive bra 500 with crisscross gore support lacing and adaptive posterior straps, according to some example embodiments. In this example, the adaptive bra 500 includes an anterior support structure in the form of crisscross lacing 530 to adjust breast contacting surfaces 505. The anterior support structure also includes central anchor overlay 510 supporting lace anchors 515 along medial portions of each breast contacting surface 505. The central anchor overlays 510 are formed from a stiffer material than the rest of the breast contacting surfaces 505 to assist in distributing the forces from the crisscross lacing 530. The lacing 530 is anchored on a lateral anchor 520A and a lateral anchor 520B, runs up to a right shoulder anchor 525A and a left shoulder anchor 525B. From the right/left shoulder anchors 525A, 525B the lacing 530 drops into the crisscross pattern created by lace anchors 515 distributed along a medial edge of the breast contacting surfaces 505. The anterior support structure is adjusted via adjuster 535, which in this example is a manual pull adjustment mechanism providing the ability to tension lacing 530 as illustrated in FIG. 5B.

As shown in FIG. 5B, the anterior support structure of adaptive bra 500 can generate gore tension as well as lift through the shoulder straps. In this example, the breast contacting surfaces 505 are essentially inelastic material that provides additional encapsulation and support of the breast tissue as the anterior support structure is tensioned (as illustrated in FIG. 5B). In another example, the central anchor overlay 510 is a stiff material designed to retain the desired shape and distribute loads, while the breast contacting surfaces 505 are a softer elastic material that provides support and comfort.

The posterior side of adaptive bra 500 is illustrated in FIG. 5C, and includes a support strap 540, strap adjustment 550 and under-band anchors 545. The strap adjustment 550 provides a separate initial adjustment mechanism to allow adaptive bra 500 to fit a wider range of sizes. As illustrated, the adaptive bra 500 also includes more traditional hook and loop closures along the under-band below the support strap 540.

Figure 6A:
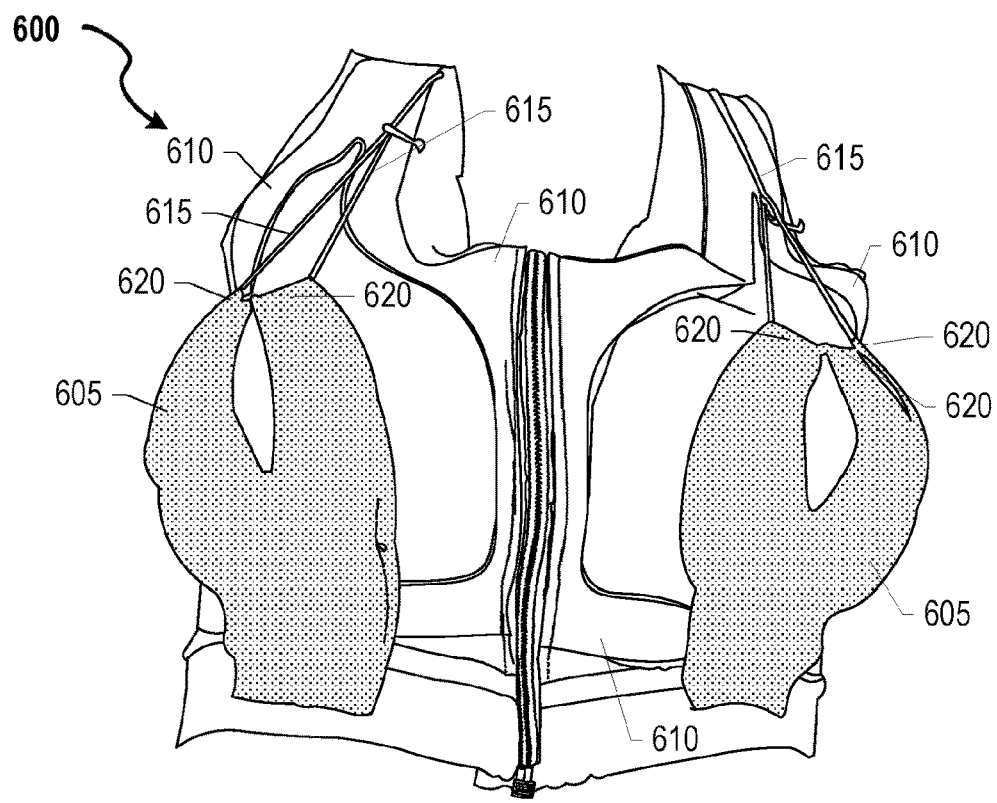
FIGS. 6A-6C are illustrations of an adaptive bra with adaptive breast contacting surfaces and posterior support lacing, according to some example embodiments.
Figure 6B:
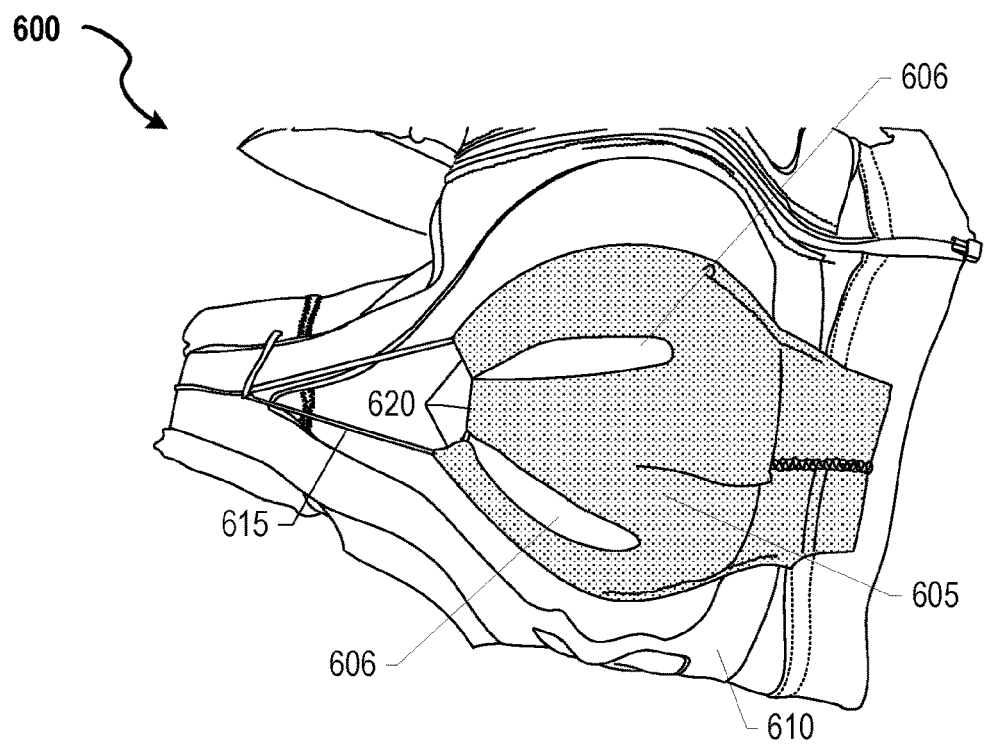
Figure 6C:
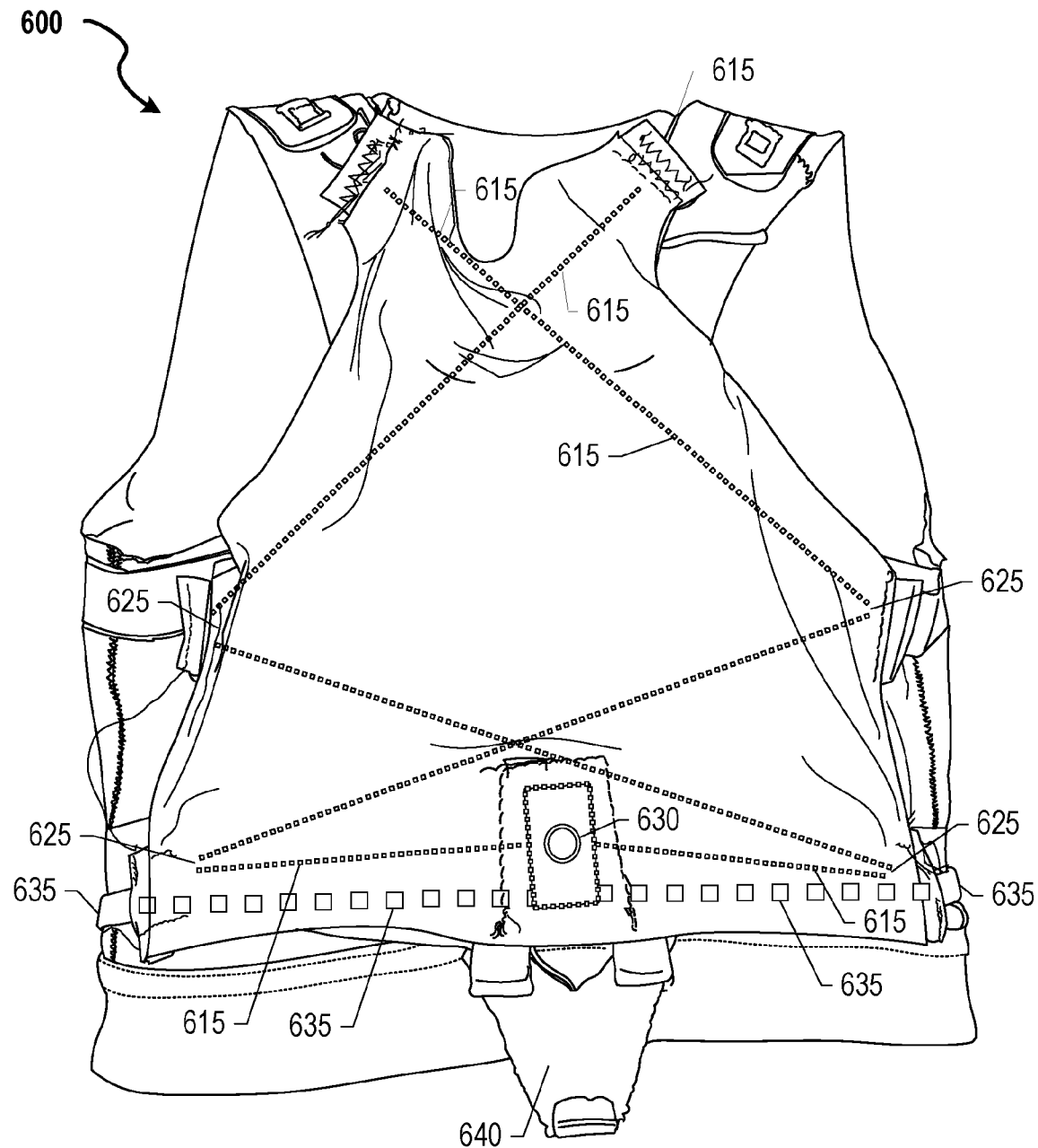

FIGS. 6A-6C are illustrations of an adaptive bra 600 with adaptive breast contacting surfaces and posterior support lacing, according to some example embodiments. In this example, the adaptive bra 600 includes adaptive support structures focused on breast shape and lift through anterior structures as well as gore and under-band tensioning through posterior structures. The anterior support structures include breast contacting surfaces 605, lacing 615, lace guides 620, with trim 610 providing dimensional structure around peripheral portions of the adaptive bra 600.

The breast contacting surfaces 605 can include a substantially inelastic (or at least less elastic as compared to surrounding non-support material) material contoured to provide specific breast tissue shaping as tension is applied to lacing 615. In this example, the contour includes two slots 606 formed in the superior portion of the breast contacting surface 605 that allows the material to wrap around the breast tissue and provide lift and some compression as tension is applied. The breast contacting surfaces 605 include three separated lace guides 615 on superior ends of the separated portions. In this example, lace guides 615 are formed with hemmed material creating material tunnels. In other examples, the lace guides can be plastic tubes with varying degrees of rigidity depending upon the desired shaping designed into the adaptive bra.

The posterior structures of the adaptive bra 600 are illustrated in FIG. 6C with hidden lines demonstrating where lacing 615, anchors 625, and under-band 635 are routed within the adaptive bra 600. As illustrated, the lacing 615 forming a crisscross structure extending down from the shoulder straps where the lacing 615 transverses from the anterior side. The crisscross pattern allows the adaptive engine 630 to provide tension to the under-band, gore, and anterior structure in unison. The posterior support structure can be activated via adjuster 640, which in this example is a pull tab. In other examples, the adjuster 640 can include tension and release buttons or separate pull tabs.

Figure 7A:
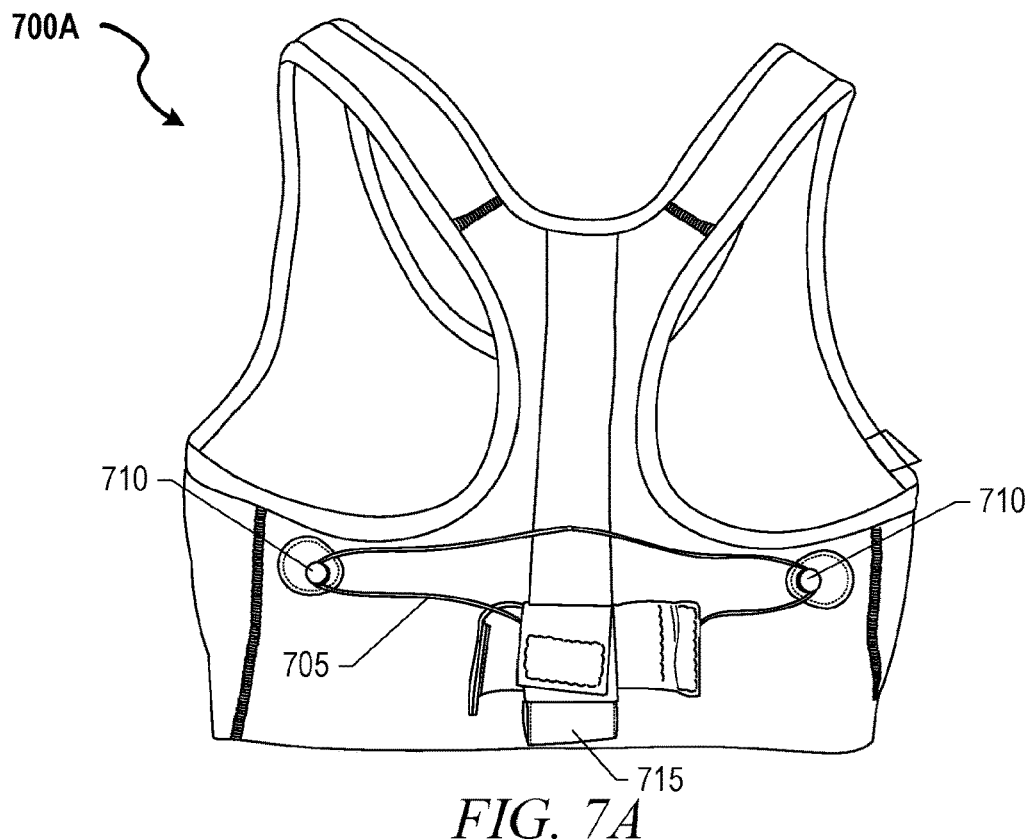
FIGS. 7A-7D are illustrations of various adaptive bra configurations with automated adjustment mechanisms, according to some example embodiments.
Figure 7B:
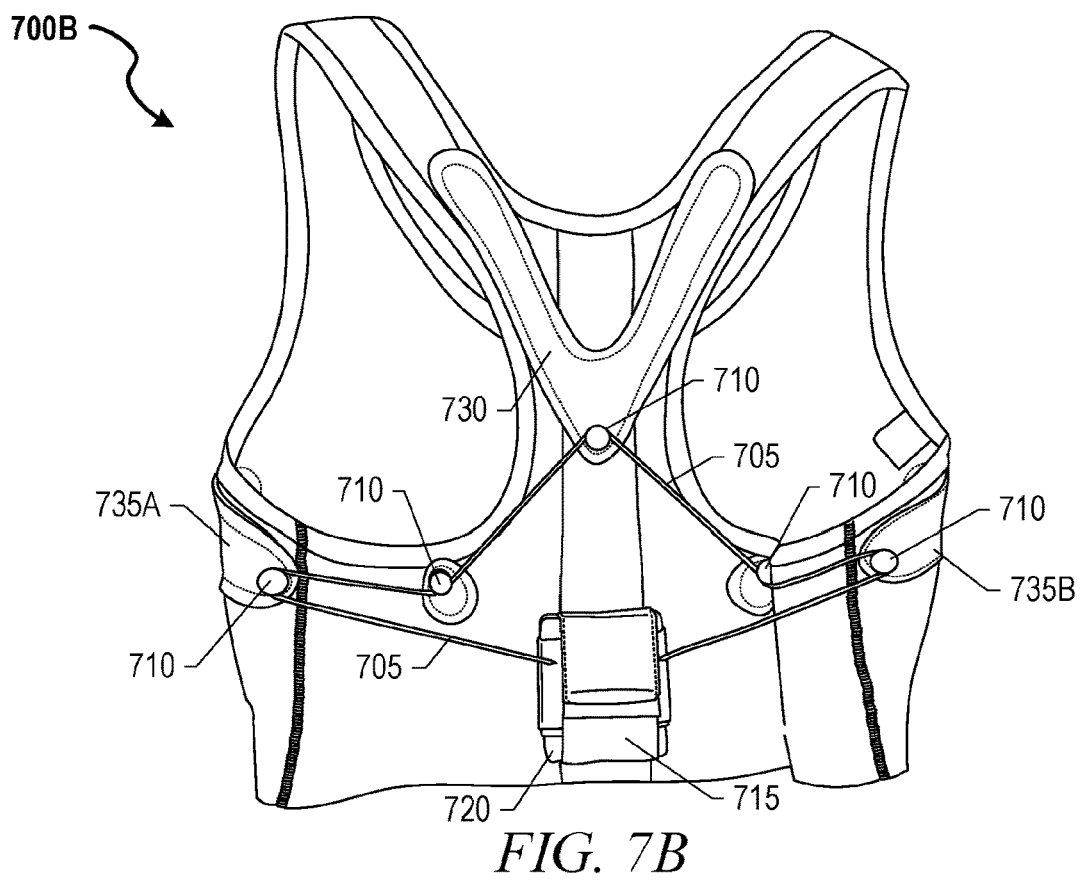
Figure 7C:
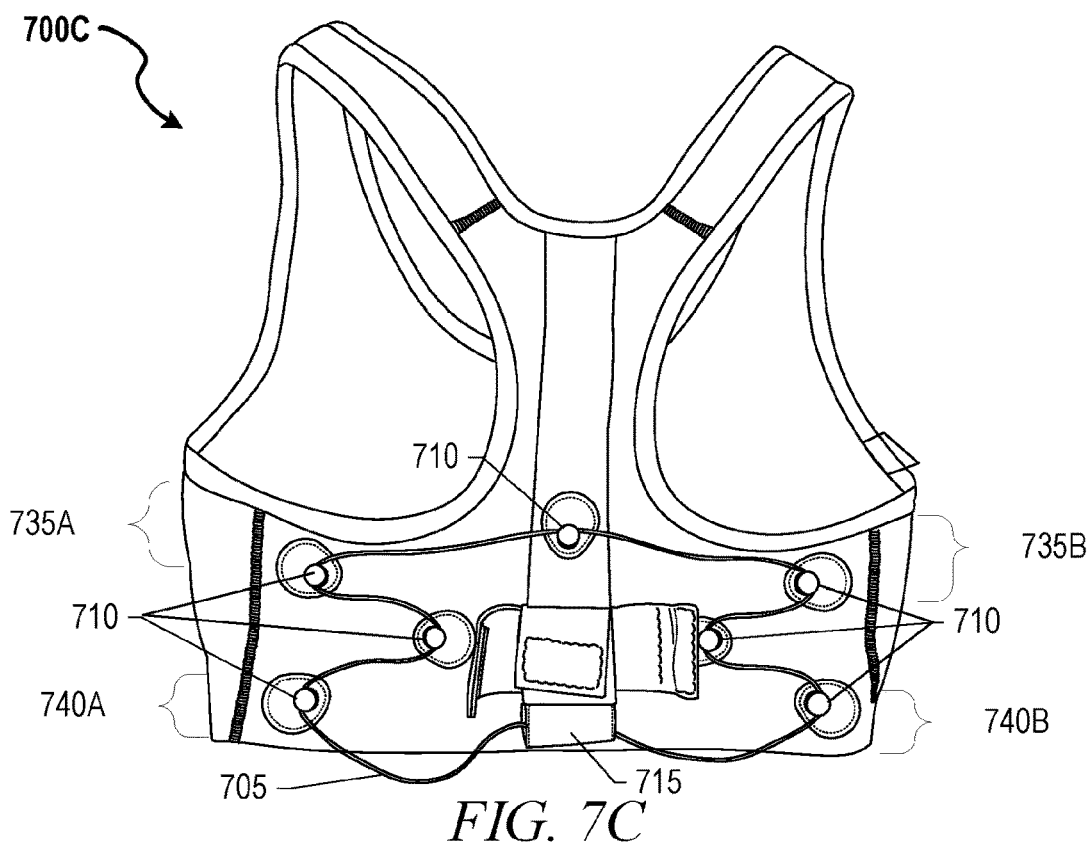
Figure 7D:
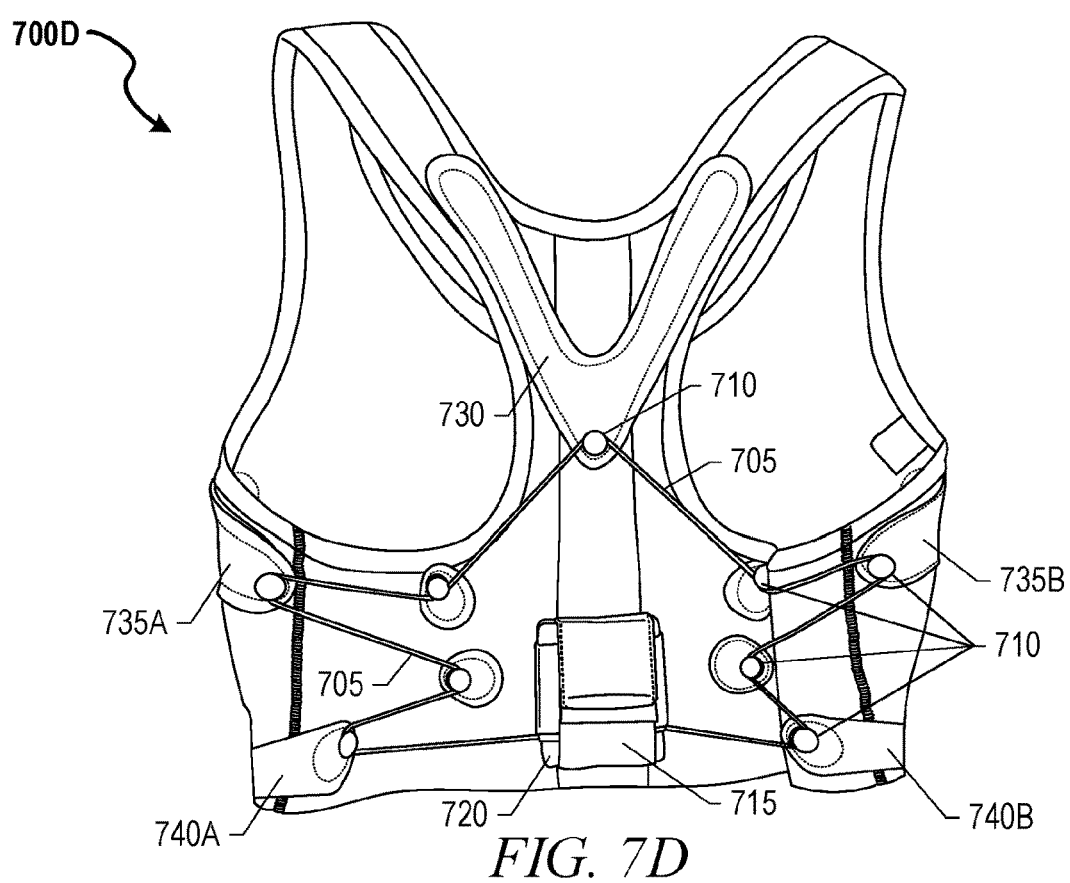

FIGS. 7A-7D are illustrations of various adaptive bra 700 configurations with automated adjustment mechanisms, according to some example embodiments. The examples of adaptive bra 700 illustrated in these figures are similar but for variations in numbers and placement of lace guide 710, which allow for creation of different support adaptations. FIG. 7A illustrates an adaptive bra 700A including two (2) lace guides 710 positioned to apply tensioning to a right wing and left wing, which provides enhanced compression across the breast tissue and gore regions. FIG. 7B illustrates adaptive bra 700B including five (5) lace guides 710 positioned to apply tension to shoulder straps and wing regions. FIG. 7C illustrates an adaptive bra 700C including seven (7) lace guides distributed in a pattern focused on gore and under-band tensioning. FIG. 7D illustrates an adaptive bra 700D including nine (9) lace guides 710 positioned to generate additional tensioning through the shoulder straps as compared to the pattern in FIG. 7C.

All of the variations of the adaptive bra 700 include a continuous lace cable 705, lace guides 710, a lacing engine pocket 715, and a lacing engine 720 (also referenced herein as an adaptive engine). The lacing engine can include an open spool configuration to enable removal of the lacing engine 720 for cleaning the garment, charging internal batteries, or replacement. The continuous lace cable 705 is engaged by the spool of the lacing engine 720 to provide automatic or semi-automatic adjustment to adaptive bra 700. In this example, the lace guides 710 are circular open lace guides, but alternative lace guides could also be utilized. For example, closed tubular lace guides could be implemented to avoid any potential for disengagement of the continuous lace cable. In other examples, the lace guides 710 can include snap-on covers that retain the lace cable during use.

Each lace guide 710 is mounted on reinforced fabric overlays to assist in distributing lace forces and longevity of the support garment.

Adaptive bra 700A, illustrated in FIG. 7A, is an example of a minimalistic adaptive support garment including two lace guides 710, a continuous lace cable 705 and a lacing engine pocket 715 to receive a lacing engine. Adaptive bra 700B adds three additional lace guides 710. One of the added lace guide 710 is affixed to a shoulder strap anchor overlay 730 that distributes forces to the shoulder straps upon tensioning of lace cable 705. Adaptive bra 700B also includes left wing strap 735A and right-wing strap 735B, which each include a lace guide 710. The remaining two lace guides 710 added to adaptive bra 700B (as compared to 700A) operate primarily to route lace cable 705 away from exposed tissue. Adaptive bra 700C includes seven (7) lace guides 710 in a slightly different configuration that focuses adaptive adjustment on left wing region 735A, right wing region 735B, left under-band region 740A, and right under-band region 740B (notice, adaptive bra 700C does not include straps or overlays in the wing or under-band region). In contrast, adaptive bra 700D includes straps or overlay reinforcements in wing regions, under-band regions, and to anchor the shoulder straps. More specifically, adaptive bra 700D includes nine (9) lace guides 710 with lace guides affixed to a shoulder strap anchor overlay 730, a left-wing strap 735A, a right-wing strap 735B, a left under-band strap 740A, and a right under-band strap 740B. Accordingly, adaptive bra 700D is configured to adjust support in the under-band, wing region, and shoulder straps resulting in adjustments to breast tissue compression and support.

Figure 8A:
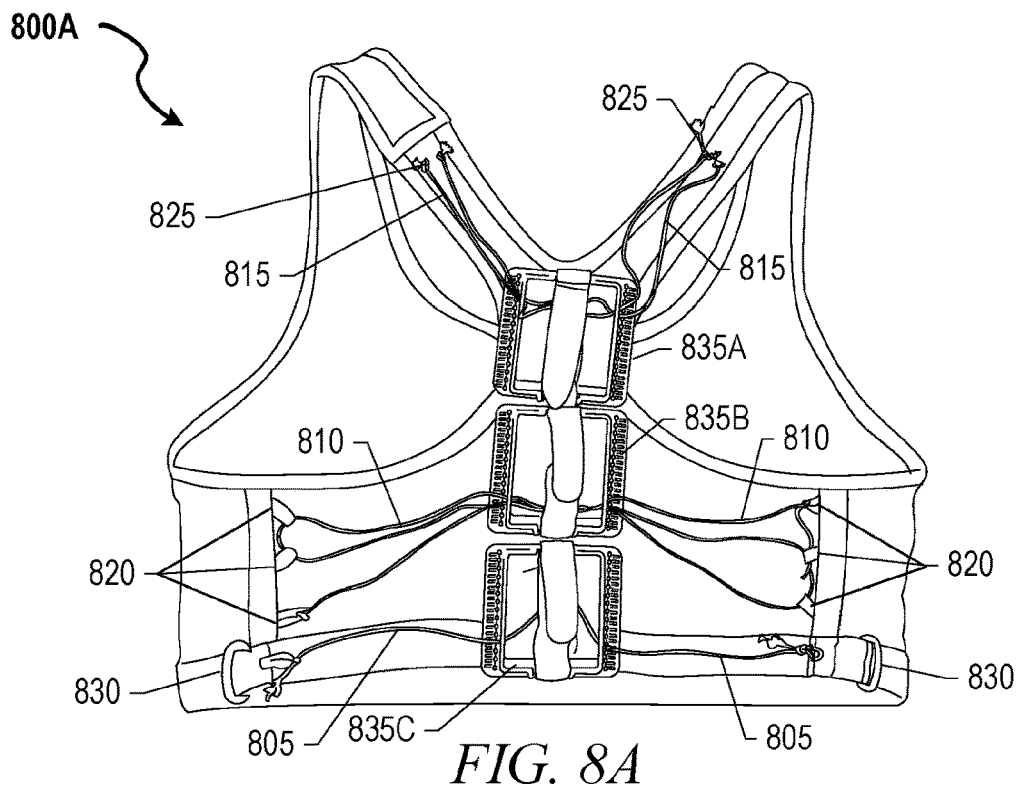
FIGS. 8A-8B are illustrations of adaptive bra configurations with multiple automated adjustment mechanisms, according to some example embodiments.
Figure 8B:
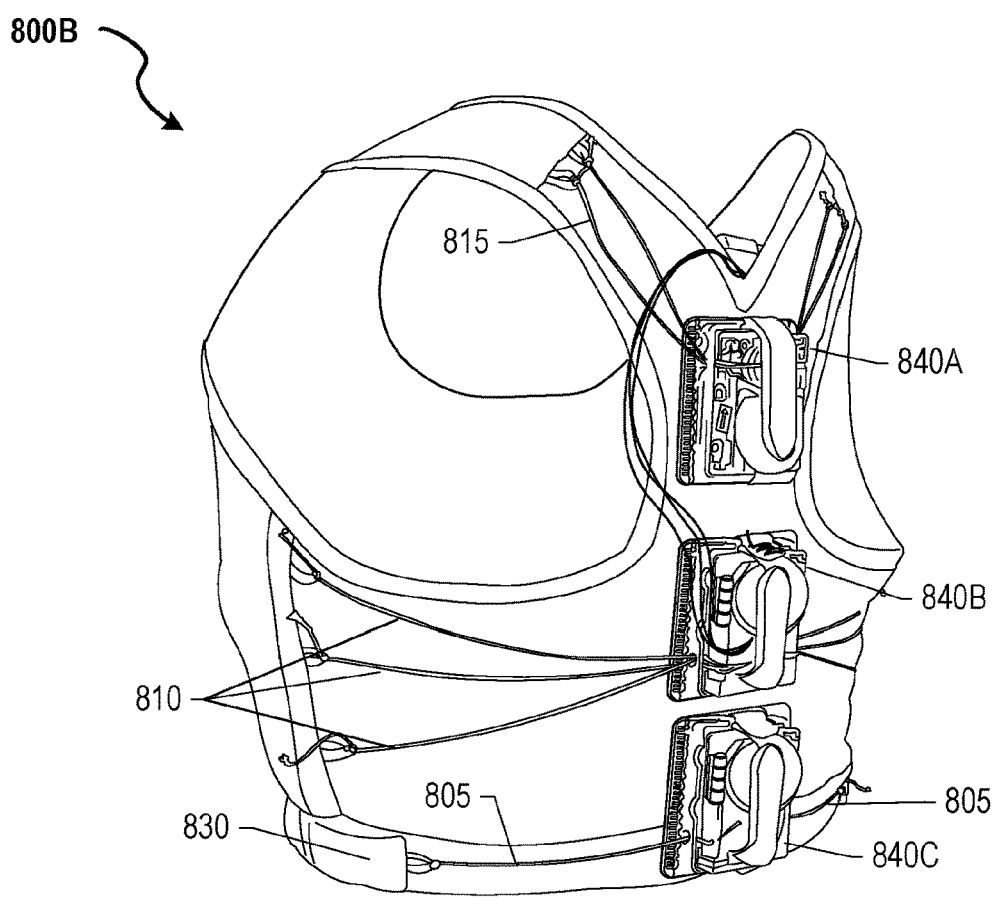

FIGS. 8A-8B are illustrations of adaptive bra 800 configurations with multiple automated adjustment mechanisms (e.g., adaptive engines), according to some example embodiments. In an example, adaptive bra 800A illustrates a posterior support structure including three separate adjustment zones, each adjustment zone including a separate adaptive engine pocket 835 to hold an adaptive engine for automatic or semi-automatic adjustment. The adaptive bra 800A includes an under-band zone with lace cable 805 coupled to under-band 830 and running through an inferior (caudal) adaptive engine pocket 835C. This example also includes a wing zone with lace cable 810 coupled to anchors 820, which distribute the tension generated on lace cable 810 across a wide area along the lateral sides of the adaptive bra 800A. Lace cable 810 is adjusted by a middle adaptive engine positioned within a central adaptive engine pocket 835B. The anchors 820 can be pulleys, circular anchors, tubular lace guides, or fabric loops, among other things. The gore zone lace cable 810 is implemented in this example as a single lace cable running from an inferior left-side anchor crisscrossing a portion of the posterior of adaptive bra 800A up to a superior right-side anchor. In other examples, the gore zone lace cable 810 can be implemented as three separate lace cables (see FIG. 8B), or some other combination of lace cables. In FIG. 8B, the three separate lace cables 810 are all routed through the central adaptive engine 840B for simultaneous adjustment. Adaptive bra 800A also includes a shoulder zone with dual lace cables 815 running from right shoulder to left shoulder through a superior (cranial) adaptive engine pocket 835A.

Adaptive bra 800B illustrated in FIG. 8B includes lacing (adaptive) engines 840A-840C within the adaptive engine pockets 835. Lacing engine 840A functions to adjust the shoulder zone lace cable 815, which will provide shoulder strap adjustment and additional lift on the breast contacting surfaces on the anterior side of adaptive bra 800B. Lacing engine 840B functions to adjust the gore zone lace cables 810 providing compression across the breast contacting surfaces. Lacing engine 840C functions to adjust the under-band zone lace cable 805 and provides tensioning support to the under-band of adaptive bra 800B.

As discussed in additional detail below, lacing engines 840A-840C can be operated through manual input (e.g., semi-automatically) or in response to sensor inputs indicating things such as activity level or tension forces on lace cables.

Shape Control

Particularly in adaptive bras that attempt to provide different levels of support for a variety of breast structures, the ability to adjust shape of the breast contacting surface is useful. Some of the examples discussed above provide adaptive support structures that include some ability to control or adjust the shape of the breast contacting surfaces. An adaptive support structure developed for use in a dynamic padding system can be utilized to provide a different level of shape control. Details of the dynamic padding system can be found in U.S. Patent Publication 2018/0140928, titled "Article of apparel with dynamic padding system", which was incorporated by reference above.

In an example, breast contacting surfaces of an adaptive bra can utilize a variation of the dynamic padding system discussed in the dynamic padding system application. The control lacing for the dynamic padding system can be routed to an adaptive engine to provide automatic or semi-automatic control of the dynamic shaping structure within the adaptive bra.

Adaptive Support Structures—Lacing Systems

Various different adaptive support structures for adaptive bras have been discussed above in reference to FIGS. 2A-8B. These adaptive support structures have generally included lacing systems running through various lace guides, tubes or fabric anchors. In other examples, the lacing system can be embedded within textiles used to build the adaptive support garment. The textiles can include knit textiles, woven textiles, and non-woven textiles, braided textiles, among others. For example, textiles may be produced to include or assembled to create tubes or tunnels within which lace cables for the various lacing system can be routed.

In an example utilizing knit textiles, a weft-knitting process called flat knitting (among other knitting processes) can be utilized to form knitted components for adaptive support garments. Various features may be incorporated into the knitted component. For example, the knitted component may define a tube formed of unitary knit construction, and a strand (lace cable) may extend through a length of the tube. As another example, the knitted component may have a pair of at least partially coextensive knitted layers formed of unitary knit construction, and a plurality of floating yarns may extend between the knitted layers. In some configurations, the knit type or yarn type may vary in different regions of the knitted component to impart different properties. Additionally, the knitted component may incorporate a thermoplastic yarn that is fused in different regions of the knitted component to impart different properties. U.S. Pat. No. 8,745,896, titled "Article of footwear having an upper incorporating a knitted component" includes additional details on how knitted textiles can be utilized to create fabric tubes or tunnels for routing lacing systems. U.S. Pat. No. 8,745,896 is hereby incorporated by reference in its entirety.

Knitting processes can be used to inlaid yarns, stands, or cables that can be used within lacing systems discussed here. At least a portion of a cable (yarn or strand) may be inlaid between certain loops of the knitted component on a knitting machine during the manufacturing of the knitted component. The cable may be inserted within a knit tube during a knitting process, such as by utilizing an inlay process. For example, an inlay process may include using an inlay feeder or other mechanical inlay device on a knitting machine (e.g., a combination feeder) to place the cable between two needle beds (e.g., front and back needle beds) during a knitting process. One example of an inlay process, along with a combination feeder for enabling such a process, is described in U.S. Patent Application Publication No. 2013/0145652, published Jun. 13, 2013, and having an applicant of NIKE, Inc., which is hereby incorporated by reference in its entirety. Alternatively, the cable may be fed through the knit tubes of the knitted component by hand and/or another suitable method. It is contemplated that the cable may be attached to the remainder of a lacing system in a different way (e.g., other than being located in a tube), such as by using an adhesive to secure the cable directly to components of a support structure or lacing system as discussed herein.

A knit tube is generally a hollow structure formed by two overlapping and at least partially coextensive layers of knitted material (example shown in FIG. 3C and discussed above). Although the sides or edges of one layer of the knitted material forming the tube may be secured to the other layer (e.g., if a two-layer construction extends beyond the tube), a central area is generally unsecured such that another element (e.g., the cable) may be located between the two layers of knitted material and pass through the tube.

More specifically, the tube may be formed by a multi-layer knit structure, such as a tubular knit structure. The tubular knit structure may be formed by a tubular knitting process where a first knit layer formed on a first bed of the knitting machine remains separable from (e.g., having a central area not locked to) a second knit layer formed on a second needle bed for a plurality of courses. For example, a first layer of the tube, which may define the exterior surface of the knitted component, may be formed on a first needle bed of a knitting machine (e.g., with a single-jersey or similar knit structure). A second layer of the tube, which may define an inner surface of the knitted component, may be formed on a second needle bed of the knitting machine (e.g., with a single-jersey or similar knit structure). The edges of the tube (which extend along the tube's length) may correspond with locations where a course at the end of the tubular knit structure (in the knitting direction) utilizes both needle beds, thus locking the first layer and the second layer together (though discrete layers may optionally continue, in a secured manner, past the edges in some embodiments). In the resulting knitted component, a channel/tunnel may be formed between the first layer and the second layer of the tube, and that same channel may be used for receipt of the cable.

The yarn, strand, or cable discussed above, can include an inlaid strand having the configurations of a filament (e.g., a monofilament), multifilament, strand, yarn, thread, rope, webbing, cable, or chain, for example. In comparison with the yarns forming a knit element, such as adaptive support garment 10, the thickness of an inlaid strand may be greater. In some configurations, the inlaid strand may have a significantly greater thickness than the yarns of the knit element. Although the cross-sectional shape of the inlaid strand may be round, triangular, square, rectangular, elliptical, or irregular shapes may also be utilized. Moreover, the materials forming the inlaid strand may include any of the materials for the yarn within the knit element, such as cotton, elastane, polyester, rayon, wool, and nylon. As noted above, the inlaid strand may exhibit greater stretch-resistance than the reminder of the knit element. As such, suitable materials for inlaid strands may include a variety of engineering filaments that are utilized for high tensile strength applications, including glass, aramids (e.g., para-aramid and meta-aramid), ultra-high molecular weight polyethylene, and liquid crystal polymer. As another example, a braided polyester thread may also be utilized as inlaid strand.

The lacing systems discussed throughout this disclosure represent just some of the example arrangements that could provide the desire support within an adaptive support garment. Other lacing architectures could be adapted from related garments or footwear. For example, automated lacing footwear platforms disclosed in U.S. Patent Publication 2019/0116935, titled "Lacing Architecture for Automated Footwear Platform", and U.S. Patent Publication 2018/0110298, titled "Lacing Architecture for Automated Footwear Platform" both disclose lacing structures that could be adapted for use within an adaptive support garment. U.S. Patent Publications 2019/0116935 and 2018/0110298 are hereby incorporated by reference in their entirety.

Sensors and Control Systems

In order to effectively and automatically manipulate an adaptive support garment in response to changes in physical activity, a control system needs to be able to collect data that indicates how portions of anatomy related to the adaptive support garment are moving and/or stresses being experienced on portions of the adaptive support garment. Sensors such as motion tracking sensors and force measurement sensors (e.g., strain gauges) are examples of sensors that can be utilized to provide the needed data.

Force sensors can be embedded into relative portions of the adaptive support garments, be separate devices worn by a user, and/or be integrated into adaptive adjustment engines to detect forces being applied to the support structures within the adaptive support garments. In response to changes in the forces, different adjustments can be made to counter act these forces. For example, sensors can be utilized to detect impact forces experienced on shoulder straps of an adaptive bra. The impact force data can be interpreted to indicate the level of compression or breast tissue isolation the adaptive bra should be providing to the wearer.

In addition to, or instead of, a force sensor embedded into the adaptive support garments, the garment can include stretch capacitive sensors to monitor for increased activity levels. In an example, an adaptive support garment can include one or more stretchable capacitive sensors in key locations, such as shoulder straps, under-band, and/or in association with anchor points for the various adaptive support structures and lacing systems discussed herein. The stretchable capacitive sensors can detect athletic movements indicative of an activity level of a wearer, and signals from these sensors can be processed by control circuits as discussed herein to determine a desired support level for the adaptive support garment.

Additional details on related implementations of the stretchable capacitive sensors can be found in U.S. Patent Publication 2019/0059461, titled "Sense-Enabled Apparel" the contents of which are incorporated herein in their entirety for any and all non-limiting purposes. Examples of stretchable capacitive sensors that may be utilized in accordance with various embodiments are disclosed in U.S. Pat. No. 7,958,789, and WO 2014/204323, the contents of which are incorporated herein in their entirety for any and all non-limiting purposes. The control circuit 50 discussed above can also utilize sensor inputs to trigger lighting integrated into adaptive apparel. Lighting can be integrated for safety during nighttime activities.

In some example, motion tracking sensors are used to detect activity levels for wearers of an adaptive support garment. Motion tracking sensors, such as inertial measurement units (IMUs) are capable of tracking up to six degrees-of-freedom (DOF) and can be applied to various portions of anatomy to provide feedback to a control system monitoring the adaptive support garment. One such sensor is from a company named Polhemus (https://polhemus.com/microsensors/), but similar sensors are available from other manufacturers. 6-DOF motion sensors are able to capture degrees of displacement, both linear and rotational, frequency of movement, and/or velocity of movement through up to six degrees of movement. In an adaptive bra example, by associating a sensor with the breast structure and specifically with a nipple area of the breast structure, the sensor is able to accurately capture the displacement experienced by the breast structure during movement. Moreover, since the nipple area typically represents the anterior-most aspect of breast tissue, positioning the sensor in this location enable the sensor to capture maximum amount of displacement experienced by the breast structures. A control system within an automated adaptive bra can utilize this sensor data (e.g., displacement data, frequency, and velocity data) to adaptively adjust the support structures to compensation for changes in the collected data as activity levels change. The description above is intended to expland and/or enhance earlier discussions related to sensor(s) 25, which are also referenced throughout as activity sensors.

Adaptive Adjustment Engine

The following discusses a motorized lacing engine example utilized in some of the adaptive bra examples discussed above as an adaptive adjustment engine. While much of this disclosure focuses on a motorized lacing engine, many of the mechanical aspects of the discussed designs are applicable to a human-powered lacing engine or other motorized lacing engines with additional or fewer capabilities. Accordingly, the term "automated" or "adaptive" as used in "adaptive apparel" or "automated apparel platform" is not intended to only cover a system that operates without user (e.g., manual) input. Rather, the term "automated/adaptive apparel platform" includes various electrically powered and human-powered, automatically activated and human activated mechanisms for adaptive support systems discussed herein.

In an example, the adaptive support systems can include or are configured to interface with one or more sensors that can monitor or determine a dynamic physical characteristic, such as breast (e.g., soft tissue) acceleration or displacement. Based on information from one or more sensors, the adaptive support system, such as one of the adaptive bras discussed above and including the motorized lacing engine (also referred to herein as an adaptive engine) can be configured to perform various functions. For example, a sensor can be configured to detect activity level to which the adaptive support system can react by adjusting support structures. In an example, the adaptive apparel article includes a processor circuit that can receive or interpret signals from a sensor. The processor circuit can optionally be embedded in or with the lacing engine 900.

Figure 9A:
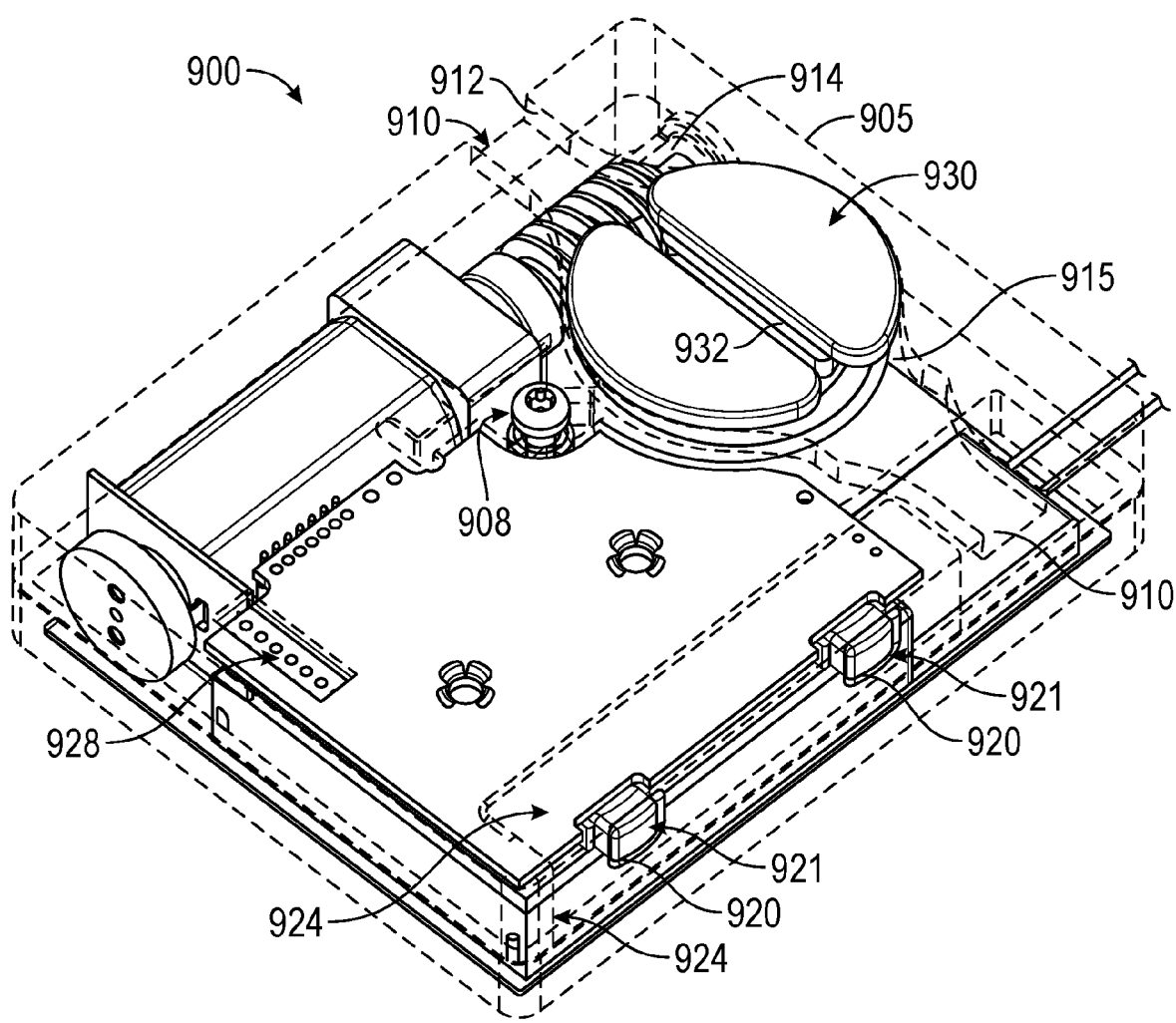
FIGS. 9A-9E are diagrams and drawings illustrating a motorized lacing engine, according to some example embodiments.

Examples of the lacing engine 900 are described in detail in reference to FIGS. 9A-9F. FIGS. 9A-9F are diagrams and drawings illustrating a motorized lacing engine, according to some example embodiments. Note, reference numbering for FIGS. 9A-9F may overlap or be duplicative of reference numbers used in other parts of this disclosure. FIG. 9A introduces various external features of an example lacing engine 900, including a housing structure 905, case screw 908, lace channel 910 (also referred to as lace guide relief 910), lace channel wall 912, lace channel transition 914, spool recess 915, button openings 920, buttons 921, button membrane seal 924, programming header 928, spool 930, and lace grove 932.

In an example, the lacing engine 900 is held together by one or more screws, such as the case screw 908. The case screw 908 is positioned near the primary drive mechanisms to enhance structural integrity of the lacing engine 900. The case screw 908 also functions to assist the assembly process, such as holding the case together for ultra-sonic welding of exterior seams.

In this example, the lacing engine 900 includes a lace channel 910 to receive a lace or lace cable once assembled into an automated adaptive garment platform. The lace channel 910 can include a lace channel wall 912. The lace channel wall 912 can include chamfered edges to provide a smooth guiding surface for a lace cable to run in during operation. Part of the smooth guiding surface of the lace channel 910 can include a channel transition 914, which is a widened portion of the lace channel 910 leading into the spool recess 915. The spool recess 915 transitions from the channel transition 914 into generally circular sections that conform closely to the profile of the spool 930. The spool recess 915 assists in retaining the spooled lace cable, as well as in retaining position of the spool 930. However, other aspects of the design provide primary retention of the spool 930. In this example, the spool 930 is shaped similarly to half of a yo-yo with a lace grove 932 running through a flat top surface and a spool shaft 933 (not shown in FIG. 9A) extending inferiorly from the opposite side. The spool 930 is described in further detail below in reference of additional figures.

The lateral side of the lacing engine 900 includes button openings 920 that enable buttons 921 for activation of the mechanism to extend through the housing structure 905. The buttons 921 provide an external interface for activation of switches 922, illustrated in additional figures discussed below. In some examples, the housing structure 905 includes button membrane seal 924 to provide protection from dirt and water. In this example, the button membrane seal 924 is up to a few mils (thousandth of an inch) thick clear plastic (or similar material) adhered from a superior surface of the housing structure 905 over a corner and down a lateral side. In another example, the button membrane seal 924 is a 2-mil thick vinyl adhesive backed membrane covering the buttons 921 and button openings 920.

Figure 9B:
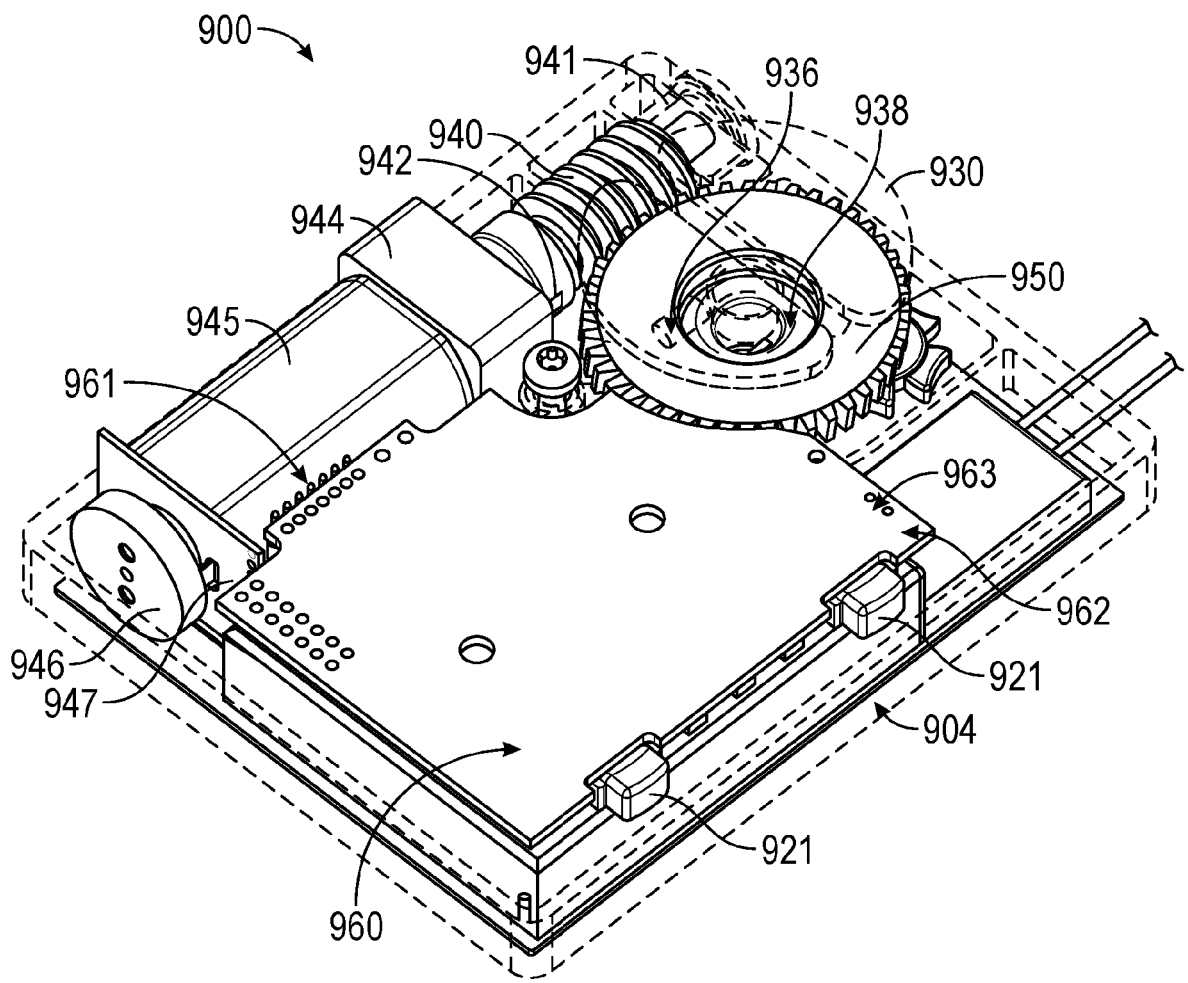

FIG. 9B is an illustration of various internal components of lacing engine 900, according to example embodiments. In this example, the lacing engine 900 further includes spool magnet 136, O-ring seal 938, worm drive 940, bushing 941, worm drive key 942, gear box 944, gear motor 945, motor encoder 946, motor circuit board 947, worm gear 950, circuit board 960, motor header 961, battery connection 962, and wired charging header 963. The spool magnet 936 assists in tracking movement of the spool 930 though detection by a magnetometer (not shown in FIG. 9B). The O-ring seal 938 functions to seal out dirt and moisture that could migrate into the lacing engine 900 around the spool shaft 933.

In this example, major drive components of the lacing engine 900 include worm drive 940, worm gear 950, gear motor 945 and gear box 944. The worm gear 950 is designed to inhibit back driving of worm drive 940 and gear motor 945, which means the major input forces coming in from the lacing cable via the spool 930 are resolved on the comparatively large worm gear and worm drive teeth. This arrangement protects the gear box 944 from needing to include gears of sufficient strength to withstand both the dynamic loading from active use of the adaptive garment or tightening loading from tightening the lacing system. The worm drive 940 includes additional features to assist in protecting the more fragile portions of the drive system, such as the worm drive key 942. In this example, the worm drive key 942 is a radial slot in the motor end of the worm drive 940 that interfaces with a pin through the drive shaft coming out of the gear box 944. This arrangement prevents the worm drive 940 from imparting any axial forces on the gear box 944 or gear motor 945 by allowing the worm drive 940 to move freely in an axial direction (away from the gear box 944) transferring those axial loads onto bushing 941 and the housing structure 905.

Figure 9C:
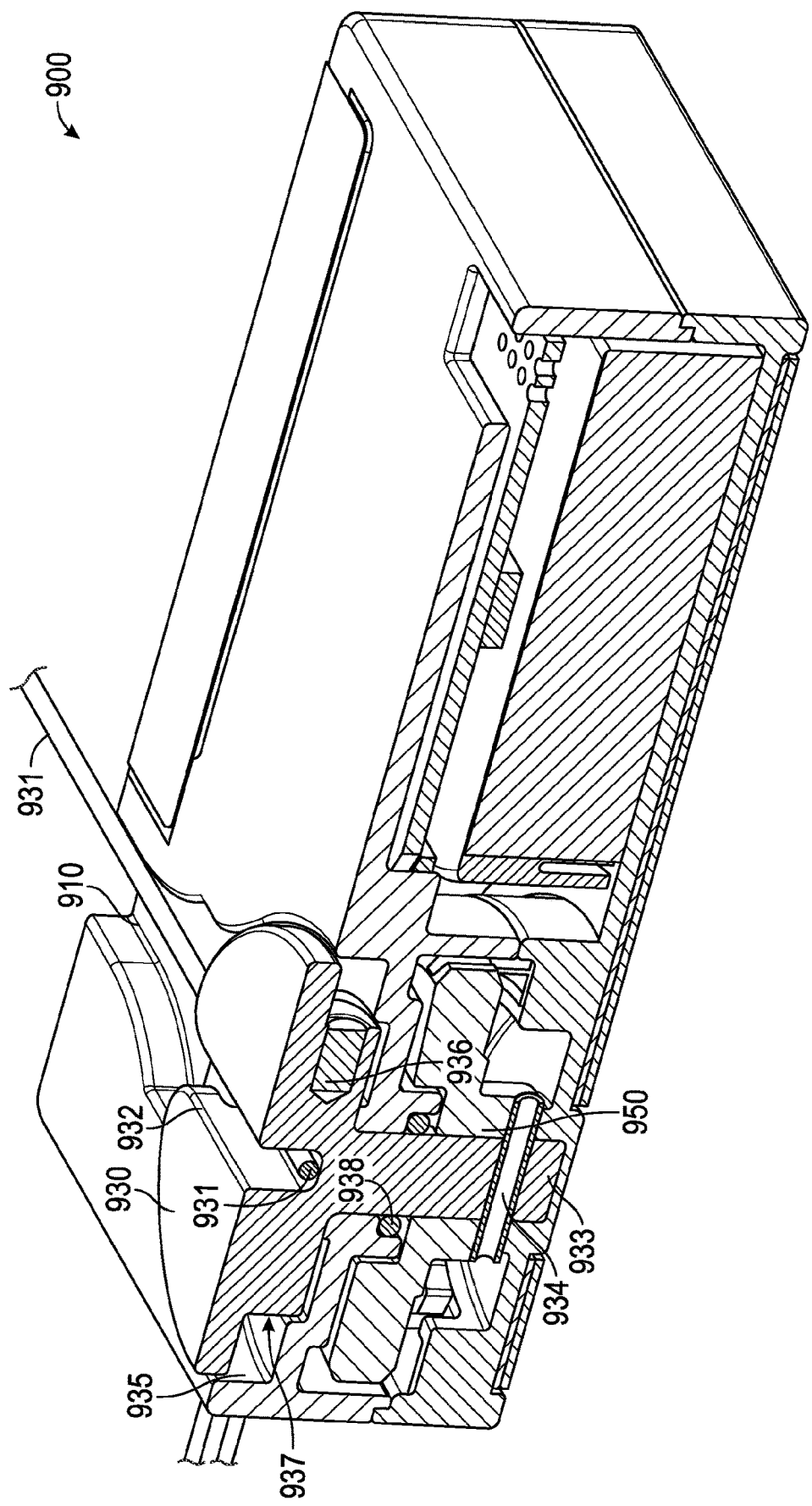

FIG. 9C is a cross-section illustration of the lacing engine 900, according to example embodiments. FIG. 9C assists in illustrating the structure of the spool 930 as well as how the lace grove 932 and lace channel 910 interface with lace cable 931. As shown in this example, lace 931 runs continuously through the lace channel 910 and into the lace grove 932 of the spool 930. The cross-section illustration also depicts lace recess 935 and spool mid-section, which are where the lace 931 will build up as it is taken up by rotation of the spool 930. The spool mid-section 937 is a circular reduced diameter section disposed inferiorly to the superior surface of the spool 930. The lace recess 935 is formed by a superior portion of the spool 930 that extends radially to substantially fill the spool recess 915, the sides and floor of the spool recess 915, and the spool mid-section 937. In some examples, the superior portion of the spool 930 can extend beyond the spool recess 915. In other examples, the spool 930 fits entirely within the spool recess 915, with the superior radial portion extending to the sidewalls of the spool recess 915, but allowing the spool 930 to freely rotation with the spool recess 915. The lace 931 is captured by the lace groove 932 as it runs across the lacing engine 900, so that when the spool 930 is turned, the lace 931 is rotated onto a body of the spool 930 within the lace recess 935.

As illustrated by the cross-section of lacing engine 900, the spool 930 includes a spool shaft 933 that couples with worm gear 950 after running through an O-ring 938. In this example, the spool shaft 933 is coupled to the worm gear via keyed connection pin 934. In some examples, the keyed connection pin 934 only extends from the spool shaft 933 in one axial direction, and is contacted by a key on the worm gear in such a way as to allow for an almost complete revolution of the worm gear 950 before the keyed connection pin 934 is contacted when the direction of worm gear 950 is reversed. A clutch system could also be implemented to couple the spool 930 to the worm gear 950. In such an example, the clutch mechanism could be deactivated to allow the spool 930 to run free upon de-lacing (loosening). In the example of the keyed connection pin 934 only extending is one axial direction from the spool shaft 933, the spool is allowed to move freely upon initial activation of a relaxing (de-lacing) process, while the worm gear 950 is driven backward. Allowing the spool 930 to move freely during the initial portion of a de-lacing process assists in preventing tangles in the lace 931 as it provides time for the adaptive support garment to respond, which in turn will tension the lace 931 in the loosening direction prior to being driven by the worm gear 950.

Figure 9D:
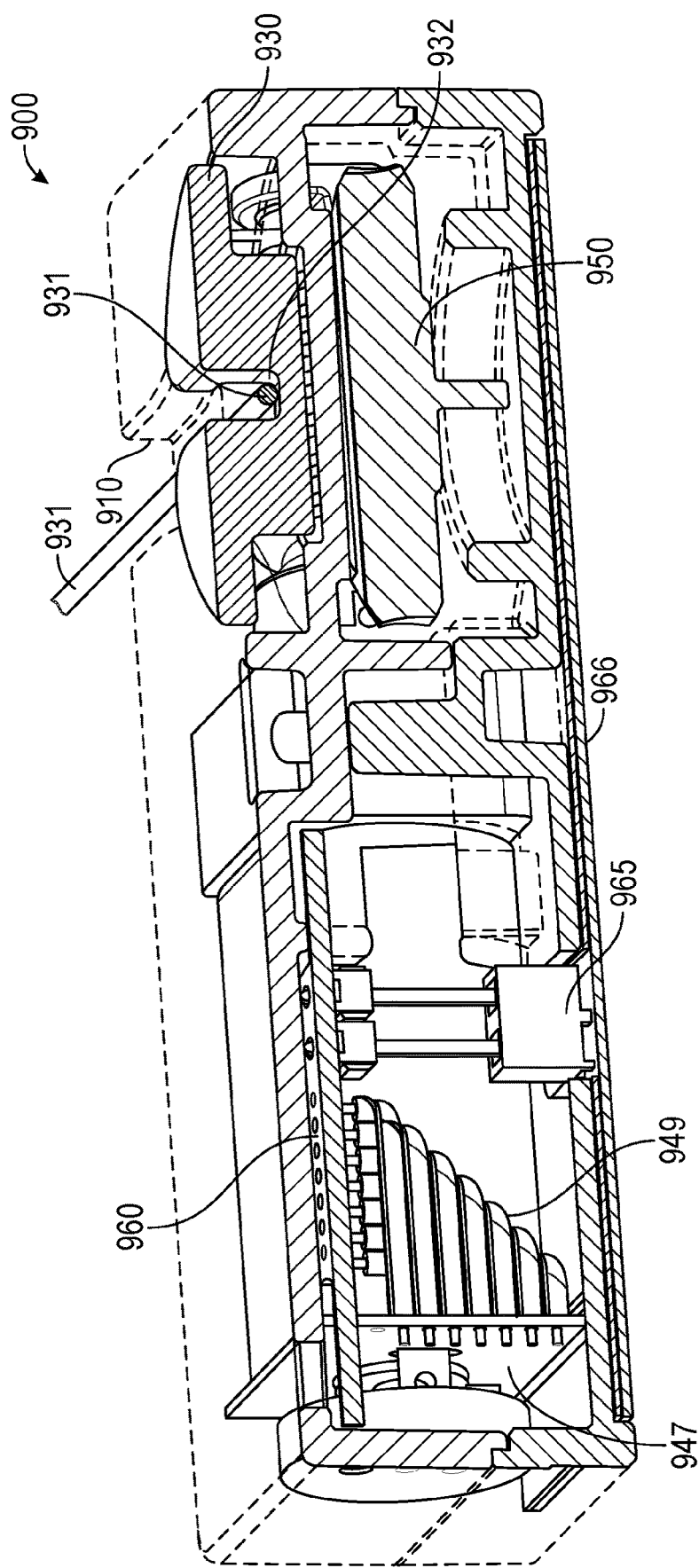

FIG. 9D is another cross-section illustration of the lacing engine 900, according to example embodiments. FIG. 2G illustrates a more medial cross-section of the lacing engine 900, as compared to FIG. 2F, which illustrates additional components such as circuit board 160, wireless charging interconnect 165, and wireless charging coil 966. FIG. 2G is also used to depict additional detail surround the spool 930 and lace 931 interface.

Figure 9E:
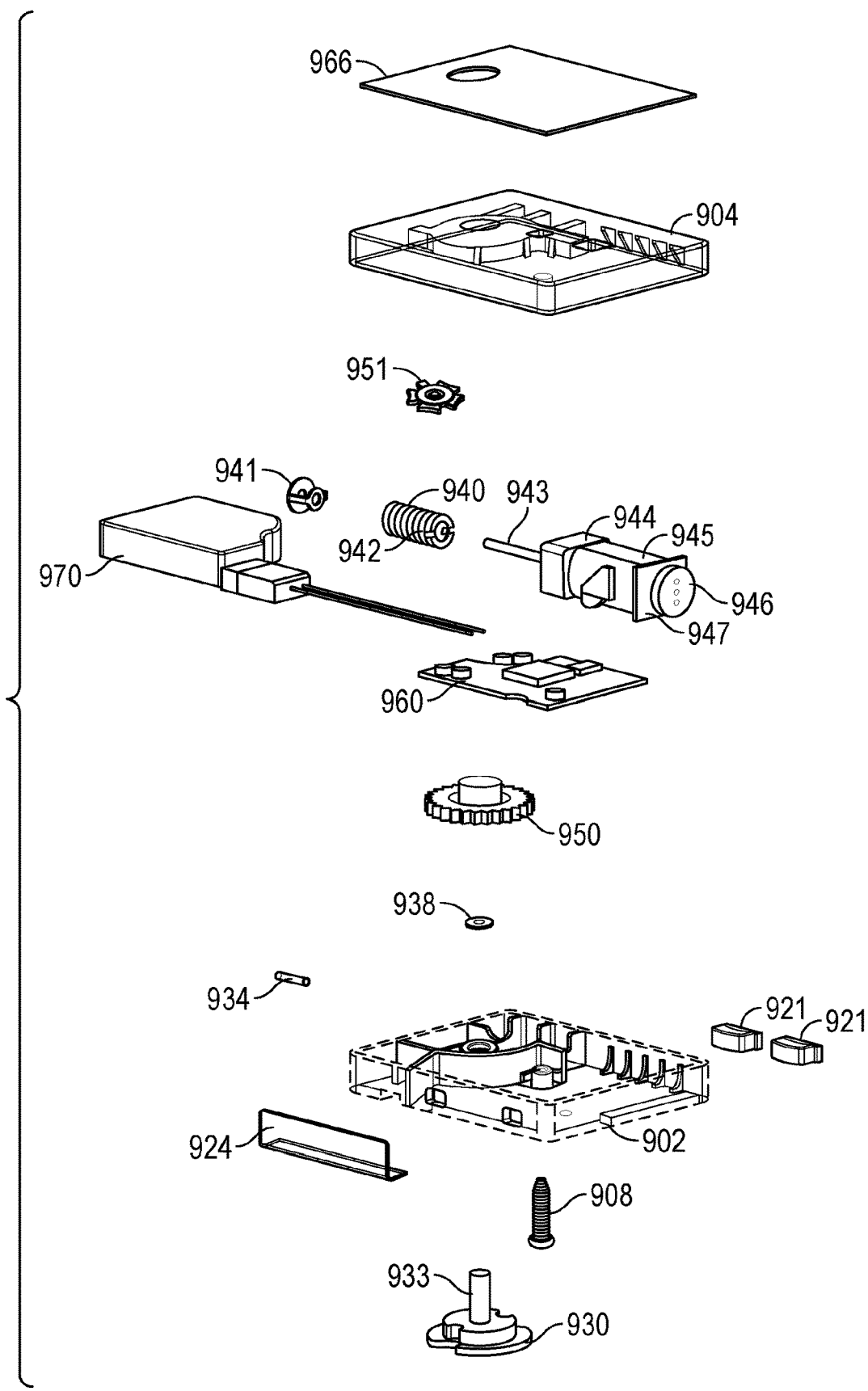

FIG. 9E is an exploded view of lacing engine 900, according to example embodiments. The exploded view of the lacing engine 900 provides an illustration of how all the various components fit together. FIG. 9E shows the lacing engine 900 upside down, with the bottom section 904 at the top of the page and the top section 902 near the bottom. In this example, the wireless charging coil 966 is shown as being adhered to the outside (bottom) of the bottom section 904. The exploded view also provides a good illustration of how the worm drive 940 is assembled with the bushing 941, drive shaft 943, gear box 944 and gear motor 945. The illustration does not include a drive shaft pin that is received within the worm drive key 942 on a first end of the worm drive 940. As discussed above, the worm drive 940 slides over the drive shaft 943 to engage a drive shaft pin in the worm drive key 942, which is essentially a slot running transverse to the drive shaft 943 in a first end of the worm drive 940.

Figure 9F:
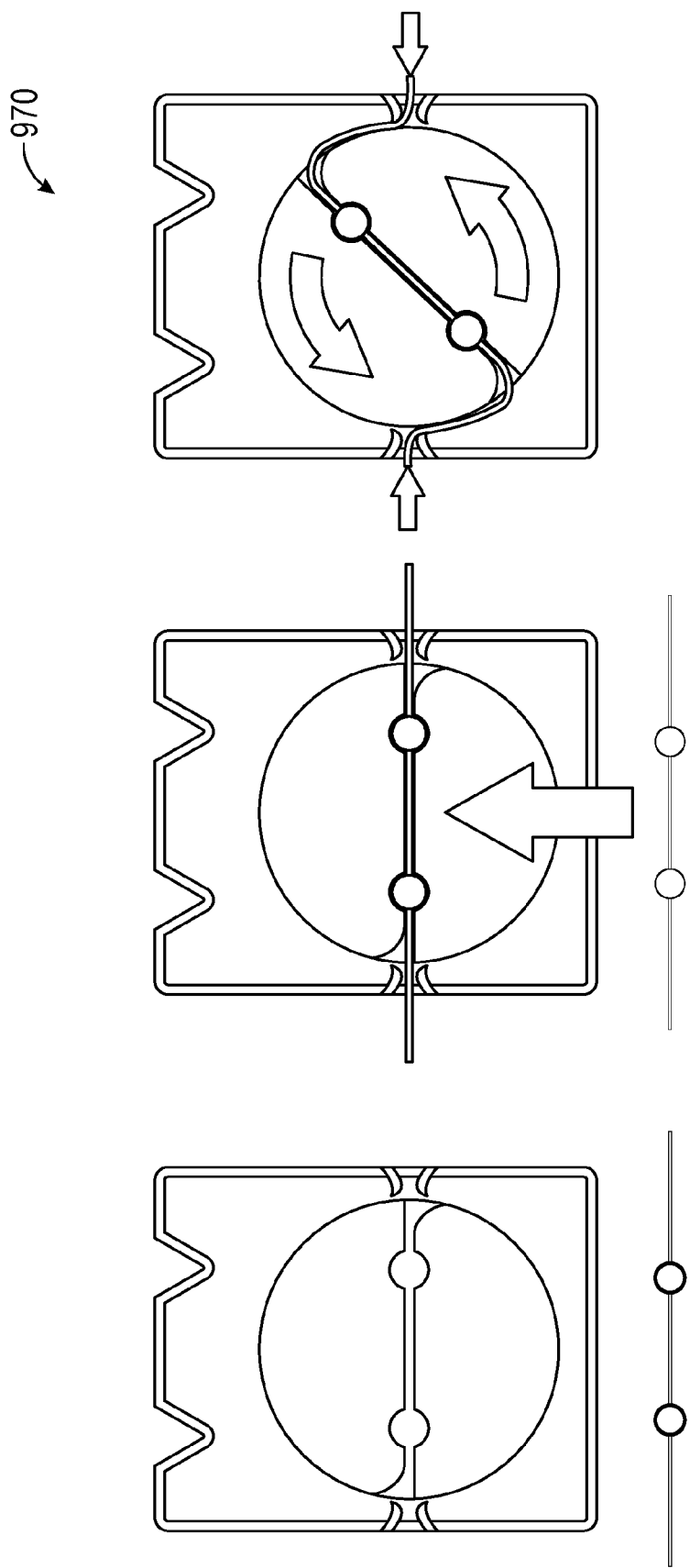
FIG. 9F is a drawing illustrating a mechanism for securing a lace within a spool of a lacing engine, according to some example embodiments.

FIG. 9F is a drawing illustrating a mechanism for securing a lace within a spool of a lacing engine, according to some example embodiments. In this example, spool 930 of lacing engine 900 receives lace cable 931 within lace grove 932. FIG. 9F includes a lace cable with ferrules and a spool with a lace groove that include recesses to receive the ferrules. In this example, the ferrules snap (e.g., interference fit) into recesses to assist in retaining the lace cable within the spool. Other example spools, such as spool 930, do not include recesses and other components of the automated adaptive garment are used to retain the lace cable in the lace groove of the spool. These examples further highlight the need or at least usefulness of an adaptive adjustment engine that can be easily removed from the adaptive garment for cleaning of the garment.

Figure 10:
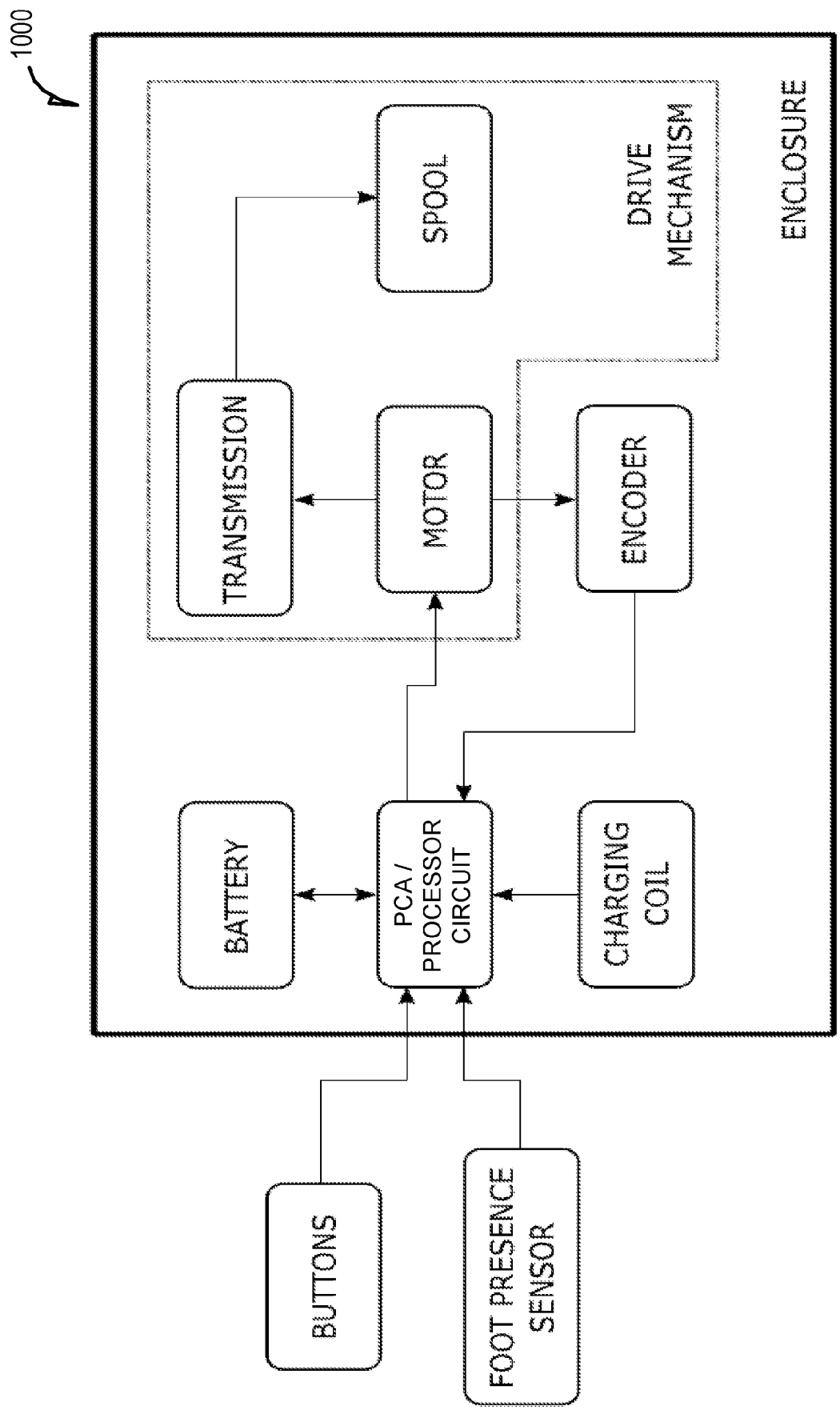
FIG. 10 is a block diagram illustrating components of a motorized lacing system, according to some example embodiments.

FIG. 10 is a block diagram illustrating components of a motorized lacing system for an adaptive support garment, according to some example embodiments. The system 1000 illustrates basic components of a motorized lacing system such as including interface buttons, foot presence sensor(s), a printed circuit board assembly (PCA) with a processor circuit, a battery, a charging coil, an encoder, a motor, a transmission, and a spool. In this example, the interface buttons and sensor(s) (such as those discussed above) communicate with the circuit board (PCA), which also communicates with the battery and charging coil. The encoder and motor are also connected to the circuit board and each other. The transmission couples the motor to the spool to form the drive mechanism. Within adaptive garment applications, the sensor inputs are utilized to receive sensor inputs from sensors monitoring anatomy parameters (e.g., movement, displacement, velocity, acceleration, etc . . . ) or parameters of the adaptive garment, rather than foot presence as done when the motorized lacing system is integrated into a footwear assembly.

In an example, the processor circuit controls one or more aspects of the drive mechanism. For example, the processor circuit can be configured to receive information from the buttons and/or from the sensors (illustrated as a foot presence sensor) and/or from the battery and/or from the drive mechanism and/or from the encoder, and can be further configured to issue commands to the drive mechanism, such as to tighten or loosen the adaptive support garment, or to obtain or record sensor information, among other functions.

Adaptive Tights

FIGS. 11A-11E illustrate various adaptive tights configurations including manual or automatic adaptive adjustment, in accordance with some examples. In an example, adaptive tights 1100A are compression-type athletic tights constructed from various fabrics with different characteristics. The body fabric (white/unpatterned portions) are woven, non-woven, or knit textile with some elastic properties, which are at least sufficient to comfortably form to the wearer's contours. The super stretch fabric (dark grey/heavily patterned portions) are highly elastic and provide much of the built-in compression provided by the tights. In some examples, adaptive tights 1100A also include mesh areas to enhance breathability of the garment.

Adaptive tights 1100A also include an adaptive support structure in the form of lace 1110 and guide tubes 1120. In this example, the lace 1110 is routed in a split helix pattern on the inside (medial) facing section along the inferior portion (distal of the knee) and on the outside (lateral) facing section along the superior portion (proximal of the knee) to an adjustment mechanism 1130 along the posterior portion of the waistline. The split helix lacing pattern has been found to provide added spring when engaged during physical activity. Other lacing patterns can be implemented to provide additional compression or other types of adaptive support. In certain examples, the adjustment mechanism 1130 can be replaced with an adaptive engine, such as discussed above, for automated control of the support structure (e.g., lace 1110 routed through guide tubes 1120).

Figure 11A:
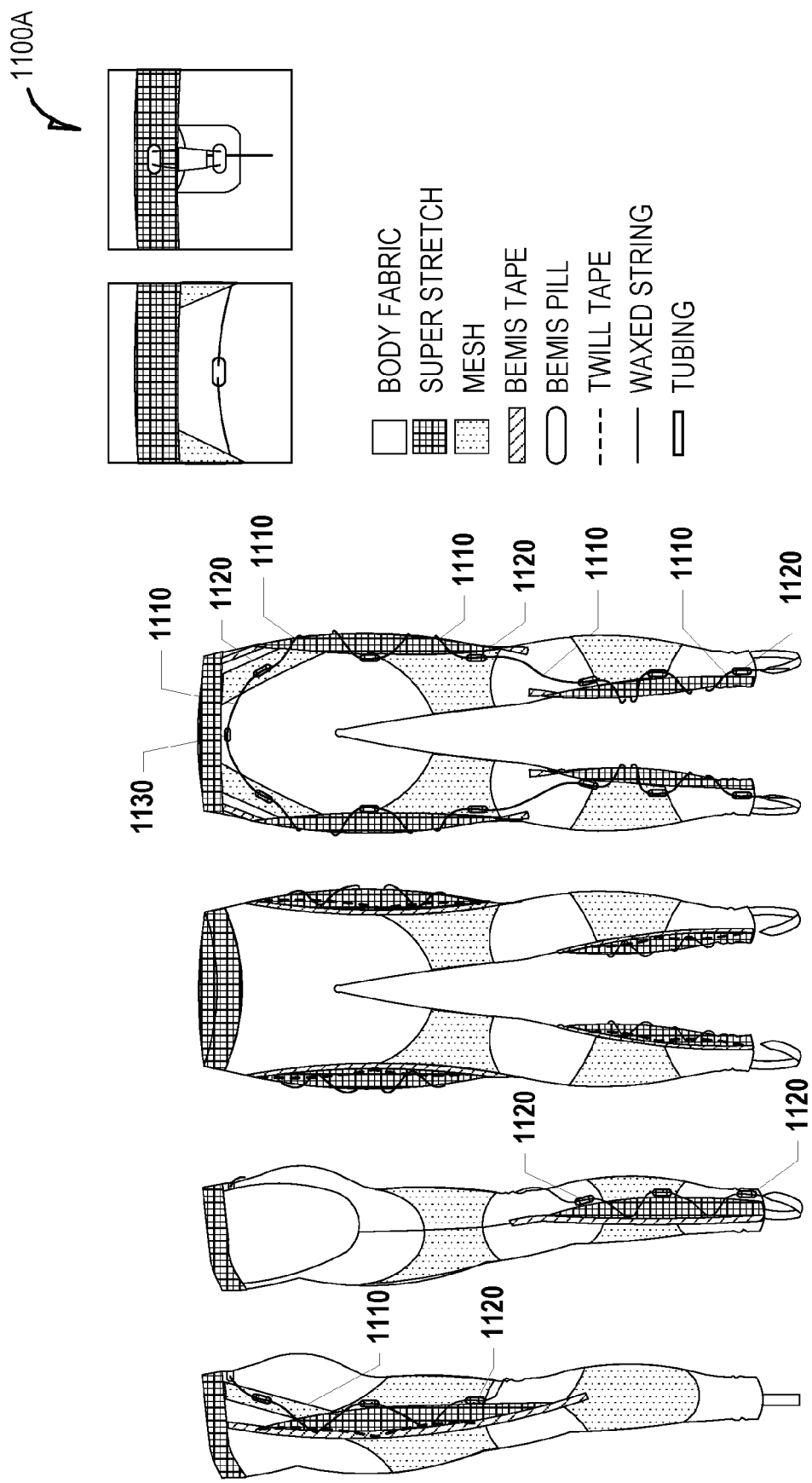
FIGS. 11A-11E illustrate various adaptive tights configurations including manual or automatic adaptive adjustment, in accordance with some examples.
Figure 11B:
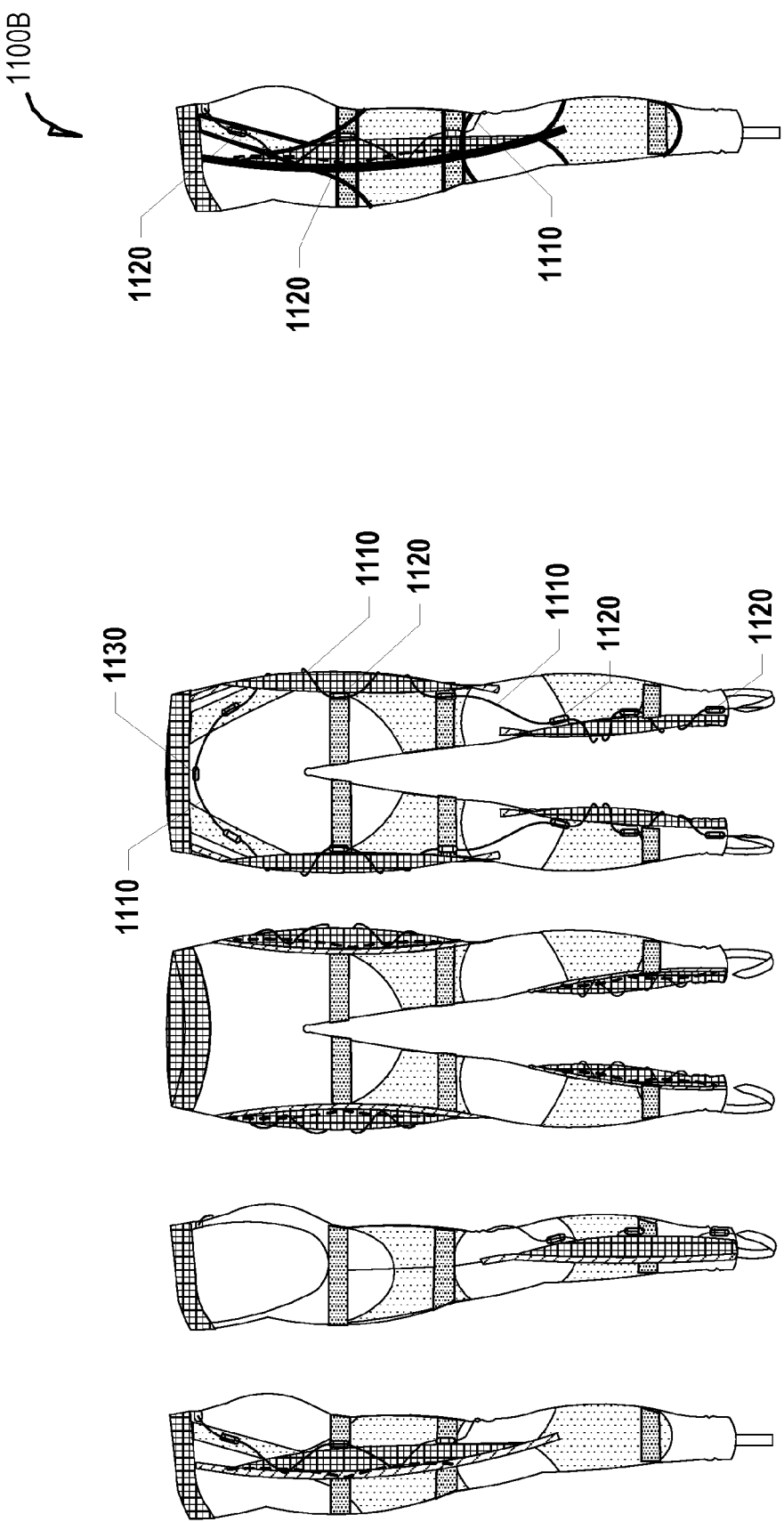
Figure 11C:
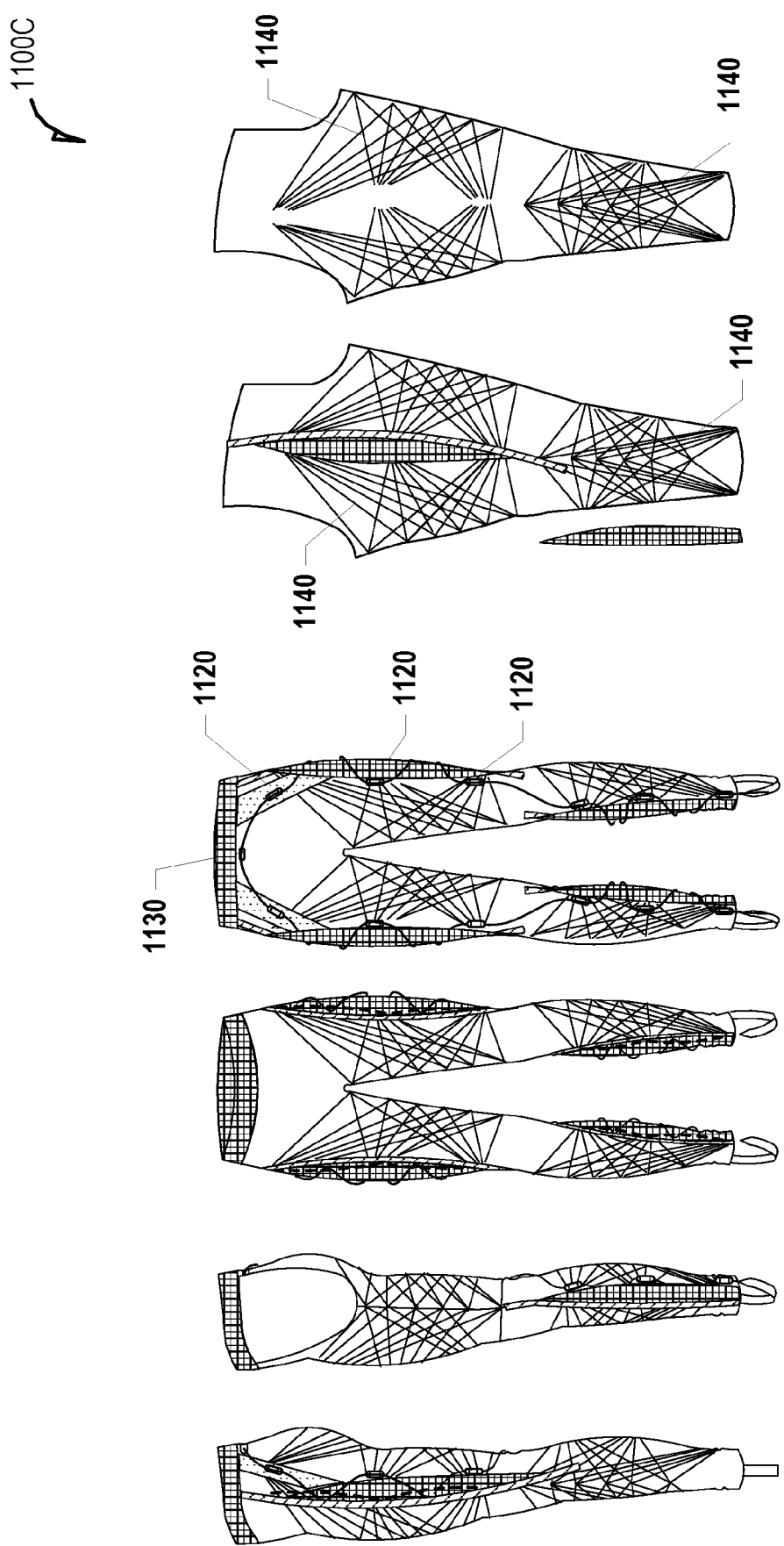
Figure 11D:
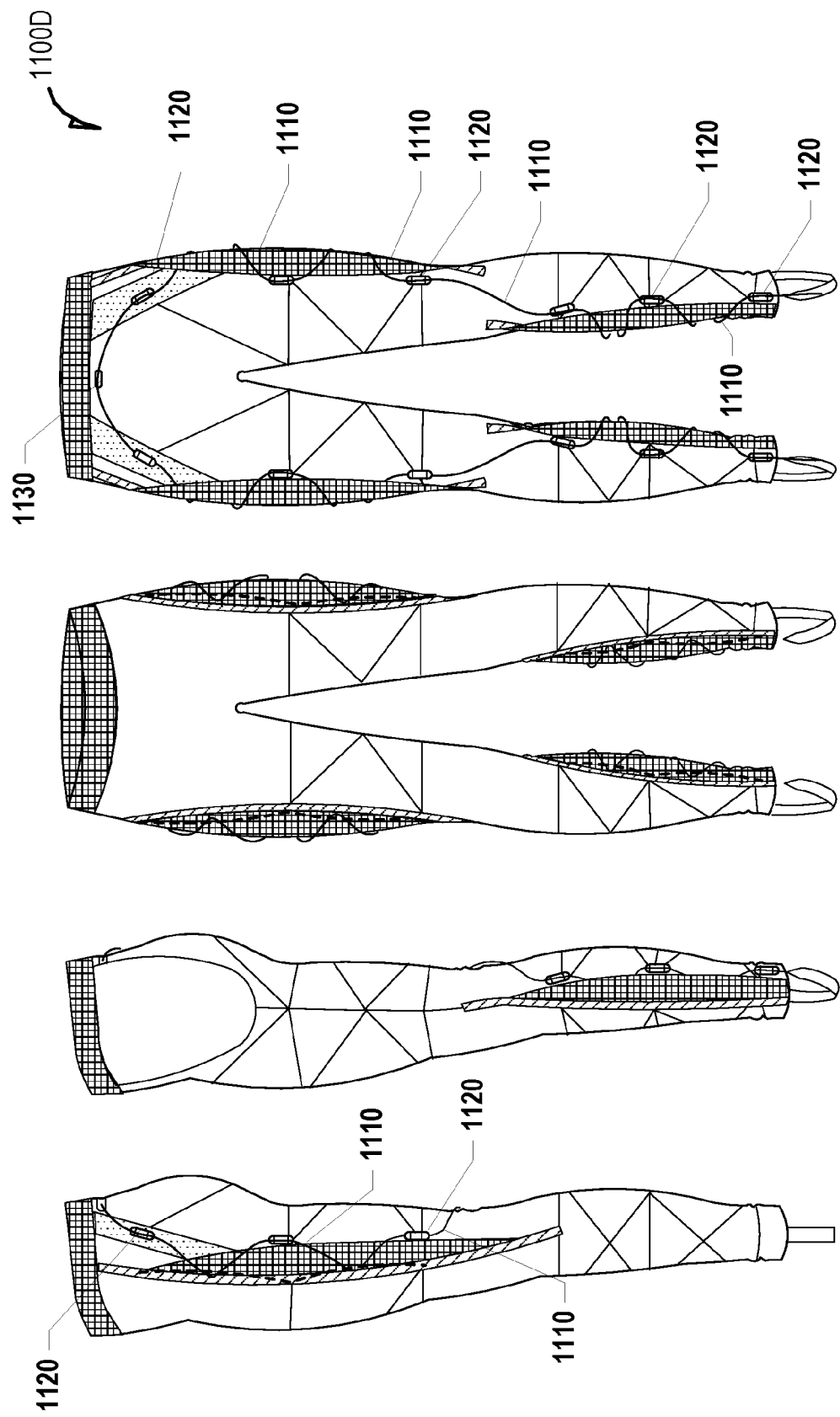

FIGS. 11B-11D illustrate alternative examples of adaptive tights that incorporate different fabric layouts as well as compression banding (e.g., horizontal bands of super stretch fabric (highly elastic fabric)). For example, adaptive tights 1100C, shown in FIG. 11C, include web-like compression bands integrated into the tights to enhance compression in the thigh and calf regions. Adaptive tights 1100D, shown in FIG. 11D, also include compression bands, but in a different pattern providing lower levels of compression. In these examples, the compression bands are aligned with guide tubes 1120 in at least some locations, which distributes forces from tension applied to the lace 1110 across a wider area of the garment.

Figure 11E:
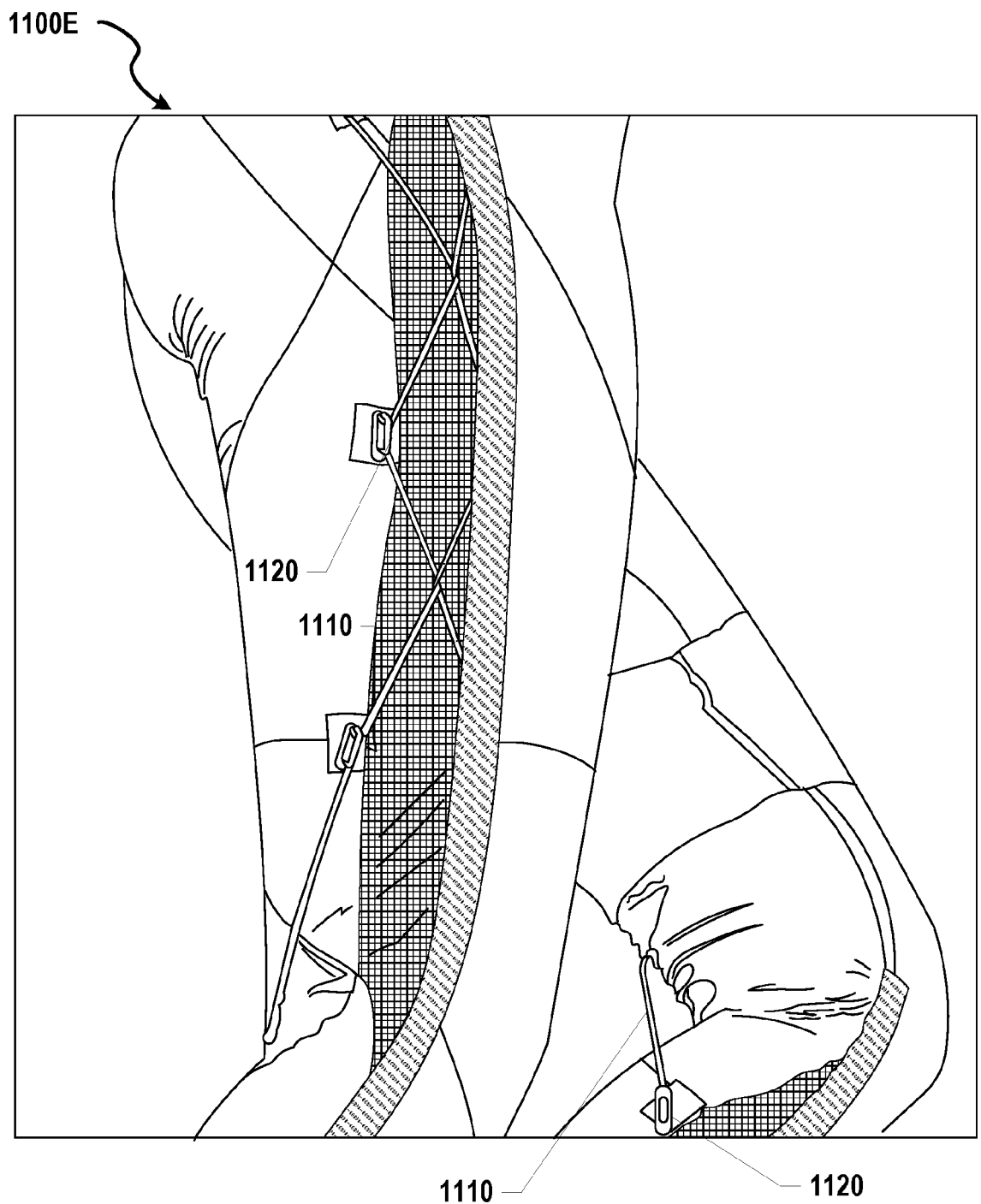

FIG. 11E illustrates an example adaptive tights in use. During activity, such as running, the lace 1110 is disengaged when the wearer's knee is bent, but fully engaged when the leg straightens, providing extra support to the muscle groups of the leg during a foot-strike of the corresponding foot and then disengaging during the upswing of the leg to provide freedom of motion. Accordingly, the support provided to the wearer fluctuates in correspondence with the running stride so that it activates to provide increased support to the leg during moments in a run when needed while permitted freedom of motion when less support us needed during the run cycle. In some examples, an adaptive engine can be engaged to increase the support fluctuations, further increasing support during high impact portions of the running stride. Changes in the support structure can also facilitate higher energy return to enhance a wearer's performance.

The benefit gained through the dynamic support described above is providing additional support during foot strike to provide increased support for leg masses, such as thighs or calves. The support is then disengaged after foot strike, during upswing of the leg, to provide freedom of movement as the leg swings back.

Compression Sleeves

Figure 12A:
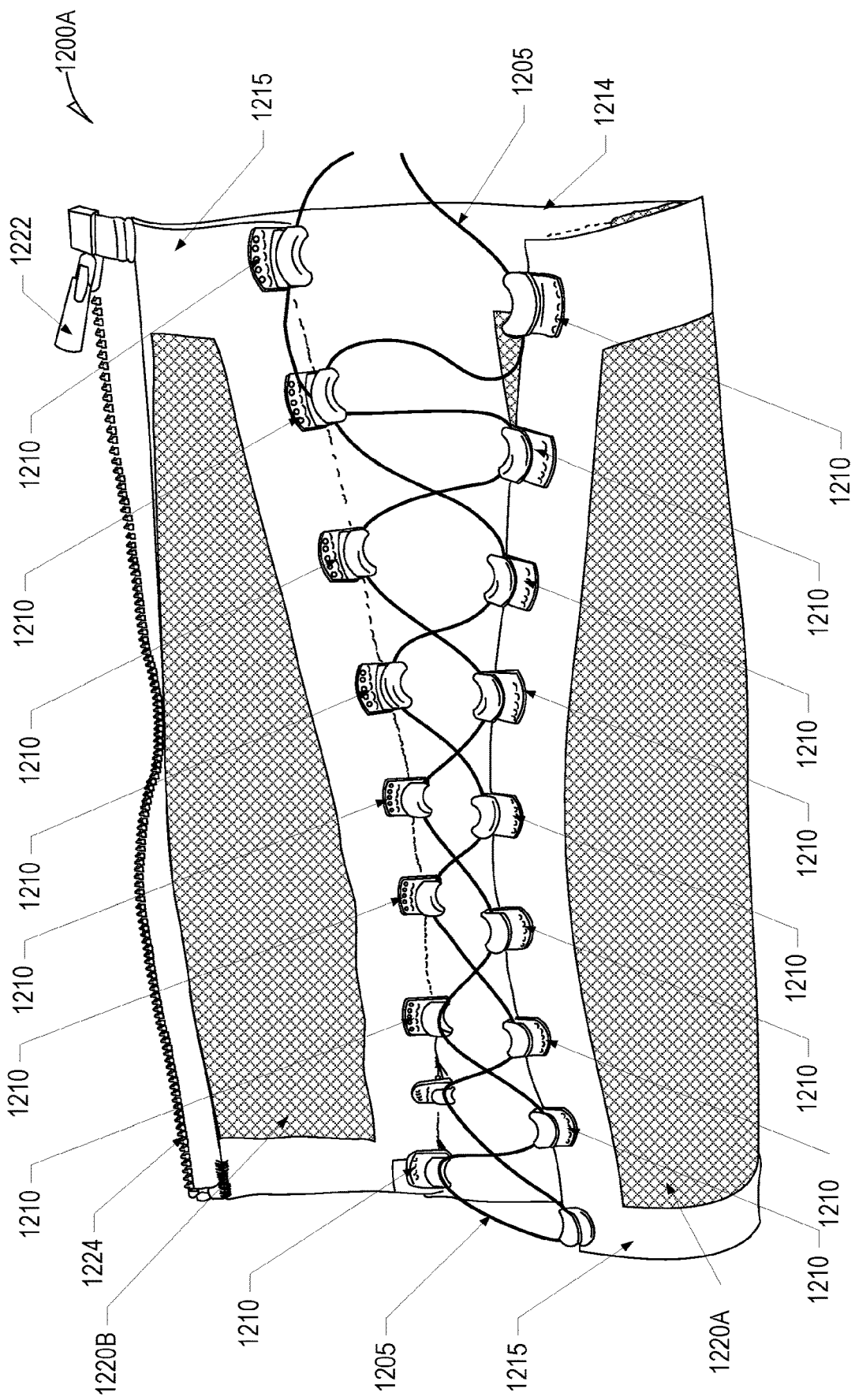
FIG. 12A is a line drawing depicting an adaptive sleeve, according to some example embodiments.

Sleeves can be used for support during a physical activity and to assist recovery after physical activity. As discussed here, sleeves can include legs sleeves, arm sleeves as well as tubular portions of other garments, such shirts, pants, tights, leggings, among others. FIG. 12A is a line drawing depicting an adaptive compression sleeve, according to some example embodiments. In this example, the adaptive compression sleeve 1200A includes a lace 1205 running in a crisscross pattern between a series of lace guides 1210 on either side of an adjustment zone (e.g., space between the lace guides). The compression sleeve 1200A also includes a zipper 1224 and zipper pull 1222 to assist in donning the compression sleeve by allowing for easy wrapping around the target anatomy, such as an upper or lower leg region. The zipper 1224 splits the compression sleeve 1200A into a first half 1220A and a second half 1220B, which are largely constructed of an elastic or inelastic mesh material. In this example, the first half 1220A and second half 1220B are also connected by an underlayer 1214, which is a layer of fabric spanning both halves and underneath the adjustment zone.

The example adaptive compression sleeve 1200A illustrated here is manually adjusted with lace 1205. However, the adaptive compression sleeve 1200A can have an adaptive adjustment engine integrated to provide automatic or semi-automatic adjustments. An automatic adaptive compression sleeve 1200B, as illustrated in FIGS. 12B-12E, can be programmed to detect, through acceleration or other information provided by an IMU as disclosed herein, an increase in physical activity of the wearer and respond by automatically increasing compression based on the level of activity detected.

Alternatively, the adaptive compression sleeve 1200B, discussed below, can be configured to assist with recovery by pulsing compression levels or progressively changing compression level and/or compression location throughout the length of the sleeve. In an example, the compression sleeve 1200B can pulsate compression and/or migrate compression location up and/or down the longitudinal length of the sleeve to enhance circulation and shorten recovery time. The adaptive compression sleeve 1200B is controlled by an application operating on a smartphone, smart watch, or discrete stand-along computing device that could be embedded within the sleeve or adaptive engine.

FIGS. 12B-12E are line drawings illustrating an adaptive compression/recovery sleeve 1200B including an adaptive engine 1230 to engage automatic adjustments, according to some example embodiments. In this example, the adaptive compression sleeve 1200B includes components such as: lace cable 1205, lace cable 1206, airbag 1208, lace guides 1210, lace return guides 1212, lace guide overlay 1215, longitudinal stiffeners 1216, mesh side panels 1220A/1220B (also referred to as first half 1220A and second half 1220B, and collectively referenced as mesh side panels 1220), and adaptive engine 1230. Adaptive sleeve 1200B also includes a flared distal end 1226, which is adapted to receive a portion of anatomy, such as a wearer's ankle. In certain examples, the adaptive sleeve 1200B includes a full-length zipper along the back-side (e.g., back of leg) to ease entry and exit from the sleeve.

Figure 12B:
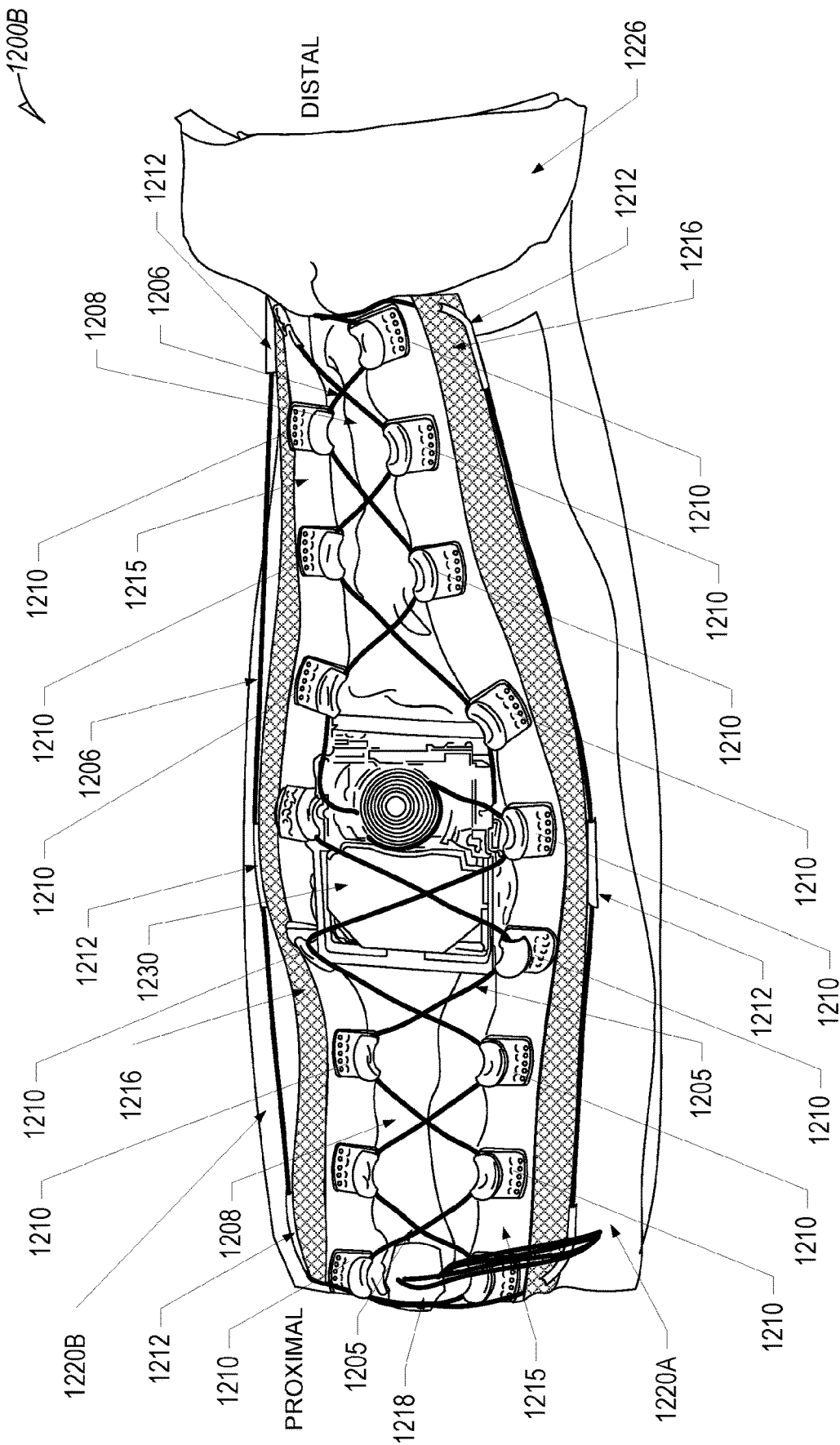
FIGS. 12B-12F are line drawings illustrating an adaptive sleeve including an adaptive engine to engage automatic adjustments, according to some example embodiments.

FIG. 12B illustrates a lower leg adaptive sleeve example in accordance with some embodiments. The adaptive sleeve 1200B distributes compression forces up and down the sleeve from the adaptive engine 1230 through a two-zone crisscross lacing patterning including lace cable 1205 and lace cable 1206 each running through a series of lace guides 1210. The lower (distal) lacing pattern formed by lace cable 1206 includes a return loop running along the outside of the lacing zone thought return guides 1212 back up to the top (proximal end) of the adaptive sleeve 1200B. The return loop assists in distributing pull forces more evenly throughout the sleeve. The lace cable 1205 and lace cable 1206 are both captured in a lace stop 1218 that allows for additional manual type adjustments. For example, the tension levels between lace cable 1205 and lace cable 1206 can be adjusted using the lace stop 1218 (also referred to as lace anchor 1218). Changing the relative tensions between lace cable 1205 and lace cable 1206 allows for the upper lacing zone (e.g., the zone controlled by lace cable 1205) to have different compression characteristics as compared to the lower lacing zone. The relative terms "upper", "up", or "top" are generally used to refer to a more proximal end of the adaptive sleeve 1200B, while "lower", "down", or "bottom" are generally used to refer to a more distal end of the adaptive sleeve 1200B. FIG. 12B includes references to Proximal and Distal to assist with orientation.

In this example, both lace cable 1205 and lace cable 1206 are fed into the adaptive engine 1230, which is disposed in the middle of adaptive sleeve 1200B. In other examples, multiple adaptive engines can be used to control individual lacing zones as needed to attain the desire compression throughout the sleeve. In this example, the lace cable 1205 loops through the adaptive engine 1230, engaging a lace spool within the adaptive engine as discussed above. From the adaptive engine 1230, the lace cable 1205 crisscrosses up the sleeve to the proximal end where it runs through the lace anchor 1218. The lace cable 1206 also loops through the adaptive engine 1230 engaging the lace spool in parallel with the lace cable 1205. From the adaptive engine 1230, the lace cable 1206 crisscrosses down the adaptive sleeve 1200B to the distal end where each end of lace cable 1206 runs around a perimeter of the lacing (e.g., adjustment zone) returning back to the proximal end via return guides 1212. In this example, the adjustment zone is defined by the boundaries of longitudinal stiffeners 1216. In other examples, the adjustment zone can be defined by other structures, such as the boundaries of lace guide overlays 1215. In this example, the return guides 1212 are formed from fabric loops or tunnels, as discussed above. In other examples, the return guides 1212 can be plastic lace guides or similar lace routing structures known in the art.

In this example, the lace guide overlays 2015 are longitudinal strips of reinforced fabric extending inward towards the throat from two longitudinal stiffeners 2016, with the throat being the open space between the series of lace guides running a majority of the longitudinal length of the adaptive sleeve 1200B. The longitudinal stiffeners 2016 assist the sleeve 1200B in retaining shape and in distributing lace cable loading more evenly to the mesh side panels 1220. The throat (not specifically labeled) is the area between the lace guide overlays 2015 that contains (or exposes) at least a portion of the airbag 1208. The airbag 1208 also functions to distribute lace cable forces and protect the shin of the wearer in this example. In this example, the airbag 1208 contains a fixed amount of air that is pre-filled, or is pumped up by the user as part of the donning process. A sleeve designed for use on the upper leg may not include an airbag 1208 as there is no hard anatomy to protect from point pressure created by the lacing of the sleeve (e.g., lace cable 1205 and lace cable 1206). In an alternative example, the airbag 1208 is replaced with a rigid or semi-rigid plastic shield that operates to distribute the lace forces.

Figure 12C:
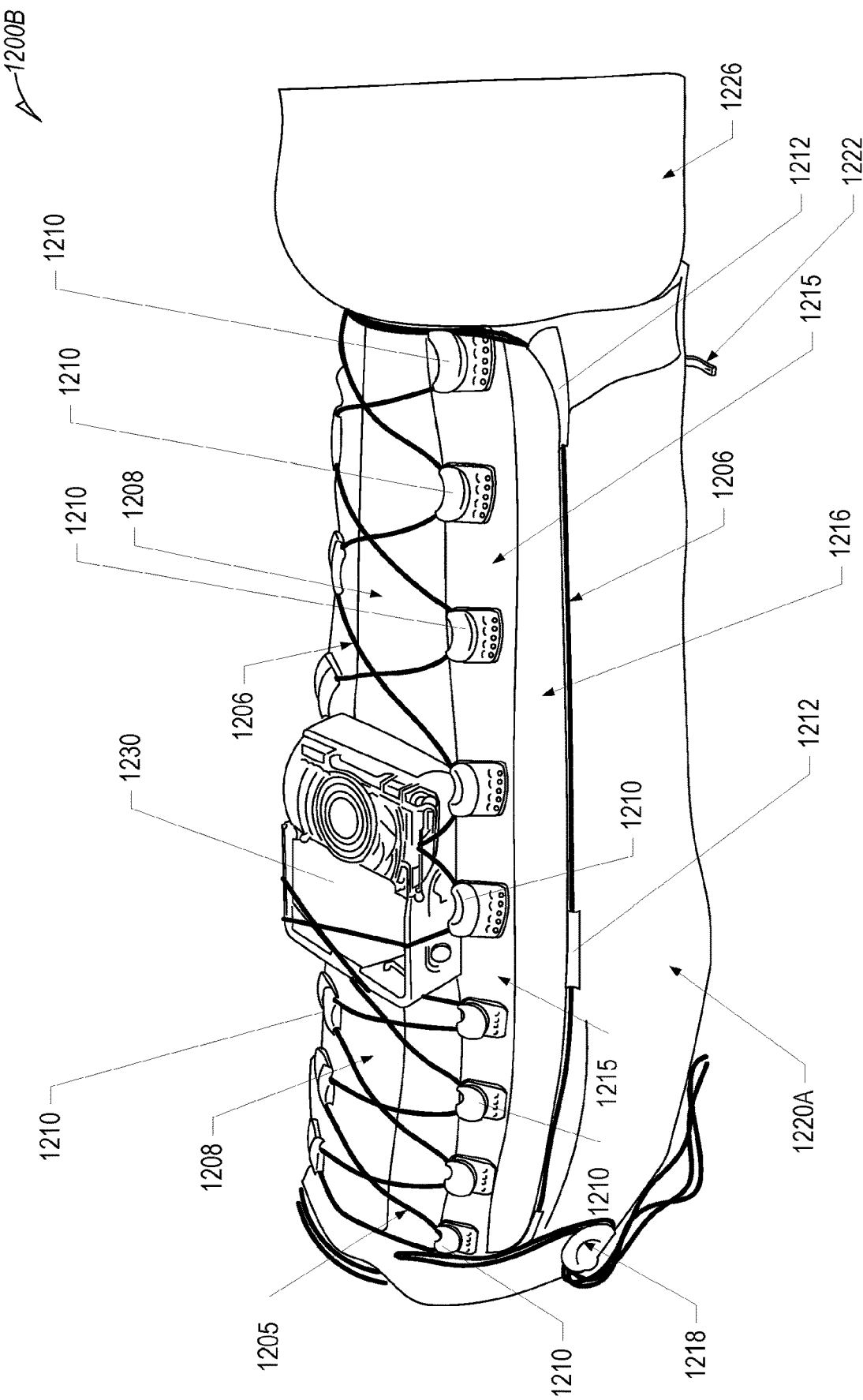

FIG. 12C is a side view line drawing illustration of the adaptive sleeve that better illustrates a portion of the lace return guides 1212 and return path of lace cable 1206. The side view also depicts how the lace return guides 1212 are positioned adjacent to a lateral edge of the longitudinal stiffener 1216. In this example, the longitudinal stiffener 2016 is a plastic-coated fabric material, in other examples the longitudinal stiffener 2016 is a rigid or semi-rigid structure embedded between layers of fabric (see FIG. 12E discussed below).

Figure 12D:
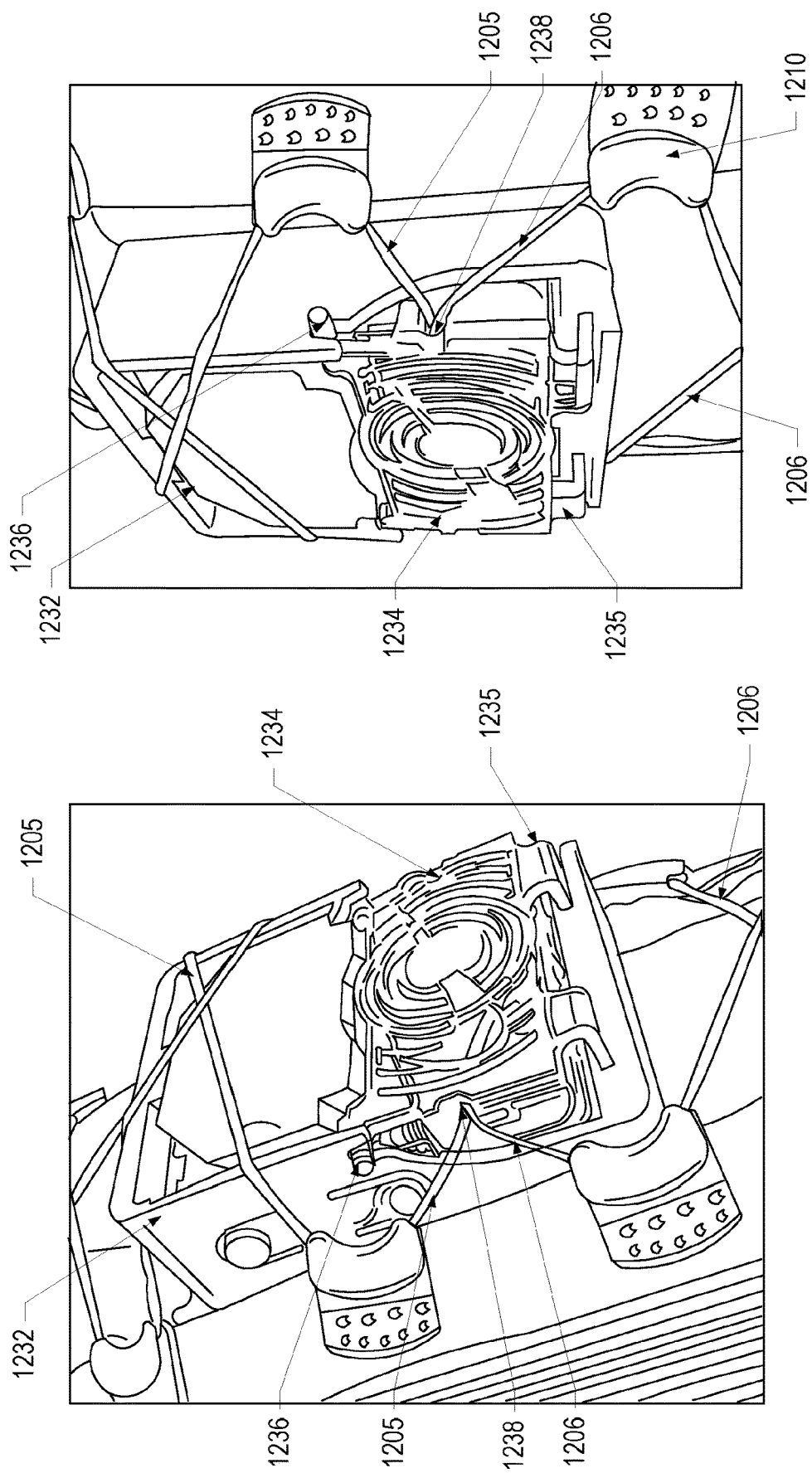

FIG. 12D illustrate aspects of an example adaptive engine 1230 integrated into an adaptive support sleeve 1200B. In these examples, the adaptive engine 1230 includes components such as a housing 1232, a lace spool lid 1234, lid latches 1235, lid hinges 1236, and lid lace guides 1238. As mentioned above, the adaptive engine 1230 is similar to the adaptive engine discussed above in reference to FIGS. 9A-9E, the following discusses a few adaptations made for this example adaptive compression sleeve.

The housing 1232 is designed to hold an adaptive engine, such as the one discussed above. The housing 1232 includes recesses (or cut-outs) to receive the lid hinges 1236 on either lateral side of the housing 1232. The lace spool lid 1234 also includes lid latches 1235 that engage complementary features on the housing 1232. In this example, the lid latches 1235 include beveled protrusions that snap into recesses in vertical walls of the housing 1232. The lace spool lid 1234 guides the lace cable into the lace spool within the adaptive engine 1230 to allow for automatic changes in the effective length of the lace cables (e.g., lace cable 1205 and lace cable 1206). The lace spool lid 1234 also includes lace guides 1238 on each lateral edge that guide the lace cable into position to engage the lace spool.

Figure 12E:
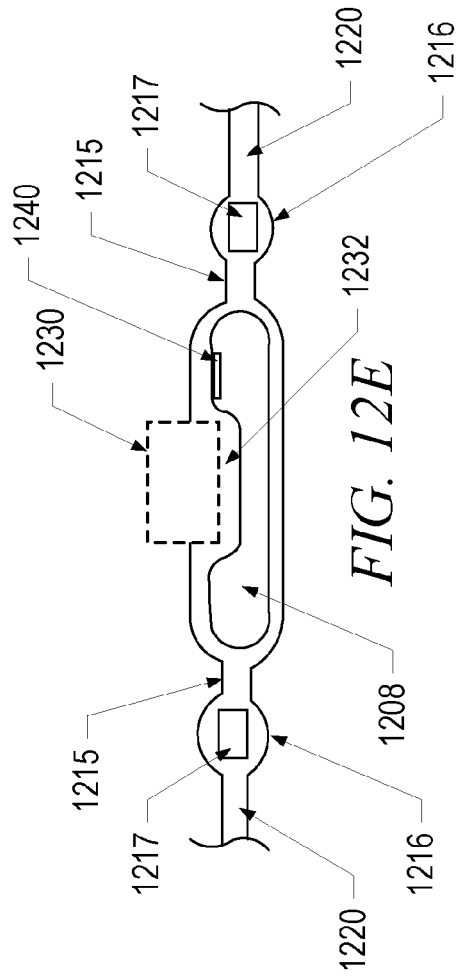

FIG. 12E is a line drawing illustrating a cross-sectional view of an adaptive compression sleeve, according to some example embodiments. In this example, the adaptive sleeve 1200B includes an airbag 1208, lace guide overlays 1215, longitudinal stiffeners 1216, rigid or semi-rigid batons 1217, mesh side panels 1220, adaptive engine 1230, notch 1232, and pressure sensor 1240. The cross-section of longitudinal stiffeners 1216 illustrates an example of the longitudinal stiffeners 1216 including rigid or semi-rigid batons 1217 sandwiched between layers of the adaptive sleeve 1200B. In some examples, the batons 1217 can be interchangeable through pockets formed in the longitudinal stiffeners 1216.

The cross-section view also illustrates an example cross-sectional shape of airbag 1208, which in this example includes notch 1232 to accommodate adaptive engine 1230. The notch 1232 may only occur in the area of the adaptive engine 1230. The airbag 1208 also includes pressure sensor 1240 that provides information on the air pressure within the airbag 1208, which can be used to determine compression being applied by the adaptive sleeve 1200B.

Figure 12F:
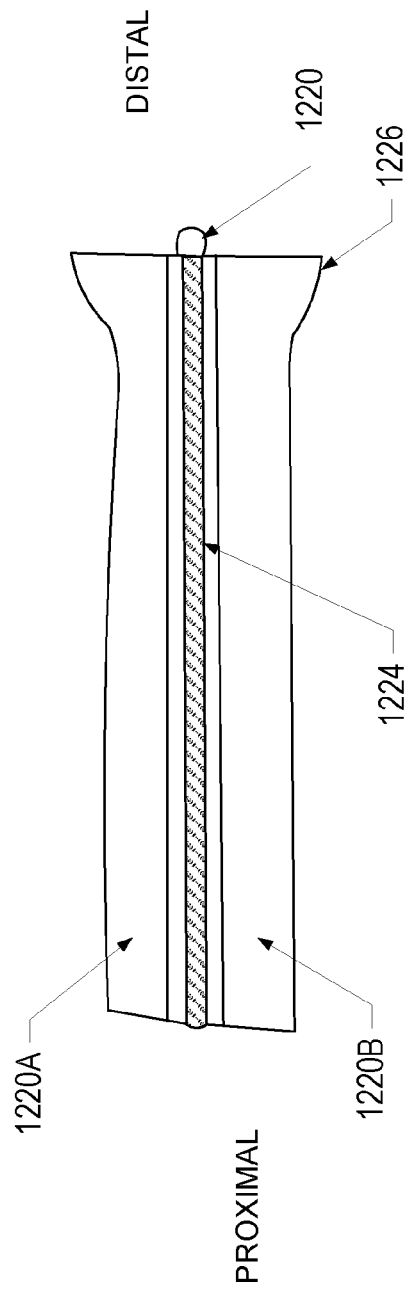

FIG. 12F is a line drawing illustrating a posterior view of adaptive sleeve 1200B, according to some example embodiments. In this example, the adaptive sleeve 1200B includes a longitudinal zipper, zipper 1224, running the length of the adaptive sleeve. The zipper 1224 includes a zipper pull 1222 and splits the mech side panels 1220 into a first half 1220A and a second half 1220B. The adaptive sleeve 1200B also includes a flared distal end 1226 that is adapted to received anatomy, such as a wearer's ankle.

Figure 12G:
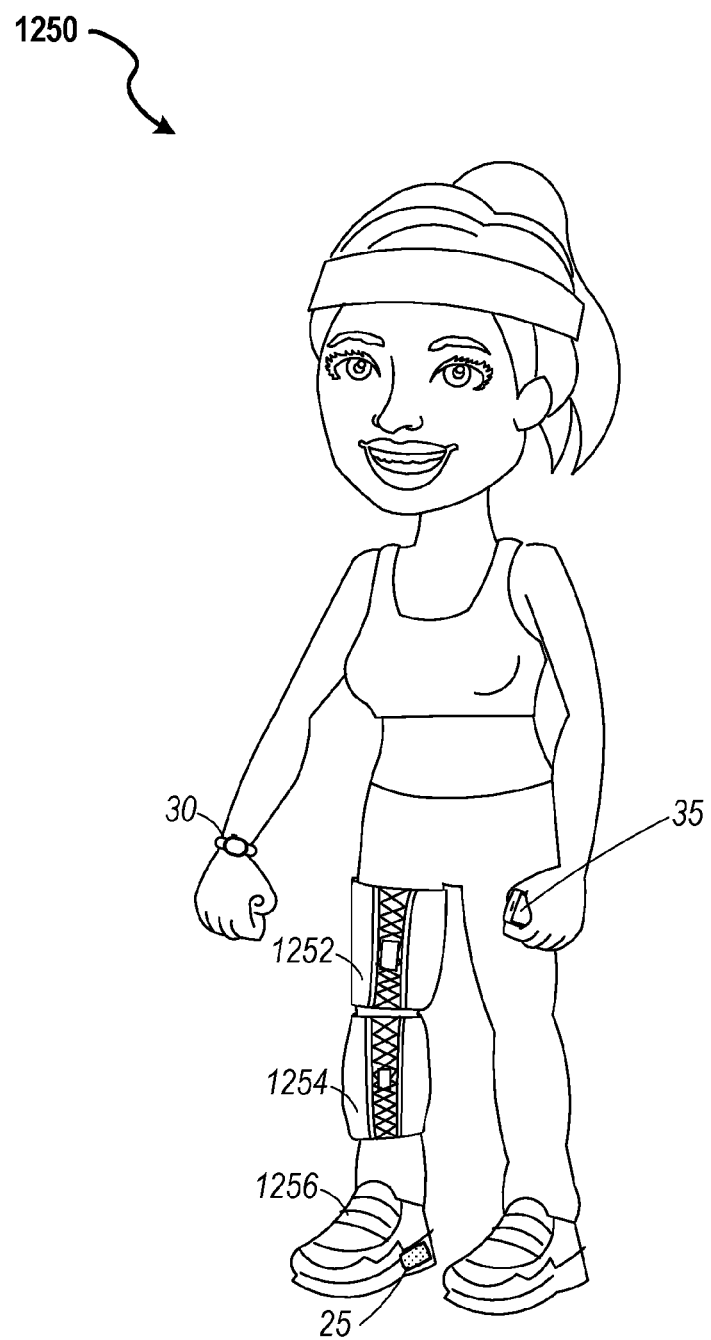
FIG. 12G is a line drawing illustrating multiple adaptive compression sleeves and a footwear assembly operating as a coordinated recovery system, according to some example embodiments.

FIG. 12G is a line drawing of a full-leg recovery system 1250 including multiple adaptive compression sleeves and a footwear assembly, according to some example embodiments. In this example, the recovery system 1250 includes an upper-leg adaptive compression sleeve 1252, a lower-leg adaptive compression sleeve 1254, and an adaptive footwear assembly 1256. The system is controlled through an application operating on a computing device, such as smart watch 30 or smartphone 35.

In this example, the adaptive compression sleeves and footwear assembly are configured to provide various levels of compression to facilitate recovery after an athletic activity. Compression and release of each adaptive device within the system 1250 can be controlled through an application with pre-programmed sequences and/or user defined routines. For example, the system 1250 can instruct the footwear assembly 1256 to compress, followed an adjustable number of seconds later by the lower-leg adaptive compression sleeve 1254, which is then followed by the upper-leg adaptive compression sleeve 1252. The sequence can be reversed, repeated, and/or rearranged as needed to accomplish the desired recovery regiment.

As discussed above, the adaptive engines controlling each adaptive compression device in the recovery system 1250 can communicate with a controller via wireless communications. The controller (e.g., smart watch 30 or smartphone 35 in these examples) can control the sequence of compression and release to correspond to pre-defined protocols or user generated sequences.

Figure 13A:
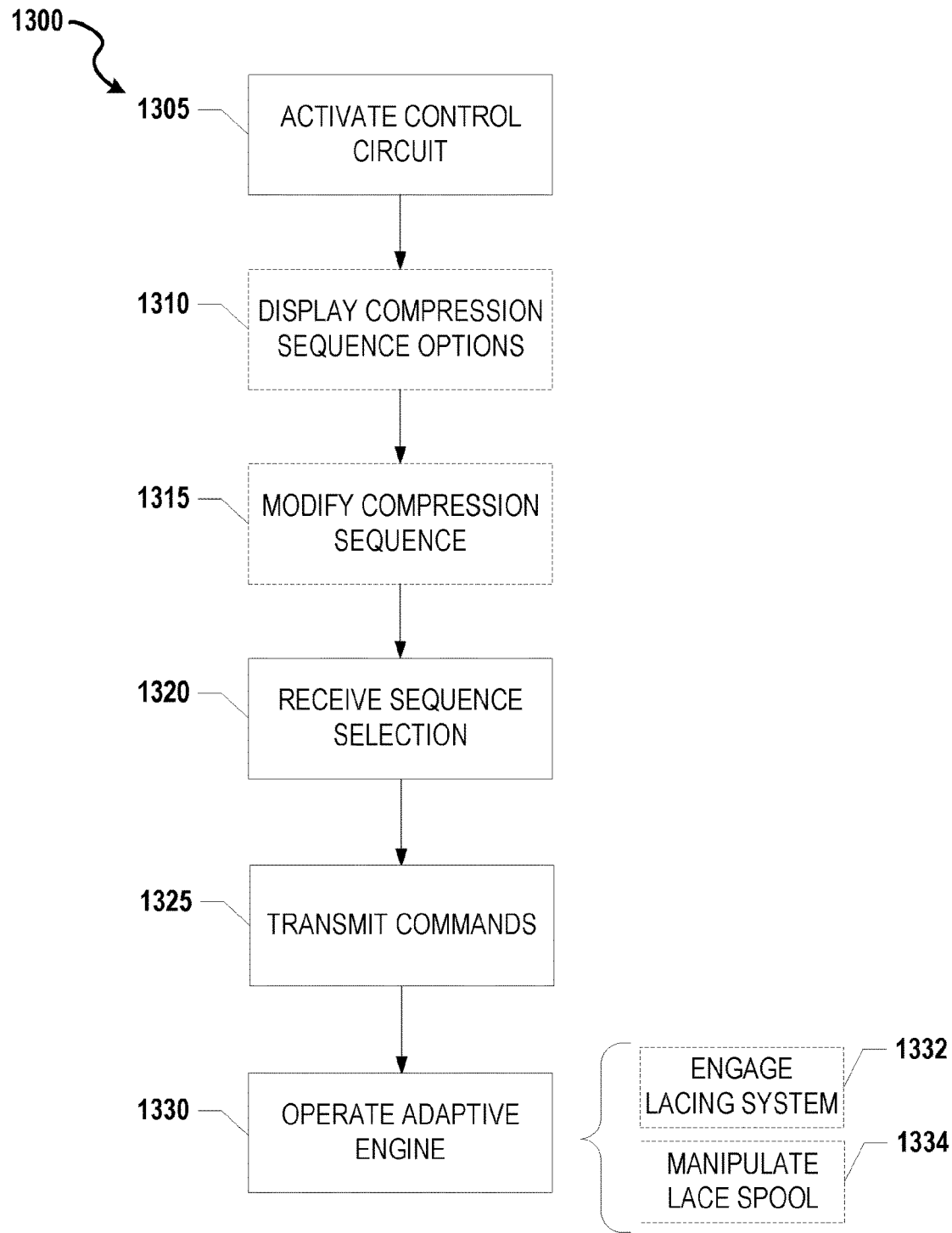
FIG. 13A is a flowchart illustrating a technique for operating an adaptive compression sleeve, according to some example embodiments.

FIG. 13A is a flowchart illustrating a technique for operating an adaptive compression garment, according to some example embodiments. In this example, the technique 1300 can include operations such as: activating the control circuit at 1305, receiving a sequence selection at 1320, transmitting commands at 1325, and operating an adaptive engine at 1330. Optionally, the technique 1300 can also include operations such as: displaying compression sequence options at 1310 and modifying compression sequence(s) at 1315. Additionally, in technique 1300 operating the adaptive engine can optionally include engaging a lacing system at 1332 and manipulating a lace spool at 1334.

In this example, the technique 1300 begins at 1305 with activation of a control circuit, such as control circuit 50. The control circuit is a dedicated collection of circuitry or an application operating on computing device, such as a wearable computing device. The control circuit operates the adaptive compression garment, such as adaptive compression sleeve 1200B discussed above. At 1310, the technique 1300 optionally continues with the control circuit generating a display of available compression sequences for selection by a user. The technique 1300 also optionally includes an operation to modify compression sequences at 1315. The control circuit can also generate a user interface that allows a user to modify or create a compression sequence. Compression sequences generally includes a series of compression and release commands with associated delays.

At 1320, the technique 1300 continues with the control circuit receiving a selection of a compression sequence. The selected compression sequence will be performed on the adaptive compression garment. At 1325, the technique 1300 continues with the control circuit transmitting commands to perform the selected compression sequence to an adaptive engine. The technique 1300 continues at 1330 with the adaptive engine operating to perform the received commands to perform the selected compression sequence. Operating the adaptive engine can include engaging a lacing system on the adaptive compression garment at 1332 and manipulating a lace spool within the adaptive engine to change an effective length of a lace cable within the lacing system. Change the effective length of one or more lacing cables engages or disengage the compression.

Figure 13B:
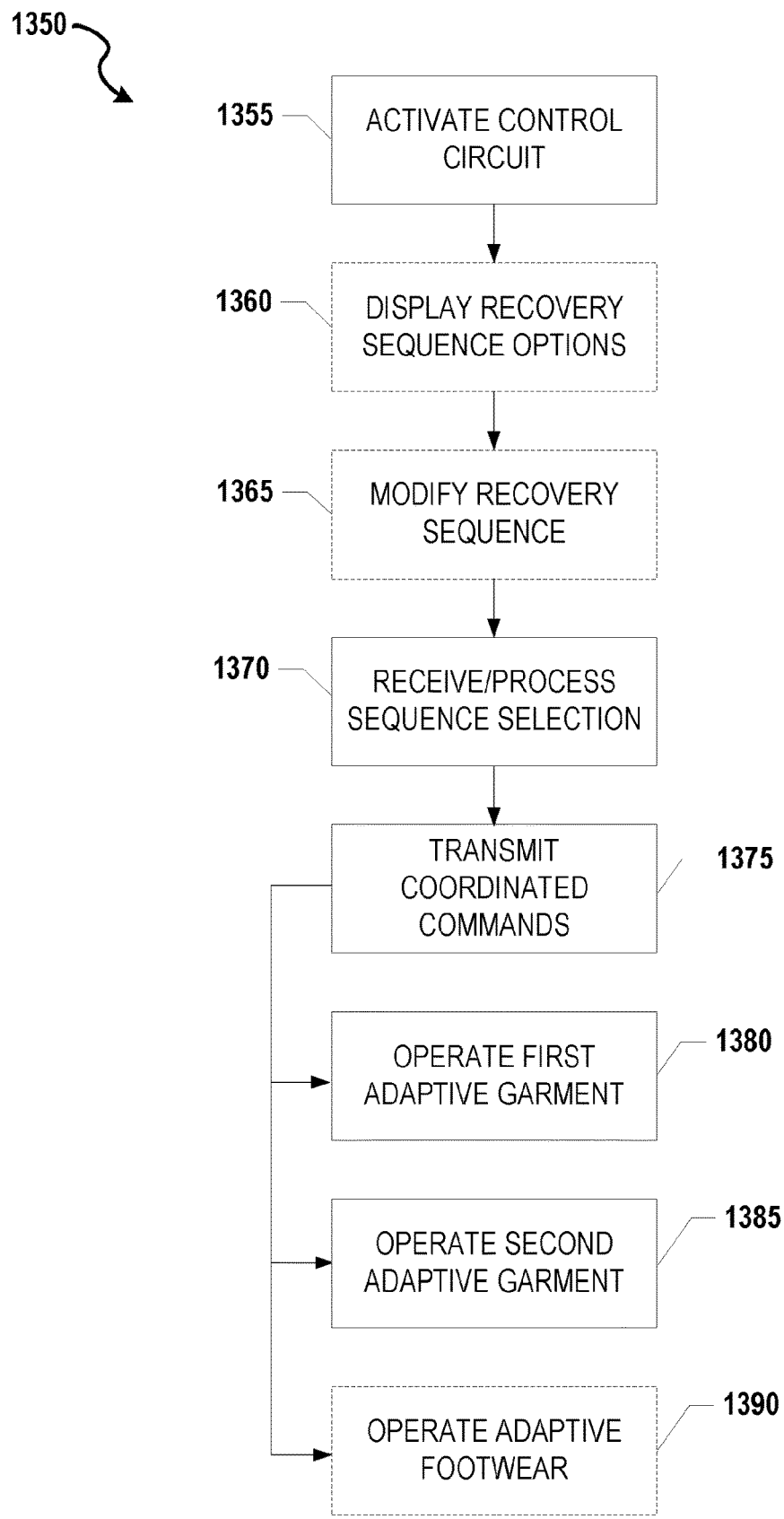
FIG. 13B is a flowchart illustrating a recovery technique using an adaptive compression recovery system, according to some example embodiments.

FIG. 13B is a flowchart illustrating a recovery technique using an adaptive compression recovery system, according to some example embodiments. The technique 1350 details an example of operating a recovery system including multiple adaptive compression garments, such discussed above in reference to FIG. 12G. In this example, the technique 1300B can include operations such as: activating the control circuit at 1355, receiving and/or processing a recovery sequence selection at 1370, transmitting coordinated commands at 1375, operating a first adaptive garment at 1380, operating a second adaptive garment at 1385, and optionally operating an adaptive footwear assembly at 1390. Optionally, the technique 1350 also includes operations such as: displaying recovery sequence options at 1360 and modifying or creating recovery sequences at 1365.

The technique 1350 begins at 1355 with activation of a control circuit, such as activation of an application operation on smart watch 30 or smartphone 35 that will control the adaptive compression garments in the system. At 1360, the technique 1350 optionally continues with the control circuit displaying recovery sequence options for selection by the user. The technique 1350 optionally continues at 1365 with the control circuit generating an interface that allows a user to modify or create recovery sequences. At 1370, the technique 1350 continues with the control circuit (e.g., application operating on smart watch 30 or smartphone 35) receiving and/or processing the selected recovery sequence. Processing the selected recovery sequence includes generating a series of coordinated commands to perform coordinated compression and release operations on the adaptive compression garments in the adaptive recovery system. The coordination between adaptive compression garments includes timing of operations, among other things.

At 1375, the technique 1350 continues with the control circuit transmitting the coordinated commands to each of the adaptive compression garments in the adaptive recovery system. The technique 1350 continues with coordinated operation of the first adaptive garment at 1380, the second adaptive garment at 1385, and optionally adaptive footwear at 1390. In an example, coordinated operation of the adaptive compression garments can include sequences such as compression of an adaptive footwear assembly 1256, followed X seconds later by compression of an adaptive compression sleeve 1254, followed X seconds later by compression of adaptive compression sleeve 1252. The example sequence can continue with release of adaptive compression sleeve 1252 followed by release of adaptive compression sleeve 1254 followed by release of adaptive footwear assembly 1256. Release of compression can include short delays between each release similar to the delay between compression. Sequences can include pulsing compression and other more complex interactions.

Figure 14:
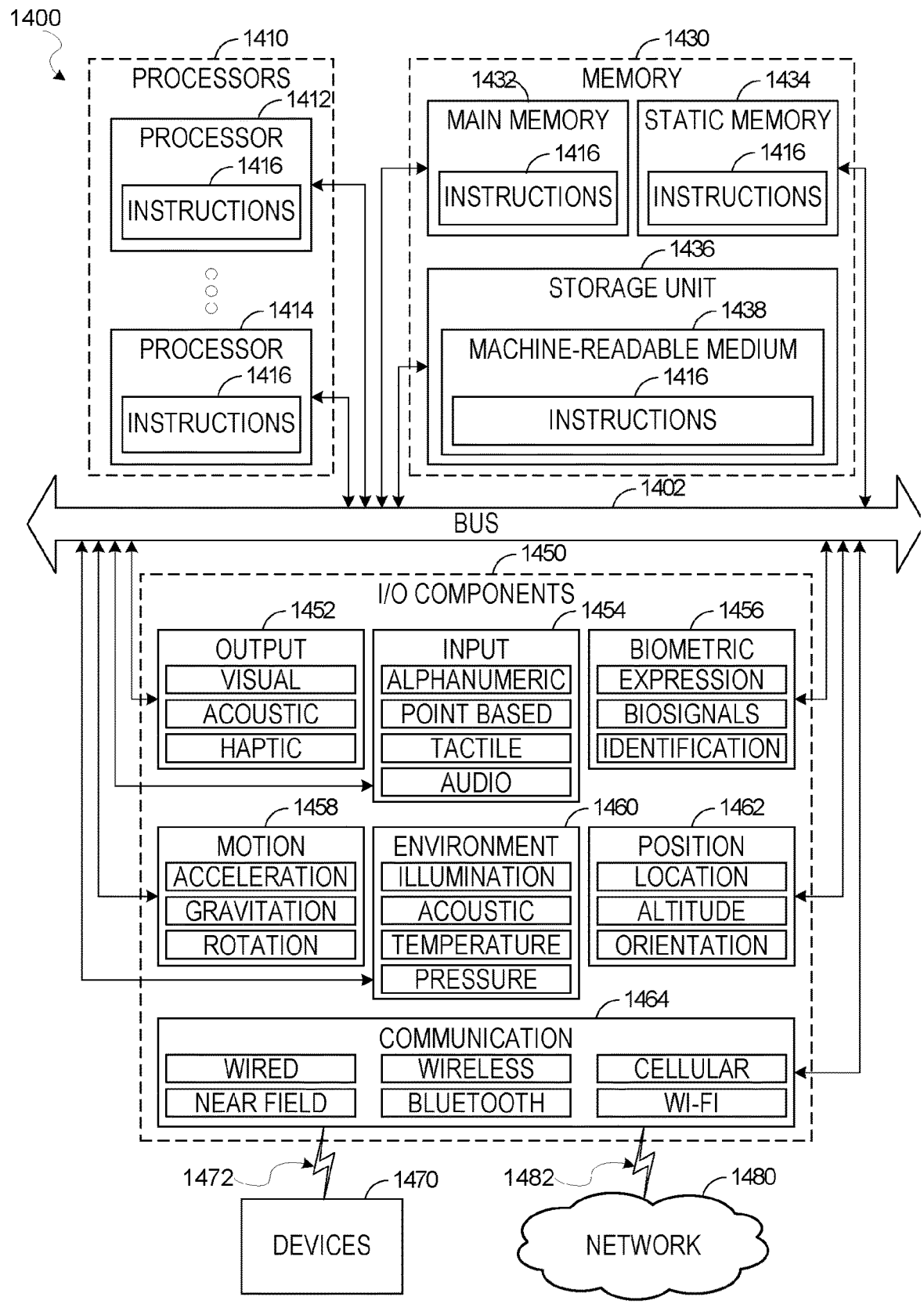
FIG. 14 is a block diagram illustrating an example computing device capable of performing aspects of the various techniques discussed herein.

FIG. 14 is a block diagram illustrating components of a machine 1300 (e.g., computing device), according to some example embodiments, able to read instructions from a machine-readable medium (e.g., a machine-readable storage medium) and perform any one or more of the methodologies (techniques) discussed herein. Specifically, FIG. 14 shows a diagrammatic representation of the machine 1400 in the example form of a computer system, within which instructions 1416 (e.g., software, a program, an application, an applet, an app, or other executable code) for causing the machine 1400 to perform any one or more of the methodologies discussed herein may be executed. For example, the instructions may cause the machine to execute the flow diagrams of FIGS. 1D, 12G, and 13. Additionally, or alternatively, the instructions implement aspects of the system 1 including the control circuit 50 as well as aspects of the adaptive engine 15. The instructions also implement functionality attributed to, or discussed as operating on, smart watch 30 or smartphone 35. The instructions transform the general, non-programmed machine into a particular machine programmed to carry out the described and illustrated functions in the manner described. In alternative embodiments, the machine 1400 operates as a standalone device or may be coupled (e.g., networked) to other machines. In a networked deployment, the machine 1400 may operate in the capacity of a server machine or a client machine in a server-client network environment, or as a peer machine in a peer-to-peer (or distributed) network environment. The machine 1400 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smart watch), a smart home device (e.g., a smart appliance), other smart devices, a web appliance, a network router, a network switch, a network bridge, or any machine capable of executing the instructions 1416, sequentially or otherwise, that specify actions to be taken by machine 1400. Further, while only a single machine 1400 is illustrated, the term "machine" shall also be taken to include a collection of machines 1400 that individually or jointly execute the instructions 1416 to perform any one or more of the methodologies discussed herein.

The machine 1400 may include processors 1410, memory 1430, and I/O components 1450, which may be configured to communicate with each other such as via a bus 1402. In an example embodiment, the processors 1410 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, processor 1412 and processor 1414 that may execute instructions 1416. The term "processor" is intended to include multi-core processor that may comprise two or more independent processors (sometimes referred to as "cores") that may execute instructions contemporaneously. Although FIG. 14 shows multiple processors, the machine 1400 may include a single processor with a single core, a single processor with multiple cores (e.g., a multi-core process), multiple processors with a single core, multiple processors with multiples cores, or any combination thereof.

The memory/storage 1430 may include a memory 1432, such as a main memory, or other memory storage, and a storage unit 1436, both accessible to the processors 1410 such as via the bus 1402. The storage unit 1436 and memory 1432 store the instructions 1416 embodying any one or more of the methodologies or functions described herein. The instructions 1416 may also reside, completely or partially, within the memory 1432, within the storage unit 1436, within at least one of the processors 1410 (e.g., within the processor's cache memory), or any suitable combination thereof, during execution thereof by the machine 1400. Accordingly, the memory 1432, the storage unit 1436, and the memory of processors 1410 are examples of machine-readable media.

As used herein, "machine-readable medium" means a device able to store instructions and data temporarily or permanently and includes, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 1416. The term "machine-readable medium" shall also be taken to include any medium, or combination of multiple media, that is capable of storing instructions (e.g., instructions 1416) for execution by a machine (e.g., machine 1400), such that the instructions, when executed by one or more processors of the machine 1400 (e.g., processors 1410), cause the machine 1400 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 1450 may include a wide variety of components to receive input, provide output, produce output, transmit information, exchange information, capture measurements, and so on. The specific I/O components 1450 that are included in a particular machine will depend on the type of machine. For example, portable machines such as mobile phones will likely include a touch input device or other such input mechanisms, while a headless server machine will likely not include such a touch input device. It will be appreciated that the I/O components 1450 may include many other components that are not shown in FIG. 14. The I/O components 1450 are grouped according to functionality merely for simplifying the following discussion and the grouping is in no way limiting. In various example embodiments, the I/O components 1450 may include output components 1452 and input components 1454. The output components 1452 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1454 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 1450 may include biometric components 1456, motion components 1458, environmental components 1460, or position components 1462 among a wide array of other components. In certain examples, the I/O components include sensors 25 discussed above. In an example, the biometric components 1456 may include components to detect expressions (e.g., hand expressions, facial expressions, vocal expressions, body gestures, or eye tracking), measure bio signals (e.g., blood pressure, heart rate, body temperature, perspiration, or brain waves), identify a person (e.g., voice identification, retinal identification, facial identification, fingerprint identification, or electroencephalogram based identification), and the like. The motion components 1458 may include acceleration sensor components (e.g., accelerometer), gravitation sensor components, rotation sensor components (e.g., gyroscope), and so forth. The environmental components 1460 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1462 may include location sensor components (e.g., a Global Position System (GPS) receiver component), altitude sensor components (e.g., altimeters or barometers that detect air pressure from which altitude may be derived), orientation sensor components (e.g., magnetometers), and the like. All of the different I/O components 1450 discussed herein can be integrated into system 1 discussed above and the data output from these various I/O components can be used within the adaptive support system techniques discussed in FIGS. 1D, 12G, and 13.

Communication may be implemented using a wide variety of technologies. The I/O components 1450 may include communication components 1464 operable to couple the machine 1400 to a network 1480 or devices 1470 via coupling 1482 and coupling 1472 respectively. For example, the communication components 1464 may include a network interface component or other suitable device to interface with the network 1480. In further examples, communication components 1464 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1470 may be another machine or any of a wide variety of peripheral devices (e.g., a peripheral device coupled via a Universal Serial Bus (USB)).

Moreover, the communication components 1464 may detect identifiers or include components operable to detect identifiers. For example, the communication components 1464 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1464, such as, location via Internet Protocol (IP) geo-location, location via Wi-Fi® signal triangulation, location via detecting an NFC beacon signal that may indicate a particular location, and so forth.

Transmission Medium

In various example embodiments, one or more portions of the network 1480 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 1480 or a portion of the network 1480 may include a wireless or cellular network and the coupling 1482 may be a Code Division Multiple Access (CDMA) connection, a Global System for Mobile communications (GSM) connection, or other type of cellular or wireless coupling. In this example, the coupling 1482 may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions 1416 may be transmitted or received over the network 1480 using a transmission medium via a network interface device (e.g., a network interface component included in the communication components 1464) and utilizing any one of a number of well-known transfer protocols (e.g., hypertext transfer protocol (HTTP)). Similarly, the instructions 1416 may be transmitted or received using a transmission medium via the coupling 1472 (e.g., a peer-to-peer coupling) to devices 1470. The term "transmission medium" shall be taken to include any intangible medium that is capable of storing, encoding, or carrying instructions 1416 for execution by the machine 1400, and includes digital or analog communications signals or other intangible medium to facilitate communication of such software.

Additional Notes

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The disclosure, therefore, is not to be taken in a limiting sense, and the scope of various embodiments includes the full range of equivalents to which the disclosed subject matter is entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

Each of these non-limiting examples can stand on its own, or can be combined in various permutations or combinations with one or more of the other examples.

Example 1 is an adaptive support garment configured to support a portion of anatomy, the adaptive support garment comprising: an adaptive support structure integrated into the adaptive support garment and configured to adjust a portion of the adaptive support garment; and an adaptive engine coupled to the adaptive support structure to activate adjustment of the portion of the adaptive support garment.

In Example 2, the subject matter of Example 1 includes, wherein the adaptive support structure includes a lacing system.

In Example 3, the subject matter of Examples 1 and 2 includes, wherein the lacing system includes a lace cable routed through a plurality of lace guides to adjust the portion of the adaptive support garment.

In Example 4, the subject matter of Examples 1-3 includes, wherein the adaptive engine operates to adjust an effective length of the lace cable.

In Example 5, the subject matter of Examples 1-4 includes, wherein the adaptive engine includes a motor and a control system to automatically or semi-automatically adjust the adaptive support structure.

In Example 6, the subject matter of Examples 1-5 includes, a sensor positioned relative to the portion of anatomy to monitor a parameter of the portion of anatomy.

In Example 7, the subject matter of Example 6 includes, wherein the sensor monitors a parameter indicative of at least one of the following parameters of the portion of anatomy: displacement; acceleration; velocity; and movement.

In Example 8, the subject matter of Examples 1-7 includes, wherein the adaptive engine includes a motor and a control system, the control system configured to control the motor in response to information received from the sensor.

In Example 9, the subject matter of Examples 1-8 includes, wherein the adaptive support garment is a bra including shoulder straps, breast contacting surfaces, and an under-band.

In Example 10, the subject matter of Examples 1-9 includes, wherein the adaptive support structure includes lacing coupled to at least one of the shoulder straps, the breast contacting surfaces and the under-band.

In Example 11, the subject matter of Examples 1-10 includes, wherein the adaptive support structure includes a posterior lacing system coupled to a right-wing portion and a left-wing portion to provide gore compression.

In Example 12, the subject matter of Examples 1-11 includes, wherein the posterior lacing system includes a crisscross lacing pattern running between the right-wing portion and the left-wing portion of the bra.

In Example 13, the subject matter of Examples 1-12 includes, wherein the posterior lacing system includes lacing coupled to a posterior base of the shoulder straps.

In Example 14, the subject matter of Examples 1-13 includes, wherein the posterior lacing system includes lacing extending over the shoulder straps and coupled to a superior portion of the breast contacting surfaces.

In Example 15, the subject matter of Examples 1-14 includes, wherein the adaptive support structure includes lacing coupled to the under-band.

In Example 16, the subject matter of Examples 1-15 includes, wherein the adaptive support structure includes an anterior lacing system extending between the breast contacting surfaces.

In Example 17, the subject matter of Examples 1-16 includes, wherein the anterior lacing system includes lacing creating a crisscross lacing pattern between a plurality of lace guides along a central edge of each breast contacting surface of the breast contacting surfaces.

In Example 18, the subject matter of Example 1-17 includes, wherein the anterior lacing system includes lacing extending through lace guides disposed on a portion of each shoulder strap of the shoulder straps.

In Example 19, the subject matter of Examples 1-18 includes, wherein the adaptive support structure includes a lacing system routed through a plurality of lace guides positioned adjacent to the portion of the adaptive support garment.

In Example 20, the subject matter of Examples 1-19 includes, wherein at least a portion of the plurality of lace guides include a pulley to route a portion of the lacing system.

Example 21 is an adaptive support garment configured to support a portion of anatomy, the adaptive support garment comprising: an adaptive support structure integrated into the adaptive support garment and configured to adjust a portion of the adaptive support garment; and an adaptive engine including a motor and a control system, the adaptive engine coupled to the adaptive support structure to automatically adjust the portion of the adaptive support garment.

Example 22 is an adaptive support system comprising: an adaptive support garment configured to support a portion of anatomy; an adaptive support structure integrated into the adaptive support garment, the adaptive support structure configured to adjust a first portion of the adaptive support garment relative to a second portion of the adaptive support garment; a sensor positioned relative to the portion of anatomy to monitor a parameter associated with the portion of anatomy; and an adaptive engine coupled to the adaptive support structure to adjust the first portion of the adaptive support garment based at least in part on data received from the sensor.

Example 23 is an adaptive support apparel system comprising: an activity sensor monitoring activity of a user; an adaptive support garment including an adaptive support system integrated into the adaptive support garment and an adaptive engine coupled to the adaptive support system to automatically adjust a portion of the adaptive support garment through manipulation of the adaptive support system; and a control circuit configured to send commands to the adaptive engine in response to input received from the activity sensor.

In Example 24, the subject matter of Example 23 includes, wherein the control circuit is configured to select a pre-defined activity classification based on data received from the activity sensor.

In Example 25, the subject matter of Examples 23 and 24 includes, wherein the pre-defined activity classifications include high impact and comfort.

In Example 26, the subject matter of Examples 23-25 includes, wherein the control circuit is further configured to determine a support level based on the selected pre-defined activity classification.

In Example 27, the subject matter of Examples 23-26 includes, wherein the adaptive engine adjusts the adaptive support system based on control commands received from the control circuit corresponding to the determined support level.

In Example 28, the subject matter of Examples 23-27 includes, wherein the activity sensor is embedded within a footwear assembly.

In Example 29, the subject matter of Examples 23-28 includes, wherein the activity sensor is configured to detect foot strike activity.

In Example 30, the subject matter of Examples 23-29 includes, wherein the control circuit is configured to receive foot strike activity data from the activity sensor and calculate a pre-defined activity classification based on the foot strike activity data.

In Example 31, the subject matter of Examples 23-30 includes, wherein the activity sensor is an inertial measurement unit (IMU).

In Example 32, the subject matter of Examples 23-31 includes, wherein the activity sensor is embedded within the adaptive support garment.

In Example 33, the subject matter of Examples 23-32 includes, wherein the activity sensor is configured to detect soft tissue movement.

In Example 34, the subject matter of Examples 23-33 includes, wherein the adaptive support garment is a bra and the activity sensor is disposed within a portion of a breast contacting surface.

In Example 35, the subject matter of Examples 23-34 includes, wherein the adaptive support garment is a bra and the activity sensor is disposed within a shoulder strap.

In Example 36, the subject matter of Examples 23-35 includes, wherein the activity sensor includes at least one of the following: an accelerometer; a gyroscope; a magnetometer; a global positioning sensor (GPS); a heart rate monitor; a temperature sensor; and a strain gauge.

In Example 37, the subject matter of Examples 23-36 includes, wherein the control circuit is disposed within a computing device including a display and a communication circuit.

In Example 38, the subject matter of Examples 23-37 includes, wherein the communication circuit is configured to send commands to the adaptive engine wirelessly.

In Example 39, the subject matter of Examples 23-38 includes, wherein the computing device is one of a smart watch, a smartphone, or a heart rate monitor.

In Example 40, the subject matter of Examples 23-39 includes, wherein the adaptive support system includes lacing connecting separate portions of the adaptive support garment, wherein the lacing is adjustable to alter relative positions of the separate portions of the adaptive support garment to produce different support characteristics.

In Example 41, the subject matter of Examples 23-40 includes, wherein the adaptive support system includes a plurality of lace guides to route the lacing through the separate portions of the adaptive support garment.

In Example 42, the subject matter of Examples 23-41 includes, wherein at least one segment of the lacing is coupled to a lace spool component of the adaptive engine to enable the adaptive engine to alter an effective length of the lacing.

In Example 43, the subject matter of Examples 23-42 includes, wherein the control circuit is configured to analyze data received from the activity sensor to determine whether to adjust the adaptive support system integrated into the adaptive support garment.

In Example 44, the subject matter of Examples 23-43 includes, wherein upon determining that an adjustment to the adaptive support system is needed, sending an adjustment command to the adaptive engine to perform the adjustment.

Example 45 is an adaptive support apparel system comprising: an activity sensor monitoring a parameter indicative of an activity level of a user; an adaptive support garment including an adaptive support system integrated into the adaptive support garment and an adaptive engine coupled to the adaptive support system to adjust a first portion of the adaptive support garment relative to a second portion of the adaptive support garment through manipulation of the adaptive support system; and a control circuit configured to send commands to the adaptive engine in response to input received from the activity sensor.

Example 46 is an adaptive support apparel system comprising: an adaptive support garment including an adaptive support system integrated into the adaptive support garment and an adaptive engine coupled to the adaptive support system to adjust a first portion of the adaptive support garment relative to a second portion of the adaptive support garment through manipulation of the adaptive support system; and a control circuit configured to control the adaptive engine in response to input received indicative of an activity level of a user.

In Example 47, the subject matter of Example 46 includes, a wearable computing device including a user interface configured to accept inputs indicative of the activity level of the user; and wherein the control circuit is configured to receive the activity level from the wearable computing device.

In Example 48, the subject matter of Examples 46-47 includes, an activity sensor monitoring activity of the user;

and wherein the control circuit is configured to process input received from the activity sensor to control the adaptive engine.

In Example 49, the subject matter of Examples 46-48 includes, wherein the control circuit sends pre-defined support level commands to the adaptive engine based on the input received from the activity sensor.

In Example 50, the subject matter of Examples 46-49 includes, selecting a pre-defined activity classification based on the activity level data received from the activity sensor.

In Example 51, the subject matter of Examples 46-50 includes, wherein the pre-defined activity classification is selected from a group of activity levels including: low exertion, moderate exertion, elevated exertion, and high exertion.

In Example 52, the subject matter of Examples 46-51 includes, determining a support level based on the selected pre-defined activity classification.

In Example 53, the subject matter of Examples 46-52 includes, wherein the adjusting the portion of the adaptive support garment is based on control commands received from the control circuit corresponding to the determined support level.

In Example 54, the subject matter of Examples 46-53 includes, wherein the activity level data is received by the control circuit over a wireless communication link with a footwear assembly housing the activity sensor.

In Example 55, the subject matter of Examples 46-54 includes, extracting foot strike activity from the activity level data from the activity sensor.

In Example 56, the subject matter of Examples 46-55 includes, calculating a pre-defined activity classification based on the foot strike activity extracted from the activity level data.

In Example 57, the subject matter of Examples 46-56 includes, calculating an activity level based on activity level data from the activity sensor including at least one of acceleration data, angular rate data, and orientation data.

In Example 58, the subject matter of Examples 46-57 includes, selecting a pre-defined activity classification based on the calculated activity level.

In Example 59, the subject matter of Examples 46-57 includes, wherein the automatically adjusting the portion of the adaptive support garment is based at least in part on the calculated activity level.

In Example 60, the subject matter of Examples 46-59 includes, wherein the activity level data is received by the control circuit over a communication link with the adaptive support garment containing the activity sensor.

In Example 61, the subject matter of Examples 46-60 includes, wherein receiving the activity level data includes receiving soft tissue movement data from the activity sensor embedded in the adaptive support garment.

In Example 62, the subject matter of Example 46-61 includes, wherein the activity level data is received by the control circuit over a communication link with a heart rate monitor, and wherein receiving the activity level data includes receiving heart rate data.

In Example 63, the subject matter of Examples 46-62 includes, wherein the activity level data is received by the control circuit over a communication link with a global positioning sensor (GPS), and wherein receiving the activity level data includes receiving at least one of position data, velocity data, and acceleration data.

In Example 64, the subject matter of Examples 46-63 includes, wherein automatically adjusting the portion of the adaptive support garment includes manipulating a lacing system connecting separate portions of the adaptive support garment, wherein the lacing system is adjustable to alter relative positions of the separate portions of the adaptive support garment to produce different support characteristics.

In Example 65, the subject matter of Examples 46-64 includes, wherein manipulating the lacing system includes operating the adaptive engine to change an effective length of at least a portion of the lacing system.

In Example 66, the subject matter of Examples 46-65 includes, wherein operating the adaptive engine to change the effective length includes rotating a lace spool coupled to the portion of the lacing system.

Example 67 is a method of dynamically adapting a support apparel system including an adaptive support garment, and a control circuit, the method comprising: receiving, at the control circuit, an activity level indicator; sending control commands to an adaptive engine integrated into the adaptive support garment; and automatically, in response to the control commands, adjusting a portion of the adaptive support garment based on the adaptive engine manipulating an adaptive support structure within the adaptive support garment.

In Example 68, the subject matter of Example 67 includes, monitoring an activity level of a user with an activity sensor; and wherein receiving the activity level indicator includes receiving activity level data generated by the activity sensor.

In Example 69, the subject matter of Examples 67-68 includes, wherein receiving the activity level indicator includes receiving a support level selection from the control circuit.

In Example 70, the subject matter of Examples 67-69 includes, wherein the support level selection is obtained from input received by the control circuit from a user interface adapted to receive input from a wearer.

In Example 71, the subject matter of Examples 67-70 includes, wherein receiving the activity level indicator includes: receiving activity data from an activity sensor disposed within a footwear assembly; and processing, on the control circuit, the activity data to determine the activity level indicator.

In Example 72, the subject matter of Examples 67-71 includes, extracting one or more step metrics from the activity level data from the activity sensor.

In Example 73, the subject matter of Examples 67-72 includes, calculating the activity level indicator based on the one or more step metrics extracted from the activity level data.

In Example 74, the subject matter of Examples 67-73 includes, wherein sending the control commands includes determining a support level for the adaptive support garment based on the activity level indicator.

Example 75 is an adaptive support garment comprising: a support structure configured to wrap around a portion of anatomy of a wearer and provide compression on the portion of anatomy; a plurality of lace guides disposed on the support structure; a lace cable, extending through the lace guides to form a lacing pattern over a lacing region of the support structure and around a portion of a perimeter of the portion of the support structure; and an adaptive engine coupled to the support structure and engaged with the lace cable, wherein the adaptive engine is configured to increase or decrease tension on the lace cable to increase or decrease compression of the support structure, respectively.

In Example 76, the subject matter of Example 75 includes, wherein the lacing pattern includes routing the lace cable completely around the perimeter of the lacing region of the support structure.

In Example 77, the subject matter of Examples 75-76 includes, wherein the lace guides include a plurality of tubular lace guides positioned along the perimeter and wherein the lace cable extends through the tubular lace guides.

In Example 78, the subject matter of Examples 75-77 includes, wherein the adaptive engine is positioned within the lacing region of the support structure.

In Example 78, the subject matter of Examples 75-78 includes, wherein the adaptive engine is positioned over a center point of the lacing region of the support structure.

In Example 80, the subject matter of Examples 75-79 includes, wherein the lace cable extends from opposing sides of the adaptive engine.

In Example 81, the subject matter of Examples 75-80 includes, wherein the lace cable forms a crisscross pattern across the lacing region of the support structure above and below the adaptive engine.

In Example 82, the subject matter of Examples 75-81 includes, wherein the lace cable is secured outside of the perimeter.

In Example 83, the subject matter of Examples 75-82 includes, an anchor secured to the support structure, wherein the lace cable is secured to the anchor.

In Example 84, the subject matter of Examples 75-83 includes, wherein the anchor is configured to take up the lace around the anchor.

In Example 85, the subject matter of Examples 75-84 includes, wherein the lace cable includes a first lace cable and a separate second lace cable.

In Example 86, the subject matter of Examples 75-85 includes, wherein the first lace cable forms a first lacing zone extending proximally from a proximal side of the adaptive engine, and the second lace cable forms a second lacing zone extending distally from a distal side of the adaptive engine.

In Example 87, the subject matter of Examples 75-86 includes, wherein the second lace cable is routed from a distal end of the adaptive support garment along the perimeter of the support structure to a proximal end.

In Example 88, the subject matter of Examples 75-86 includes, wherein the adaptive engine is positioned at a mid-point along a proximal-distal length of the support structure.

Example 89 is an adaptive support garment comprising: a support structure configured to wrap around a portion of anatomy of a wearer to provide compression to the portion of the anatomy; a plurality of lace guides disposed on the support structure; a lace cable, extending through the lace guides to form a lacing pattern over a lacing region of the support structure; an adaptive engine coupled to the support structure and engaged with the lace cable, wherein the adaptive engine is configured to increase or decrease tension on the lace cable to increase or decrease compression of the support structure, respectively; and an airbag, positioned between the lacing region and a wearer-facing surface of the adaptive support garment, the airbag configured to distribute force from the lace cable along the airbag.

In Example 90, the subject matter of Example 89 includes, wherein the airbag forms a notch sized to receive, at least in part, the adaptive support engine and wherein the adaptive support engine is disposed in the notch.

In Example 91, the subject matter of Examples 89 and 90 includes, wherein the adaptive support engine is configured to be drawn into the notch upon a tension being placed on the lace cable.

In Example 92, the subject matter of Examples 89-91 includes, wherein the notch is positioned at a center point along a proximal-distal length of the airbag.

In Example 93, the subject matter of Examples 89-92 includes, wherein the support structure comprises a first layer and a second layer forming a cavity therebetween, wherein the airbag is positioned within the cavity.

In Example 94, the subject matter of Examples 89-93 includes, a stiffening element extending longitudinally along a longitudinal axis of the support structure.

In Example 95, the subject matter of Examples 89-94 includes, wherein the stiffening element extends along a first side of the lacing region.

In Example 96, the subject matter of Examples 89-95 includes, wherein the stiffening element is a first stiffening element and further comprising a second stiffening element positioned along a second side of the lacing region opposite the first side of the lacing region.

In Example 97, the subject matter of Examples 89-96 includes, wherein the stiffening element is positioned between the first and second layers.

In Example 98, the subject matter of Examples 89-97 includes, wherein the airbag is substantially coextensive with the lacing region.

In Example 99, the subject matter of Examples 89-98 includes, a pressure sensor configured to detect a pressure within the airbag, the pressure sensor operatively coupled to the adaptive engine, wherein the adaptive engine is configured to increase or decrease tension on the lace based in part on the pressure within the airbag detected by the pressure sensor.

In Example 100, the subject matter of Examples 89-99 includes, wherein the pressure sensor is positioned within the airbag.

In Example 101, the subject matter of Examples 89-100 includes, wherein the adaptive engine is disposed in the center of the support structure.

In Example 102, the subject matter of Examples 89-101 includes, wherein the lacing pattern extends above and below the adaptive engine along a longitudinal axis of the support structure.

In Example 103, the subject matter of Examples 89-102 includes, wherein the lace cable extends from opposing sides of the adaptive engine.

In Example 104, the subject matter of Examples 89-103 includes, wherein the adaptive engine includes a spool configured to take up the lace cable, wherein the lace cable is configured to exit the spool on opposing sides of the spool.

In Example 105, the subject matter of Examples 89-104 includes, wherein the lace cable forms a crisscross pattern across the lacing region of the support structure above and below the adaptive engine.

In Example 106, the subject matter of Examples 89-105 includes, wherein the support structure comprises a first half and a second half and a zipper extending along the longitudinal axis of the support structure, the zipper configured to join the first half to the second half to form the tubular support structure.

In Example 107, the subject matter of Examples 89-106 includes, wherein the support structure comprises a first elastic portion extending between a first side of the lacing region and the zipper and a second elastic portion extending between a second side of the lacing region and the zipper.

In Example 108, the subject matter of Examples 89-107 includes, wherein the first and second elastic portions are formed from a mesh.

In Example 109, the subject matter of Examples 89-108 includes, wherein the portion of anatomy of the wearer is a first portion wherein the support structure forms a flared portion below the lacing region to admit a second portion of anatomy of the wearer.

In Example 110, the subject matter of Examples 89-109 includes, wherein the flared portion is sized to admit an ankle of the wearer.

In Example 111, the subject matter of Examples 89-110 includes, wherein the lacing pattern does not extend into the flared portion.

In Example 112, the subject matter of Examples 89-111 includes, wherein the flared portion is not compressed upon tensioning the lace cable.

In Example 113, the subject matter of Examples 89-112 includes, wherein the lacing pattern is a split helix pattern.

In Example 114, the subject matter of Examples 89-113 includes, wherein the split helix pattern is formed along a medial section of an inferior portion of the support structure and along a lateral section of a superior portion of the support structure.

Example 115 is a method for operating an adaptive compression garment, the method comprising: activating a control circuit communicatively coupled to an adaptive engine on the adaptive compression garment; receiving, on the control circuit, a selection of a compression sequence; transmitting, from the control circuit to the adaptive engine, a series of compression and release commands; and operating the adaptive engine in response to the series of compression and release commands to perform the compression sequence.

In Example 116, the subject matter of Example 115 includes, wherein operating the adaptive engine includes engaging a lacing system with the adaptive engine to tension the lacing system in response to a compression command.

In Example 117, the subject matter of Examples 115-116 includes, wherein tensioning the lacing system includes shortening an effective length of a lace cable within the lacing system to create a compression of the adaptive compression garment.

In Example 118, the subject matter of Examples 115-117 includes, wherein operating the adaptive engine includes engaging a lacing system with the adaptive engine to loosen the lacing system in response to a release command.

In Example 119, the subject matter of Examples 115-118 includes, wherein loosening the lacing system includes lengthening an effective length of a lace cable within the lacing system to release a compression of the adaptive compression garment.

In Example 120, the subject matter of Examples 115-119 includes, wherein the series of compression and release commands includes compression commands, hold commands, and release commands arranged in pre-defined sequences.

In Example 121, the subject matter of Examples 115-120 includes, wherein operating the adaptive engine includes rotating a lace spool engaging a lace cable of a lacing system integrated into the adaptive compression garment.

In Example 122, the subject matter of Examples 115-121 includes, wherein rotating the lace spool in a first direction shortens an effective length of the lace cable and introduces a tension into the lacing system that produces a compression within a portion of the adaptive compression garment.

In Example 123, the subject matter of Examples 115-122 includes, wherein rotating the lace spool in a second direction lengthens the effective length of the lace cable and releases the tension on the lacing system.

In Example 124, the subject matter of Examples 115-123 includes, wherein operating the adaptive engine includes manipulating a lace spool within the adaptive engine, the lace spool engaging a plurality of lace cables of a lacing system integrated into the lacing system.

Example 125 is an adaptive recovery system comprising: a first adaptive compression garment including a first lacing system coupled to a first adaptive engine configured to automatically manipulate a tension on the lacing system; a second adaptive compression garment includes, a second lacing system coupled to a second adaptive engine configured to automatically manipulate a tension on the second lacing system; and a control circuit communicatively coupled to the first adaptive engine and the second adaptive engine, the controller including a processor and memory device including instructions that, upon execution by the processor, cause the controller to transmit commands to the first adaptive engine and the second adaptive engine to coordinate tensioning of the first lacing system and the second lacing system.

In Example 126, the subject matter of Example 125 includes, wherein the memory device includes additional instructions to transmit commands to produce a series of tensioning and release cycles on the first adaptive engine and the second adaptive engine.

In Example 127, the subject matter of Examples 125-126 includes, wherein the first adaptive compression garment is configured to apply compression to an upper leg region of a wearer.

In Example 128, the subject matter of Examples 125-127 includes, wherein the second adaptive compression garment is configured to apply compression to a lower leg region of a wearer.

In Example 129, the subject matter of Examples 125-128 includes, wherein the first adaptive compression garment is configured to apply compression to a lower leg region of a wearer.

In Example 130, the subject matter of Examples 125-129 includes, an adaptive footwear assembly including a third adaptive engine coupled to a third lacing system disposed within the footwear assembly, wherein the third adaptive engine and the third lacing system are configured to apply compression to a foot of a wearer.

In Example 131, the subject matter of Examples 125-130 includes, wherein the adaptive footwear assembly comprises the control circuit.

In Example 132, the subject matter of Examples 125-131 includes, wherein the control circuit is a component of the third adaptive engine.

In Example 133, the subject matter of Examples 125-132 includes, wherein the control circuit is communicatively coupled to the first adaptive engine and the second adaptive engine via a wireless connection.

In Example 134, the subject matter of Examples 125-133 includes, wherein the control circuit is configured to coordinate tensioning of the third lacing system with the tensioning of the first and second lacing systems.

In Example 135, the subject matter of Examples 125-134 includes, wherein the first adaptive engine comprises a sensor, operatively coupled to the control circuit, configured to output a signal indicative of: a physiological condition of a wearer of the first adaptive compression garment; or a state of the first lacing system; and wherein the control circuit is further configured to coordinate tensioning of the first lacing system and the second lacing system based, at least in part, on the signal output by the sensor.

In Example 136, the subject matter of Examples 125-135 includes, wherein the sensor is a first sensor and wherein the second adaptive engine comprises a second sensor, operatively coupled to the control circuit, configured to output a signal indicative of: a physiological condition of the wearer; or a state of the second lacing system; and wherein the controller is further configured to coordinate of the first lacing system and the second lacing system based, at least in part, on the signals output by the first and second sensors.

Example 137 is a method for operating an adaptive recovery system, comprising: activating a control circuit communicatively coupled to a first adaptive engine on a first adaptive recovery garment and a second adaptive engine on a second adaptive recovery garment; receiving on the control circuit a selection of a compression sequence; transmitting, from the controller to the first and second adaptive engines a series of coordinated compression and release commands; and operating the first and second adaptive engines in response to the series of coordinated compression and release commands to perform the compression sequence.

In Example 138, the subject matter of Example 137 includes, wherein the series of coordinated compression and release commands comprise separate compression and release commands for the first and second adaptive engines to create a differential compression between the first and second adaptive recovery garments.

In Example 139, the subject matter of Examples 137 and 138 includes, wherein the series of coordinated compression and release commands further comprise separate compression and release commands for the first and second adaptive engines to dynamically change the differential compression by changing the differential compression over time.

In Example 140, the subject matter of Examples 137-139 includes, wherein operating the first and second adaptive engines includes engaging a first and second lacing system, respectively, to separately tension the first and second lacing systems, respectively in response to a compression command.

In Example 141, the subject matter of Examples 137-140 includes, wherein the compression command includes a first compression command for the first adaptive engine and a second compression command for the second adaptive engine, wherein the first compression command is separately selectable relative to the second compression command.

In Example 142, the subject matter of Examples 137-141 includes, wherein tensioning the first and second lacing systems includes shortening an effective length of a first and second lace cable, respectively, to create a compression of the first and second adaptive recovery garments, respectively.

In Example 143, the subject matter of Examples 137-142 includes, wherein operating the first and second adaptive engines includes engaging a first and second lacing system, respectively, to separately loosen the first and second lacing systems in response to a release command.

In Example 144, the subject matter of Examples 137-143 includes, wherein loosening the lacing system includes lengthening an effective length of a lace cable within the lacing system to release a compression of the adaptive recovery garment.

In Example 145, the subject matter of Examples 137-144 includes, wherein the series of compression and release commands includes compression commands, hold commands, and release commands arranged in a pre-defined sequence.

In Example 146, the subject matter of Examples 137-145 includes, wherein operating the first and second adaptive engines includes rotating a first and second lace spool, respectively, engaging a first and second lace cable, respectively, integrated into the first and second adaptive recovery garments, respectively.

In Example 147, the subject matter of Examples 137-146 includes, wherein activating the control circuit further includes communicatively coupling to a third adaptive engine integrated into a footwear assembly.

In Example 148, the subject matter of Examples 137-147 includes, wherein transmitting the series of coordinated compression and release commands includes transmitting at least a portion of the series of coordinated compression and release commands to the third adaptive engine.

In Example 149, the subject matter of Examples 137-148 includes, operating the third adaptive engine in response to the portion of the series of coordinated compression and release commands received by the third adaptive engine.

In Example 150, the subject matter of Examples 137-149 includes, wherein the portion of the series of coordinated compression and release commands received by the third adaptive engine create at least one of: a differential compression between the footwear assembly and at least one of the first and second adaptive recovery garments, and a dynamically changing differential compression between the footwear assembly and at least one of the first and second adaptive recovery garments.

Example 151 is a method for operating an adaptive compression system, the method comprising: activating a control circuit communicatively coupled to a first adaptive recovery garment and a second adaptive recovery garment, the first adaptive recovery garment adapted to apply compression to a first portion of anatomy and the second adaptive recovery garment adapted to apply compression to a second portion of anatomy; receiving, on a control circuit, a selection of a coordinated recovery sequence, the coordinated recovery sequence comprising a series of coordinated compression and release commands including a first series of compression and release commands and a second series of compression and release commands; executing, on the first adaptive recovery garment, the first series of compression and release commands; and executing, on the second adaptive recovery garment in coordination with the first adaptive recovery garment, the second series of compression and release commands.

Example 152 a system with sensor and control information derived from footwear sensors and/or apparel sensors, and processed by a central control device (e.g., a smart phone or central processing system within a lacing engine).

Example 153 is at least one machine-readable medium including instructions that, when executed by processing circuitry, cause the processing circuitry to perform operations to implement of any of Examples 1-152.

Example 154 is an apparatus comprising means to implement of any of Examples 1-152.

Example 155 is a system to implement of any of Examples 1-152.

Example 156 is a method to implement of any of Examples 1-152.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein, such as operation of adaptive support garment examples, can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. An Abstract, if provided, is included to comply with United States rule 37 C.F.R. § 1.72(b), to allow the reader to quickly ascertain the nature of the technical disclosure. It is submitted with the understanding that it will not be used to interpret or limit the scope or meaning of the claims. Also, in the above Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An adaptive support garment comprising:
a support structure configured to wrap around a portion of anatomy of a wearer and apply a compression on the portion of anatomy, the support structure including a tubular support structure open along a lacing region to form a first edge and a second edge;
a plurality of lace guides disposed on the support structure;
a lace cable, extending through the lace guides to form a lacing pattern over the lacing region of the support structure to bring the first edge and the second edge together; and
an adaptive engine, coupled to the support structure and engaged with the lace cable, wherein the adaptive engine is configured to increase or decrease tension on the lace cable to increase or decrease compression of the support structure on the portion of anatomy, respectively.

2. The adaptive support garment of claim 1, wherein the lacing pattern forms a crisscross lacing pattern over the lacing region.

3. The adaptive support garment of claim 2, wherein the crisscross lacing pattern extends across a separation between the first edge and the second edge along the lacing region.

4. The adaptive support garment of claim 1, wherein the adaptive engine is disposed in a center of the support structure.

5. The adaptive support garment of claim 4, wherein the lacing pattern extends above and below the adaptive engine along a longitudinal axis of the support structure.

6. The adaptive support garment of claim 1, wherein the lace cable extends from opposing sides of the adaptive engine.

7. The adaptive support garment of claim 6, wherein the adaptive engine includes a spool configured to take up the lace cable, wherein the lace cable is configured to exit the spool on opposing sides of the spool.

8. The adaptive support garment of claim 1, wherein the support structure includes a zipper extending along a longitudinal axis of the support structure, the zipper configured to join the first edge to the second edge to form the tubular support structure.

9. The adaptive support garment of claim 8, wherein the support structure comprises a first elastic portion extending between a first side of the lacing region and the zipper and a second elastic portion extending between a second side of the lacing region and the zipper.

10. The adaptive support garment of claim 1, wherein the lacing pattern is a split helix pattern.

11. The adaptive support garment of claim 10, wherein the split helix pattern is formed along a medial section of an inferior portion of the support structure and along a lateral section of a superior portion of the support structure.

12. An adaptive support garment comprising:
a support structure configured to wrap around a portion of anatomy of a wearer and apply a compression on the portion of anatomy;

a plurality of lace guides disposed on the support structure along a longitudinal axis;

a lace cable, extending through the plurality of lace guides to form a crisscross lacing pattern over a lacing region of the support structure; and an adaptive engine, coupled to the support structure and engaged with the lace cable, wherein the adaptive engine is configured to increase or decrease tension on the lace cable to increase or decrease compression of the support structure on the portion of anatomy, respectively.

13. The adaptive support garment of claim 12, wherein the support structure comprises a first edge and a second edge drawn together to form a tubular support structure, and wherein the crisscross lacing pattern extends across a separation between the first edge and the second edge along the lacing region.

14. The adaptive support garment of claim 12, wherein the adaptive engine is positioned within the lacing region of the support structure.

15. The adaptive support garment of claim 14, wherein the adaptive engine is positioned over a center point of the lacing region of the support structure.

16. The adaptive support garment of claim 15, wherein the lace cable extends from opposing sides of the adaptive engine.

17. The adaptive support garment of claim 16, wherein the lace cable forms a crisscross pattern across the lacing region of the support structure above and below the adaptive engine.

18. The adaptive support garment of claim 12, wherein the lace cable includes a first lace cable and a separate second lace cable.

19. The adaptive support garment of claim 18, wherein the first lace cable forms a first lacing zone extending proximally from a proximal side of the adaptive engine, and the second lace cable forms a second lacing zone extending distally from a distal side of the adaptive engine.

20. The adaptive support garment of claim 19, wherein the second lace cable is routed from a distal end of the adaptive support garment along a perimeter of the support structure to a proximal end.

* * * * *